US007678391B2

(12) United States Patent
Graham et al.

(10) Patent No.: US 7,678,391 B2
(45) Date of Patent: *Mar. 16, 2010

(54) FORMULATIONS AND METHODS OF USING NITRIC OXIDE MIMETICS AGAINST A MALIGNANT CELL PHENOTYPE

(75) Inventors: Charles H. Graham, Kingston (CA); Lynn-Marie Postovit, Kingston (CA); Michael A. Adams, Kingston (CA); Jeremy P. W. Heaton, Gananoque (CA)

(73) Assignee: Queen's University at Kingston

( * ) Notice: Subject to any disclaimer, the term of this patent is extended or adjusted under 35 U.S.C. 154(b) by 649 days.

This patent is subject to a terminal disclaimer.

(21) Appl. No.: 10/384,499

(22) Filed: Mar. 6, 2003

(65) Prior Publication Data

US 2003/0215528 A1    Nov. 20, 2003

Related U.S. Application Data

(63) Continuation-in-part of application No. 10/042,039, filed on Oct. 25, 2001, now abandoned, which is a continuation-in-part of application No. 09/842,547, filed on Apr. 26, 2001, now Pat. No. 6,946,484.

(60) Provisional application No. 60/362,620, filed on Mar. 7, 2002, provisional application No. 60/362,969, filed on Mar. 6, 2002, provisional application No. 60/277,469, filed on Mar. 21, 2001, provisional application No. 60/199,757, filed on Apr. 26, 2000.

(51) Int. Cl.
*A61K 31/21* (2006.01)
*A61K 33/00* (2006.01)
*A01N 37/00* (2006.01)

(52) U.S. Cl. .................. 424/718; 514/509; 514/929

(58) Field of Classification Search ................ 424/718, 424/646, 648; 514/470, 502, 562, 727, 929
See application file for complete search history.

(56) References Cited

U.S. PATENT DOCUMENTS

| | | | | |
|---|---|---|---|---|
| 3,742,951 | A | * | 7/1973 | Zaffaroni .................... 424/434 |
| 5,434,256 | A | | 7/1995 | Khokhar et al. |
| 5,554,638 | A | | 9/1996 | Dewhirst et al. |
| 5,650,442 | A | | 7/1997 | Mitchell et al. |
| 5,652,255 | A | * | 7/1997 | Adams et al. ................ 514/398 |
| 5,700,830 | A | | 12/1997 | Korthuis et al. |
| 5,814,667 | A | | 9/1998 | Mitchell et al. |
| 5,837,736 | A | | 11/1998 | Mitchell et al. |
| 5,840,759 | A | | 11/1998 | Mitchell et al. |
| 5,849,790 | A | | 12/1998 | Palmer et al. |
| 5,880,129 | A | | 3/1999 | Kohn et al. |
| 5,942,385 | A | | 8/1999 | Hirth |
| 5,965,360 | A | | 10/1999 | Zain et al. |
| 5,994,298 | A | * | 11/1999 | Tsai et al. ...................... 514/8 |
| 6,057,367 | A | | 5/2000 | Stamler et al. |
| 6,103,275 | A | | 8/2000 | Seitz et al. |
| 6,153,186 | A | | 11/2000 | Stamler et al. |
| 6,171,620 | B1 | | 1/2001 | Piver et al. |
| 6,180,824 | B1 | | 1/2001 | Stamler et al. |
| 6,203,789 | B1 | | 3/2001 | Stamler et al. |
| 6,235,782 | B1 | | 5/2001 | Pamukcu et al. |
| 6,270,779 | B1 | | 8/2001 | Fitzhugh et al. |
| 2001/0038832 | A1 | | 11/2001 | Bonavida et al. |
| 2002/0010146 | A1 | | 1/2002 | Garvey et al. |
| 2003/0092637 | A1 | | 5/2003 | Magnusson et al. |
| 2003/0215528 | A1 | | 11/2003 | Graham et al. |

FOREIGN PATENT DOCUMENTS

| | | |
|---|---|---|
| DE | 19732323 C2 | 8/1999 |
| WO | WO 93/20806 | 10/1993 |
| WO | WO 96/15781 | 5/1996 |
| WO | WO 96 30336 | 10/1996 |
| WO | WO 98/13358 | 4/1998 |
| WO | WO 98/58633 | 12/1998 |
| WO | WO 99 03462 | 1/1999 |
| WO | WO 99/33823 | 7/1999 |
| WO | WO 99/48916 | 9/1999 |
| WO | WO 99/57306 | 11/1999 |
| WO | WO 00/51597 | 9/2000 |
| WO | WO 01 54680 | 8/2001 |
| WO | WO 01/54771 A2 | 8/2001 |
| WO | WO 01/70199 | 9/2001 |
| WO | WO 01 80890 | 11/2001 |

OTHER PUBLICATIONS

Webster's New World Dictionary, 3rd College Edition, Simon & Schuster, Inc., New York, 1988, pp. 1067-1068.*
Stedman's Medical Dictionary, 26th ed., Williams & Wilkins, Baltimore, 1995, p. 1065, definition of "tumor marker."*
Stedman's Medical Dictionary, 26th ed., Williams & Wilkins, Baltimore, 1995, p. 104, entry for "prostate-specific a. (PSA)".*
HCAPLUS abstract 1998:689890 (1998).*
HCAPLUS abstract 1995:842132 (1995).*
Medline abstract 93363659 (1993).*
Medline abstract 96437201 ((1997).*
Medline abstract 96330672 (1996).*
The Merck Index, 12th ed., Merck & Co., Whitehouse Station (NJ), 1996, pp. 625, 1119 and 1223.*
Medline abstract 1999350811 (1999).*

(Continued)

*Primary Examiner*—Ernst V Arnold
(74) *Attorney, Agent, or Firm*—Stephen J. Scribner; Carol Miernicki Steeg

(57) ABSTRACT

The present invention relates to methods and formulations for inhibiting, treating and preventing a malignant cell phenotype, cell, tumor and/or disease. Administration of nitric oxide mimetics, such as low doses, is sufficient to increase, restore or maintain nitric oxide-mediated signaling in cells so that malignant cell phenotypes, cells, tumors and/or diseases are inhibited or prevented. These methods and formulations are particularly useful in treating and preventing cancer in animals.

24 Claims, 18 Drawing Sheets

OTHER PUBLICATIONS

Pipili-Synetos et al. (British Journal of Pharmacology 1995, 116, 1829-1834).*

Brizel et al., "Tumor Hypoxia Adversely Affects the Prognosis of Carcinoma of the Head and Neck", *Int. J. Radiation Oncology Biol. Phys.* 1997 38(2):285-289.

Brizel et al., "Tumor Oxygenation Predicts for the Likelihood of Distant Metastases in Human Soft Tissue Sarcoma", *Cancer Research* 1996 56:941-943.

Harris et al., "Breast cancer angiogenesis-new approaches to therapy via antiangiogenesis, hypoxic activated drugs, and vascular targeting", *Breast Cancer Research and Treatment* 1996 38:97-108.

Höckel et al., "Association between Tumor Hypoxia and Malignant Progression in Advanced Cancer of the Uterine Cervix", Cancer Research 1996 56:4509-4515.

Kong et al., "Nitric oxide reduces tumor cell adhesion to isolated rat postcapillary venules", *Clin. Exp. Metastasis* 1996 14:335-343.

Mitchell et al., "Radiation sensitisation by nitric oxide releasing agents", *British Journal of Cancer* 1996 74:(Suppl. XXVII) S181-S184.

Mitchell et al., "Hypoxic mammalian cell radiosensitization by nitric oxide", *Cancer Research* 1993 53(24) 5845-5848 (Abstract Only).

Mitchell et al., "Hypoxic Mammalian Cell Radiosensitization by Nitric Oxide", *Cancer Research* 1993 53:5845-5848.

Pipili-Synetos et al., "Inhibition of angiogenesis, tumour growth and metastasis by the NO-releasing vasodilators, isosorbide mononitrate and dinitrate", *British Journal of Pharmacology* 1995 116:1829-1834.

Teicher B.A., "Hypoxia and drug resistance", Cancer and Metastasis Reviews 1994 13:139-168.

Trikha et al., "Nitroglycerin:a NO donor inhibits TPA-mediated tumor promotion in murine skin", *Carcinogenesis* 2001 22(8):1207-1211.

Wink et al., "Chemical biology of nitric oxide:Insights into regulatory, cytotoxic, and cytoprotective mechanisms of nitric oxide", *Free Radio Biol Med* 1998 25(4-5):434-458 (Abstract Only).

Wink et al., "Nitric Oxide and Some Nitric Oxide Donor Compounds Enhance the Cytotoxicity of Cisplatin", *Nitric Oxide:Biology and Chemistry* 1997 1(1):88-94.

Xie et al., "Therapy of cancer metastasis by activation of the inducible nitric oxide synthase", *Cancer and Metastasis Reviews* 1998 17:55-75.

Xie et al., "Transfection with the Inducible Nitric Oxide Synthase Gene Suppresses Tumorigenicity and Abrogates Metastasis by K-1735 Murine Melanoma Cells" *J. Exp. Med.* 1995 181:1333-1343.

Young et al., "Hypoxia induces DNA overreplication and enhances metastatic potential of murine tumor cells", *Proc. Natl. Acad. Sci. USA* 1988 85:9533-9537.

Jun Chang-Duk et al.; "High-dose nitric oxide Induces apoptosis in HL-60 human myeloid leukemia cells"; Experimental and Molecular Medicine; Jun. 1996; pp. 101-108; vol. 23, No. 2.

Sumitani et al.; "Cytotoxic Effect of Sodium Nitroprusside on Cancer Cells: Involvement of Apoptosis and Suppression of C-MYC and C-MYB Proto-oncogene Expression"; Anticancer Research, Helenic Anticancer Institute, Athens, GR.; Mar. 1997; pp. 865-872; vol. 17, No. 2A.

Dookeran: Mechanisms of Antitumor Activity for Sustained-Release Nitroc-Oxide Donor, Nitroprusside in Ethiodol; Proceedings of the Annual Meeting of the American Aseociation for Cancer Research; 2000; p. 280; vol. 41, No. 41.

Carducci et al., "Effect of endothelin-a receptor blockage with atrasentan on tumor progression in men with hormone-refractory prostate cancer: a randomized, phase ii, placebo-controlled trial" J. Clin. Oncol. 21(94):679-689 (2003).

Chen et al., "Identification of the enzymatic mechanism of nitroglycerin bioactivation" PNAS 99(12):8306-8311 (2002).

Eley, K. et al., "The effects of pentoxifylline on the survival of human glioma cells with continuous and intermittent stereotactic radiosurgery irradiation" Int. J. Radiat. Oncol. Biol. Phys. 54(2):542-550 (2002).

Kim el al., "Type 4 cyclic adenosine monophosphate phosphodiesterase as a therapeutic target in chronic lymphocytic leukemia" Blood 92(7):2484-2494 (1998).

Mannick et al., "Fas-induced caspase denitrosylation" Science 284:651-654 (1999).

Marshall et al., "Exhaled nitric oxide (NO), NO synthase activity, and regulation of nuclear factor (nf)—kb" Am. J. Respir. Cell Mol. Biol. 21:296-297 (1999).

Marshall et al., "Nitrosative stress-induced apoptosis through inhibition of nf-kb" J. Biol. Chem. 277(37):34223-34228 (2002).

Pallavicini, M. et al., "Effect of tumor blood flow manipulations on radiation response" Int. J. Radial Oncol. Biol. Phys. 9(9):1321-5 (1983) [Abstract].

Stix, G., "Saying yes to NO" Scientific American p. 34 (Nov. 2001).

Sun et al., "Cysteine-3635 is responsible for skeletal muscle ryanodine receptor modulation by NO" PNAS 98(20):11158-11162 (2001).

Umansky, V. et al., "Activated endothelial cells induce apoptosis in lymphoma cells: role of nitric oxide" Int. J. Oncol. 10:465-471 (1997).

Umansky, V. et al., "Nitric oxide-mediated apoptosis in human breast cancer cells requires changes in mitochondrial functions and is independent of CD95 (APO-1/Fas)" Int. J. Oncol. 16(1):109-117 (2000).

Ushmorov, A. et at., "Nitric oxide-induced apoptosis in human leukemic lines requires mitochondrial lipid degradation and cytochrome C release" Blood 93(7):2342-2352 (1999).

Yp et al., "Topical applications of caffeine or (−) opigallocatechin gallato (egcg) inhibit carcinogenesis and selectivity increase apoptosis in evb-induced skin tumors in mice" PNAS USA 19:12455-12480 [Abstract].

Iversen, H.K., et al., "Dose-dependent headache response and dilatation of limb and extracranial arteries after three doses of 5-isosorbide-mononitrate", Eur. J. Clin. Pharm. 42: 31-35 (1992).

* cited by examiner

A

B

A

B

US 7,678,391 B2

FORMULATIONS AND METHODS OF USING NITRIC OXIDE MIMETICS AGAINST A MALIGNANT CELL PHENOTYPE

CROSS-REFERENCE TO RELATED APPLICATIONS

This application claims the benefit of U.S. Provisional Application Ser. Nos. 60/362,969 filed Mar. 6, 2002, and 60/362,620 filed Mar. 7, 2002, and U.S. patent application Ser. No. 10/042,039, filed Oct. 25, 2001, which are herein incorporated by reference. U.S. patent application Ser. No. 10/042,039 is a continuation-in-part of U.S. application Ser. No. 09/842,547, filed Apr. 26, 2001, now U.S. Pat. No. 6,946,484, issued Sep. 20, 2005, which claims the benefit of U.S. Provisional Application Nos. 60/277,469, filed Mar. 21, 2001, and 60/199,757, filed Apr. 26, 2000, which are herein incorporated by reference in their entirety.

FIELD OF THE INVENTION

The present invention relates to methods and formulations for inhibiting, treating and preventing a malignant cell phenotype, cell, tumor and/or disease. We have now found that the mechanism by which hypoxia and hyponitroxia have impact upon cellular phenotype is not necessarily mediated solely by the lack of oxygen but rather also from a deficiency in nitric oxide mediated signaling. Accordingly, as demonstrated herein, administration of nitric oxide mimetics, such as low doses, is sufficient to increase, restore or maintain nitric oxide-mediated signaling in cells so that malignant cell phenotypes, cells, tumors and/or diseases are inhibited or prevented. Thus, provided herein are formulations and methods of using these formulations to deliver low doses of nitric oxide mimetics to cells at levels which inhibit a malignant cell phenotype, cell, tumor and/or disease to treat and/or prevent development of a malignant cell phenotype, cell, tumor and/or disease but which reduce or avoid development of unwanted effects of the NO mimetics. These methods and formulations are particularly useful in treating and preventing cancer in animals.

BACKGROUND OF THE INVENTION

Hypoxia or oxygen tension below normal physiologic levels in cells results in physiologic as well as pathologic alterations in the cells, which alterations have been associated with differential gene expression. For example, hypoxia affects endothelial cellular physiology in vivo and in vitro in various ways including modulating the transcriptionally-regulated expression of vasoactive substances and matrix proteins involved in modulating vascular tone or remodeling the vasculature and surrounding tissue (Faller, D. V. *Clin. Exp. Pharmacol. and Physiol.* 1999 26:74-84). Hypoxia in solid tumors has been shown to protect cancer cells from being killed by X-irradiation and leads to resistance to certain cancer drugs. Hypoxia also appears to accelerate malignant progression and increase metastasis (Brown, J. M. *Cancer Res.* 1999 59:5863-5870).

Low oxygen levels have been shown to enhance invasiveness in a number of cell types, and likely promote invasive phenotypes in biological environments such as the core of rapidly growing tumors. Studies in our laboratory suggest that this effect is mediated via a reduction in nitric oxide (NO) production. For example, the inhibition of endogenous NO production (that occurs under hypoxic conditions or in the presence of a NOS inhibitor) was shown to up-regulate both the expression of the urokinase receptor (uPAR, a pro-invasive molecule) and metastasis. Further, the hypoxic upregulation of (uPAR) and metastasis was completely abrogated by the addition of very low concentrations of NO-mimetics.

Nitric oxide has been implicated in various biological processes. For example, nitric oxide is a biological messenger molecule responsible for endothelium derived vascular relaxation and neurotransmission. Nitric oxide, at what these researchers refer to as high levels, is also known as a mediator for anti-tumor and anti-bacterial actions of macrophages. Nitric oxide has also been demonstrated to play a modulatory role on cytokine-induced expression of matrix metalloproteinase-9 and tissue inhibitors of metalloproteinases (Eberhardt et al. *Kidney International* 2000 57:59-69).

Soluble guanylyl cyclase (sGC) is the best defined downstream target of NO. However, since NO is a pleiotropic molecule, it is likely that there are other molecular targets that mediate NO action. For example, it is very likely that NO could attenuate gene expression via currently unknown mechanisms and, as such, impact various cellular functions, such as growth, proliferation, migration, apoptosis, and the like. The heterodimeric protein, i.e., sGC, catalyzes the conversion of guanosine 5'-triphosphate (GTP) to cyclic guanosine monophosphate (cGMP). Nitric oxide binds to the heme moiety of sGC, inducing a number of conformational changes that result in its activation cGMP is a potent second messenger that allows NO to transmit its signal to downstream effectors. Elevated levels of cGMP have been negatively correlated with vascular smooth muscle growth and have been shown to prevent platelet aggregation as well as the adherence of neutrophils to endothelial cells. Further, cGMP levels play a role in gene regulation. A cGMP analogue (8-Br-cGMP) has been shown to prevent the hypoxic induction of VEGF. The endogenous inhibition of endothelin-1 (ET-1) by NO is also mediated through a guanylate cyclase/cGMP-dependent mechanism.

There are several cGMP target proteins that could mediate NO-regulated gene expression. These include cGMP-dependent protein kinase (PKG), cGMP-activated phosphodiesterases (PDEs), and cGMP-gated ion channels, and under certain conditions, cAMP-dependent protein kinases. Of these, it is thought that PKG is responsible for the majority of cGMP's intracellular actions. PKG is a serine/threonine protein kinase that is selectively activated by cGMP binding. Upon activation, PKG phosphorylates many intracellular targets, often resulting in alterations in gene expression. For example, PKG has been shown to modulate the transcription of various genes through its activation of factors such as AP-1 and the serum response element. Similarly, Idriss et al. has shown that the c-fos promoter is activated by a PKG dependent mechanism.

Clinical and experimental data suggest that nitric oxide plays a role in promoting solid tumor growth and progression. For example, nitric oxide generation by inducible nitric oxide synthase (iNOS) has been implicated in the development of prostate cancer (Klotz et al. Cancer; National Library of Medicine, *MDX Health Digest* 1998 82(10):1897-903), as well as in colonic adenocarcinomas and mammary adenocarcinomas (Lala, P. K. and Orucevic, A., *Cancer and Metastasis Reviews* 1998 17:91-106). In addition, nitric oxide has been suggested to play an important role in the metabolism and behavior of lung cancers, and in particular adenocarcinomas (Fujimoto et al. *Jpn. J. Cancer Res* 1997 88: 1190-1198). In fact, it has been suggested that tumor cells producing or exposed to what these researchers refer to as low levels of nitric oxide, or tumor cells capable of resisting nitric oxide-mediated injury undergo a clonal selection because of their survival advantage (Lala, P. K. and Orucevic, A. *Cancer and Metastasis Review* 1998 17:91-106). These authors suggest that these tumor cells utilize certain nitric oxide-mediated mechanisms for promotion of growth, invasion and metastasis and propose that nitric oxide-blocking drugs may be useful in treating certain human cancers. There is also evidence indicating that tumor-derived nitric oxide promotes tumor angiogenesis as well as invasiveness of certain tumors in animals, including humans (Lala, P. K. *Cancer and Metastasis Reviews* 1998 17:1-6).

However, nitric oxide has been reported to reverse production of vasoconstrictors induced by hypoxia (Faller, D. G. *Clinical and Experimental Pharmacology and Physiology* 1999 26:74-84). In addition, the nitric oxide donors sodium nitroprusside, S-nitroso-L-glutathione and 3-morpholinosydnonimine in the micromolar range ($IC_{50}$=7.8, 211 and 490 µM, respectively) have been demonstrated to suppress the adaptive cellular response controlled by the transcription factor hypoxia-inducible factor-1 in hypoxically cultured Hep3B cells, a human hepatoma cell line (Sogawa et al. *Proc. Natl Acad. Sci. USA* 1998 95:7368-7373). The nitric oxide donor sodium nitroprusside (SNP; 150 µM) has also been demonstrated to decrease hypoxia-induced expression of vascular endothelial growth factor, an endothelial cell mitogen required for normal vascular development and pathological angiogenic diseases such as cancer and iris and retinal neovascularization (Ghiso et al. *Investigative Ophthalmology & Visual Science* 1999 40(6):1033-1039). In these experiments, 150 µM SNP was demonstrated to completely suppress hypoxia-induced VEGF mRNA levels for at least 24 hours in immortalized human retinal epithelial cells.

High levels of nitric oxide, when induced in certain cells, can cause cytostasis and apoptosis. For example, Xie et al. have demonstrated exposure to high levels of nitric oxide (producing approximately 75 µM nitrite; see FIG. 5A of Xie et al.) to be an exploitable phenomenon to promote death (see FIGS. 6A and 6B of Xie et al.) in murine K-1735 melanoma cells (*J. Exp. Med.* 1995 181:1333-1343). In addition, WO 93/20806 discloses a method of inducing cell cytostasis or cytotoxicity by exposing cells to a compound such as spermine-bis(nitric oxide) adduct monohydrate at 500 µM which is capable of releasing nitric oxide in an aqueous solution. The compounds are taught to be useful in the treatment of tumor cells as well as in antiparasitic, antifungal and antibacterial treatments. Use of a mega-dosing regimen is suggested, wherein a large dose of the nitric oxide releasing compound is administered, time is allowed for the active compound to act, and then a suitable reagent such as a nitric oxide scavenger is administered to the individual to render the active compound inactive and to stop non-specific damage. It is taught at page 14, line 25-30 of WO 93/20806 that 3-(n-propyl amino)propylamine bis(nitric oxide) adduct, diethylamine-bis(nitric oxide) adduct sodium salt, isopropylamine-bis(nitric oxide) adduct sodium salt, sodium trioxodinitrate (II) monohydrate, and N-nitrosohydroxylamine-N-sulfonate did not significantly affect cell viability at concentrations up to 500 µM.

U.S. Pat. No. 5,840,759, U.S. Pat. No. 5,837,736, and U.S. Pat. No. 5,814,667, disclose methods for using mg/kg quantities of nitric oxide releasing compounds to sensitize hypoxic cells in a tumor to radiation. These patents also disclose methods of using the same nitric oxide-releasing compounds at mg/kg levels to protect non-cancerous cells or tissue from radiation, to sensitize cancerous cells to chemotherapeutic agents, and to protect non-cancerous cells or tissue from chemotherapeutic agents. Compounds used in these methods spontaneously release nitric oxide under physiologic conditions without requiring oxygen. These patents teach administration of the nitric oxide-releasing compound from about 15 to about 60 minutes prior to therapy. Typical doses of the nitric oxide releasing compound administered are suggested to be from about 0.1 to about 100 mg of one or more nitric oxide releasing compounds per kg of body weight. Concentrations of the nitric oxide releasing compounds DEA/NO and PAPA/NO demonstrated to increase the sensitivity of MCF7 breast cancer cells and V79 fibroblasts to melphalan, thiotepa, mitomycin C, SR4233 and cisplatin in vitro were in the millimolar range while 70 mg/kg of DEA/NO was demonstrated to increase the survival of mice administered the chemotherapeutic agent melphalan in the in vivo KHT tumor model.

U.S. Pat. No. 5,700,830 and WO 96/15781 disclose methods for inhibiting adherence between cancerous cells and non-cancerous cells in an animal by administering to the animal a nitric oxide-releasing compound containing a nitric oxide-releasing $N_2O_2$ functional group. However, studies indicate that cancer cell adhesion to and spreading along the vessel wall leading to extravasation is not an obligatory event in metastasis (Morris et al. *Exp. Cell. Res.* 1995 219:571-578).

WO 98/58633 discloses a microdose nitric oxide therapy for alleviating vascular conditions associated with a reduction in nitric oxide production or an attenuation of nitric oxide effect.

SUMMARY OF THE INVENTION

The present invention provides methods and formulations for administering nitric oxide mimetics to cells to inhibit, to treat and to prevent a malignant cell phenotype, cell, tumor and/or disease. In certain preferred aspects, the nitric oxide mimetic is administered in a low dose. Advantageously, in certain aspects, the nitric oxide mimetics of the present invention increase the efficacy of palliative treatment, by relieving or reducing the intensity of uncomfortable symptoms associated with cancer, such as pain, nausea, and shortness of breath.

In one aspect, the present invention provides a method useful for controlling, treating, and/or preventing cancer, malignancies, neoplasm, hyperplasia, hypertrophy, dysplasia and/or tumor angiogenesis, comprising administering a nitric oxide mimetic to an animal to control, treat and/or prevent cancer, malignancies, neoplasm, hyperplasia, hypertrophy, metastasis, dysplasia and/or tumor angiogenesis.

In one embodiment, the nitric oxide mimetic is administered at a low dose. In another embodiment, the nitric oxide mimetic is administered at a level which delays and/or reduces development of tolerance to the nitric oxide mimetic and/or unwanted side effects, including headache, flushing, syncope, dizziness and hypotension. In another embodiment, the nitric oxide mimetic is administered alone or in combination with an antimalignant therapeutic agent. In yet another embodiment, the nitric oxide mimetic is administered in combination with agents intended for palliative purposes including pain relief, improving physical strength and quality of life.

In another embodiment, the nitric oxide mimetic (1) inhibits the metastatic potential of a malignant cell phenotype, cell, tumor and/or disease preferably by decreasing the invasiveness, progression, growth and/or metastases of cells, tumors and/or diseases exhibiting a malignant phenotype; inhibiting the survival and/or growth of cells, tumors and/or diseases exhibiting a malignant phenotype; decreasing the progression and/or metastases of cells, tumor volume and/or diseases exhibiting a malignant phenotype; increasing the regression of cells, tumors and/or diseases exhibiting a malignant phenotype; and/or facilitating the killing of cells, tumors and/or diseases exhibiting a malignant phenotype; (2) maintains a malignant cell, tumor and/or disease in a dormant state at its primary and/or secondary site; (3) enhances the efficacy of, increases sensitivity to, and/or prevents or decreases the resistance of a malignant cell, tumor and/or disease to an antimalignant therapeutic modality; or (4) inhibits or prevents cell, tumor and/or disease angiogenesis in animals at high risk of developing cancer and/or exposed to factors known to decrease nitric oxide activity in an animal, optionally wherein said factors include decreased arginine levels, exposure to nitric oxide synthase antagonists, exposure to nitric oxide scavengers, changes in nitric oxide synthase expression, change in cofactors, glucose deprivation, surgical procedures, administration of anaesthetic agents, administration of pharmacologic agents which alter circulation, traumatic injuries, physical trauma, blood loss, decreased blood volume, or hemorrhage, or combinations thereof.

In another embodiment, the cells exhibiting the malignancies are selected from malignant cells, invasive cells, cells and tissue(s) that facilitate the malignant process, and combinations thereof; optionally wherein the malignant cell phenotype is controlled, treated or prevented by improving response to an antimalignant therapeutic modality.

In another embodiment, the nitric oxide mimetic (1) inhibits or retards the metastasis of existing tumors in a patient preferably by decreasing the invasiveness, progression, growth and/or metastases of existing tumor(s); inhibiting the survival and/or growth of existing tumor(s); decreasing the progression and/or metastases of existing tumor(s); increasing the regression of existing tumor(s); and/or facilitating the killing of existing tumor(s); (2) maintains a malignant tumor in a dormant state at its primary and/or secondary site; (3) enhances the efficacy of, increases sensitivity to, and/or prevents or decreases the resistance of tumor(s) to an antimalignant therapeutic modality; or (4) inhibits or prevents tumor angiogenesis in animals at high risk of developing cancer and/or exposed to factors known to decrease nitric oxide activity in an animal, optionally wherein said factors include decreased arginine levels, exposure to nitric oxide synthase antagonists, exposure to nitric oxide scavengers, changes in nitric oxide synthase expression, change in cofactors, glucose deprivation, surgical procedures, administration of anaesthetic agents, administration of pharmacologic agents which alter circulation, traumatic injuries, physical trauma, blood loss, decreased blood volume, or hemorrhage, or combinations thereof.

In another embodiment, the nitric oxide mimetic (1) inhibits or retards the metastasis of a cancerous disease in a patient preferably by decreasing the invasiveness, progression, growth and/or metastasis of the disease; inhibiting the survival and/or growth of the disease; decreasing the progression and/or metastasis of the disease; increasing the regression of the disease; and/or facilitating the curing and/or treatment of the disease; (2) produces or maintains remission of the disease; (3) enhances the efficacy of, increases sensitivity to, and/or prevents or decreases the resistance to an antimalignant therapeutic modality used to treat the disease; or (4) inhibits or prevents development of the disease in animals at high risk of developing cancer and/or exposed to factors known to decrease nitric oxide activity in an animal, optionally wherein the factors include decreased arginine levels, exposure to nitric oxide synthase antagonists, exposure to nitric oxide scavengers, changes in nitric oxide synthase expression, change in cofactors, glucose deprivation, surgical procedures, administration of anaesthetic agents, administration of pharmacologic agents which alter circulation, traumatic injuries, physical trauma, blood loss, decreased blood volume, or hemorrhage, or combinations thereof.

In another embodiment, the cells exhibiting the malignancies are selected from malignant cells, invasive cells, cells and tissue(s) that facilitate the malignant process, and combinations thereof, optionally wherein the malignant cell phenotype is controlled, treated or prevented by improving response to an antimalignant therapeutic modality.

In another embodiment, cancer is diagnosed or monitored by measuring a tumor selective marker present in the animal.

In another embodiment, the nitric oxide mimetic decreases, maintains, or decelerates increases of the level of the tumor marker.

In another embodiment, the cancer comprises gastric cancer, gastrointestinal cancer, testicular cancer, prostate cancer, prostatic adenocarcinoma, breast cancer, metastatic melanoma, lung cancer, the cancers set forth in Table 2 or combinations thereof. Optionally, the cancer or other malignancies, neoplasm, hyperplasia, hypertrophy, dysplasia and/or tumor angiogenesis in an animal comprises benign prostatic hyperplasia or molar pregnancy.

In another embodiment, the nitric oxide mimetic comprises nitric oxide, a nitric oxide donor, a nitric oxide prodrug, a compound that generates or releases nitric oxide through biotransformation, a compound that generates nitric oxide spontaneously or spontaneously releases nitric oxide, or a compound which generates nitric oxide, or combinations thereof.

In another embodiment, the nitric oxide mimetic is (1) a nitric oxide donor selected from nitroglycerin (GTN), isosorbide 5-mononitrate (ISMN), isosorbide dinitrate (ISDN), pentaerythritol tetranitrate (PETN), erythrityl tetranitrate (ETN), N-hydroxyl-L-arginine (NOHA), $N^6$-(1-iminoethyl)lysine (L-NIL), L-$N^5$-(1-iminoethyl)ornithine (LN-NIO), $N^\omega$methyl-L-arginine (L-NMMA), S-nitrosoglutathione (SNOG), 5,5-dinitrosodithiol (SSDD), N-[2-(nitroxyethyl)]-3-pyridinecarboxamide (nicorandil), sodium nitroprusside (SNP), S-nitroso-N-acetylpenicilamine (SNAP), 3-morpholino-sydnonimine (SIN-1), molsidomine, DEA-NONOate (2-(N,N-diethylamino)-diazenolate-2-oxide), and spermine NONOate (N-[4-[1-(3-aminopropyl)-2-hydroxy-2-nitrosohvdrazino]butyl]-1,3-propanediamine); (2) a compound that activates stages of NO pathway, a compound which enables or facilitates NO utilization by a cell, a compound which directly activates guanylyl cyclase, or a phosphodiesterase inhibitor, or combinations thereof; (3) a non-specific phosphodiesterase inhibitor, a dual-selective phosphodiesterase inhibitor, a type I, II, III, IV, V, VI, VII, VIII, IX, X, or XI phosphodiesterase inhibitor, or combinations thereof; or (4) a protein kinase G activator.

In another embodiment, the antimalignant therapeutic agent includes radiation therapy (radiotherapy), thermal therapy, immunotherapy, hormonal therapy, or single agent chemotherapy, combination chemotherapy, chemo-irradiation, adjuvant therapy, neoadjuvant therapy, palliative therapy or combinations thereof. Optionally, the antimalignant therapeutic modality comprises radiation therapy, and the nitric oxide mimetic is a nitric oxide, a nitric oxide donor, a compound that generates or releases nitric oxide through biotransformation, or a compound that generates nitric oxide spontaneously or spontaneously releases nitric oxide only in the presence of oxygen, or combinations thereof, wherein the nitric oxide mimetic is administered during the radiation therapy.

In another embodiment, the chemotherapy comprises administration of chemotherapeutic agent that is an anti-angiogenic agent, an antimetabolite, an antibiotic, an endothelin activating agent, an enzyme inhibitor, a hormonal agent, ocreotide acetate, a microtubule-disruptor agent, a microtubule-stabilizing agent, a vinca alkaloid, an epipodophyllotoxin, a topoisomerase inhibitor; a prenyl-protein transferase inhibitor, hydroxyurea, procarbazine, mitotane, hexamethylmelamine, a platinum coordination complex, a biological response modifier, a growth factor, an immune modulator, or a monoclonal antibody, or a combination thereof.

In another embodiment, the palliative therapy comprises glucocorticoid steroids, narcotic pain relief agents, anti-depressants, sex hormones, or a combination thereof.

In another embodiment, the dose of nitric oxide mimetic is at least 3- to 10,000-fold lower, preferably 100-10,000 fold lower than a dose of nitric oxide mimetic that produces vasodilation.

In another embodiment, the nitric oxide mimetic is an organic nitrate and the mimetic is administered at a dose of at least 3- to 10,000-fold lower, preferably 100-10,000 fold lower than the dose of nitric oxide mimetic known to produce vasodilation.

In another embodiment, the nitric oxide mimetic is a known vasodilatory compound and the mimetic is administered at a dose of at least 3- to 10,000-fold lower, preferably 100-10,000 fold lower than the dose of nitric oxide mimetic known to produce vasodilation In another embodiment, the nitric oxide mimetic is selected from the group consisting of a calcium channel blocker, an α-adrenergic receptor antagonist, a β-adrenergic receptor agonist, a phosphodiesterase inhibitor, a cAMP-dependent protein kinase activator, a superoxide scavenger, a potassium channel activator, a benzodiazepine, an adrenergic nerve inhibitor, an antidiarrheal agent, a HMG-CoA reductase inhibitor, an adenosine receptor modulator, a adenylyl cyclase activator, an endothelin receptor antagonist, a bisphosphonate, a cGMP-dependent protein kinase activator, a guanylyl cyclase activator and a SOC inhibitor.

These methods and formulations are particularly useful in controlling cancer by reducing its growth and improving response to therapy. For example, methods and formulations of the present invention can inhibit metastasis, invasiveness and progression of cells, tumors and/or diseases exhibiting a malignant phenotype. In addition, the methods and formulations can induce or maintain dormancy or remission of cells, tumors and/or diseases exhibiting a malignant phenotype at primary as well as secondary sites. Further, these methods and formulations can prevent or decrease development of resistance of cells, tumors and/or disease exhibiting a malignant phenotype to antimalignant therapeutic modalities, as well as increase the efficacy of antimalignant therapeutic modalities.

The methods and formulations of the present invention are also very useful in preventing a malignant cell phenotype, cell, tumor and/or disease that can develop upon exposure of cells to conditions and/or therapeutic agents which lead to a deficiency in nitric oxide mimetic activity in the cells.

The methods and formulations of the present invention are also useful in inhibiting development of a more aggressive malignant cell phenotype in cancer cells, tumors, and/or diseases, which can occur upon exposure to factors which induce such development.

In addition, these methods and formulations are useful in diagnosing and monitoring a malignant cell phenotype, cell, tumor and/or disease in an animal via detection of levels of one or more markers indicative of a malignant phenotype following administration of a low dose of a nitric oxide mimetic. No change, a decrease or deceleration in the increase of the level of one or more of these markers in an animal following administration of a low dose nitric oxide mimetic as compared to the level of the marker in the animal prior to administration of the low dose nitric oxide mimetic is indicative of a malignant phenotype in the animal. Accordingly, the methods and formulations of the present invention provide new therapeutic and diagnostic approaches for the treatment and prevention of cancer in animals.

Advantageously, the compounds, and methods described herein prolong cancer remission, prevent the recurrence of cancer, decrease cancer markers, reduce tumor volume, reduce pain, discomfort, and disability (morbidity), increase the quality of life associated with antimalignant therapeutic modalities, decrease cachexia, and reduce the need for anti-emetic agents and narcotic pain killers.

Cells were cultured for 6 hrs in 20 or 0.5% $O_2$ and in the presence or absence of GTN (1 mM). IBMX (500 mM) was included in the culture medium in order to inhibit PDE activity, thereby allowing for a measurable accumulation of cGMP. Culture in hypoxic conditions resulted in a 44% reduction in cGMP levels. This effect was completely prevented by GTN (1 mM). Values are presented as fM cGMP per mg of cellular protein +/− standard deviation. Value indicated by an asterisk (*) is significantly different as determined by a one-way analysis of variance followed by the Tukey test for pairwise multiple comparisons (N=3, P<0.05).

Figure 5:
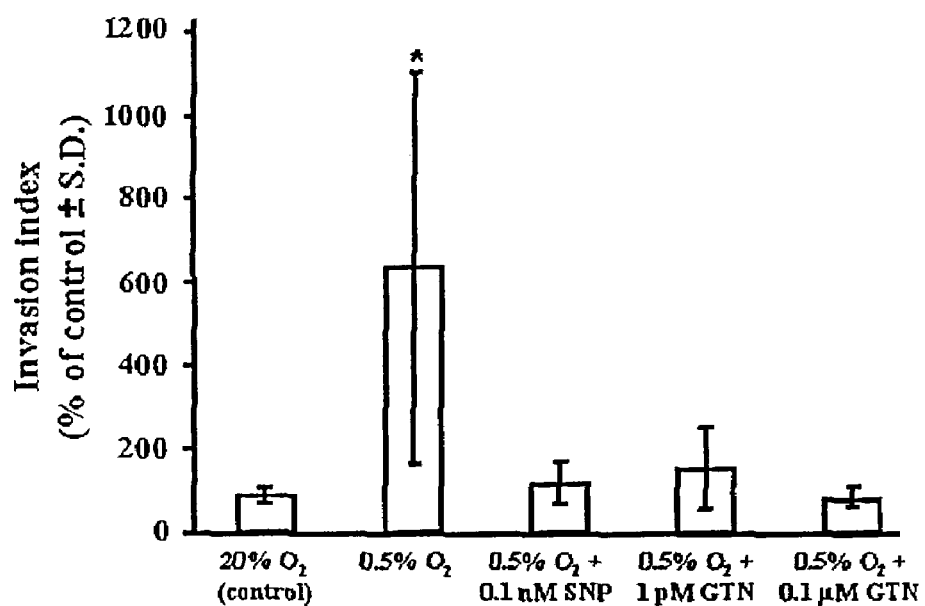

FIG. 5 illustrates the effect of GTN and SNP on the hypoxic upregulation of in vitro invasion by MDA-MB-231 cells. NO-mimetic drugs were added to the cells at the beginning of the 24-h assay and the invasion index for each treatment was calculated after counting the cells that penetrated through the membrane. Bars represent the mean, normalized, invasion indices±standard deviations. The value indicated by an asterisk (*) was significantly different from the invasion index of non-treated cells incubated in 20% $O_2$ (N=6). P values are indicated in the Examples section below.

Figure 6:
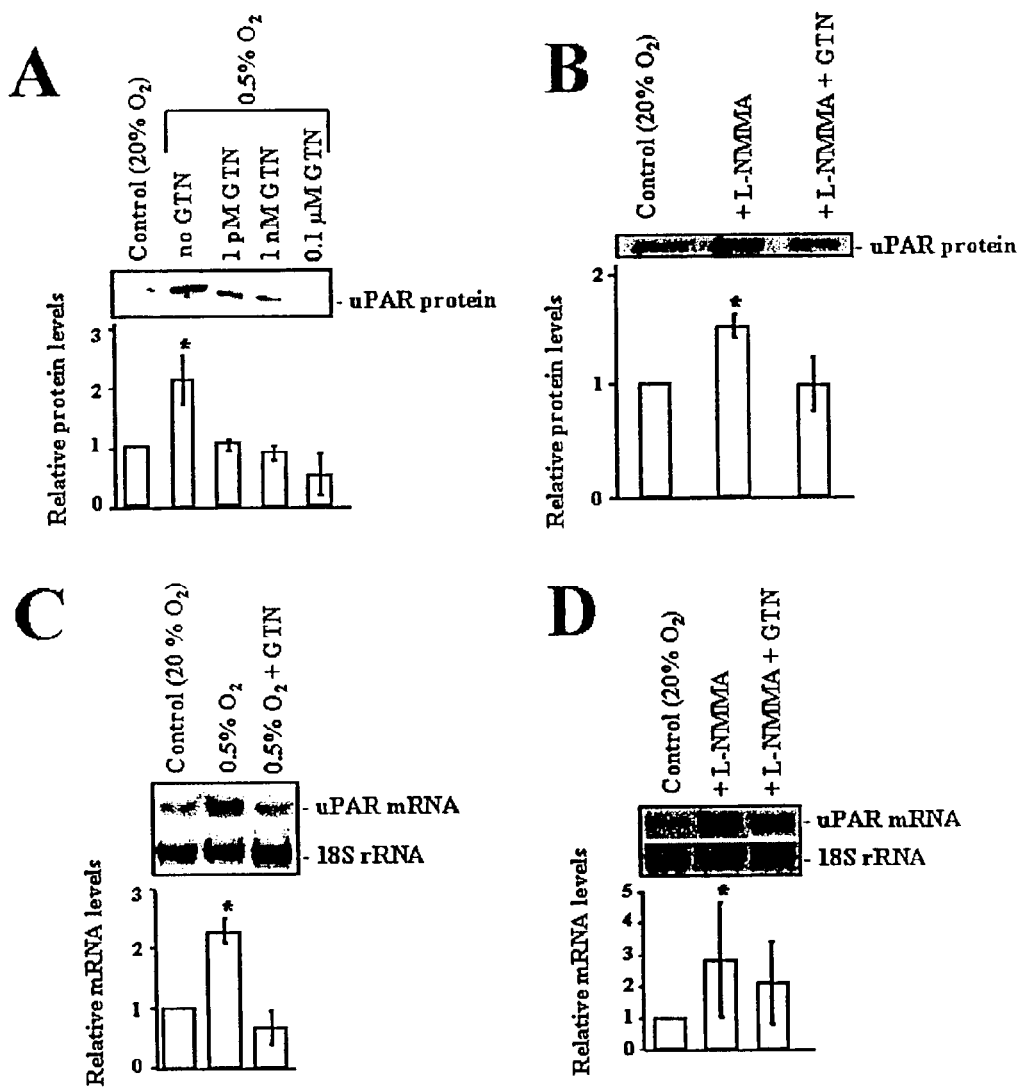

FIG. 6 illustrates urokinase plasminogen activator receptor (uPAR) expression in MDA-MB-231 breast cancer cells. Western blot analysis of uPAR protein expression by cells incubated in 1% $O_2$ in the presence of various concentrations of glyceryl trinitrate (GTN) (A; N=3) or in 20% $O_2$ in the absence or presence of the NOS antagonist N-monomethyl-L-arginine (L-NMMA, 0.5 µM) alone or in combination with GTN (0.1 nM) (B; N=6). The effect of GTN (1 pM) on uPAR mRNA levels was also examined by Northern blot analysis of cells cultured under conditions similar as for the Western blots (C and D; N=3 and 6 respectively). In all cases, GTN was added at the beginning of the 24-h incubation period. 18S rRNA was used to assess uniformity of RNA loading in the Northern blots. Bars represent means of relative densities±standard deviations. Asterisks (*) indicate statistically significant differences as compared to control (20% $O_2$) values. All P values are indicated in the Examples section below.

Figure 7:
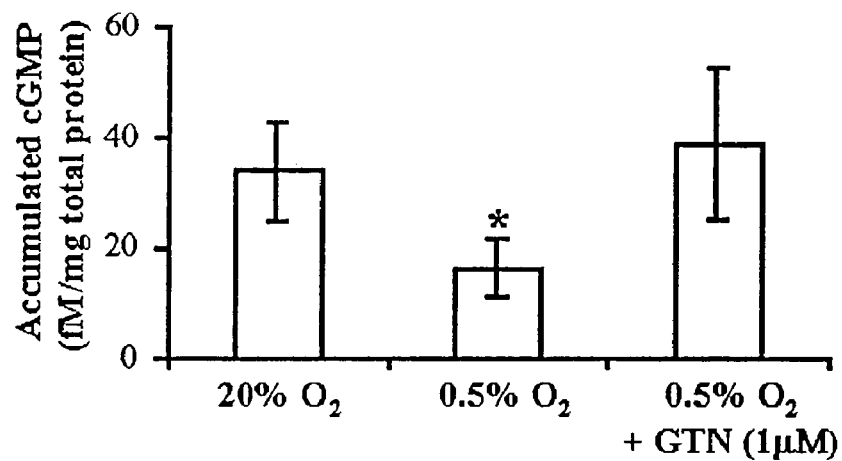
Figure 7:
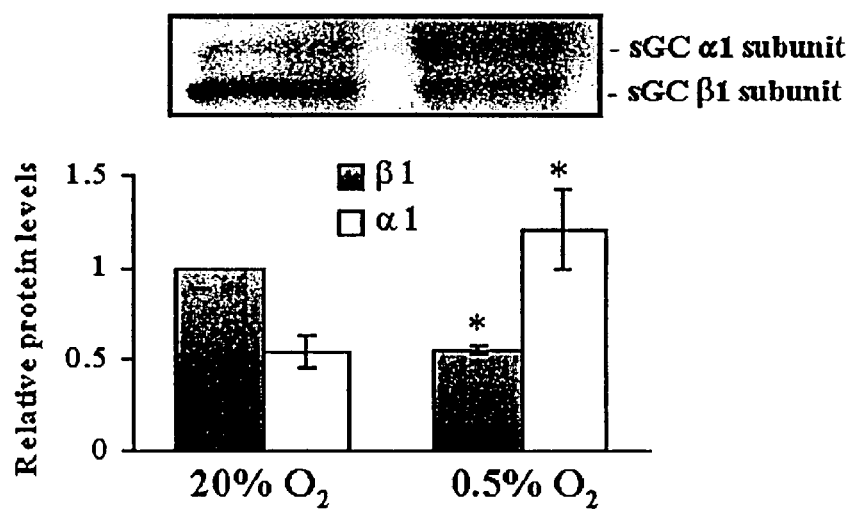

FIG. 7 illustrates the effect of hypoxia on sGC activity and expression in MDA-MB-231 breast carcinoma cells. (A) Total cellular cGMP accumulated in MDA-MB-231 breast carcinoma cells cultured for 6-h in 20% $O_2$ or 0.5% $O_2$ in the presence or absence of GTN (1 µM). Cyclic GMP levels were measured and normalized to total protein levels. Values represent the mean of accumulated cGMP±standard deviation (N=3). (B) Western blot analysis of sGC expression in cells incubated for 24 hours in 20% $O_2$ or 0.5% $O_2$ (N=3). Bars represent the mean densities±standard deviations. Asterisks (*) indicate statistically significant differences compared to control (20% $O_2$) density values. P values for each condition are indicated in the Examples section below.

Figure 8:
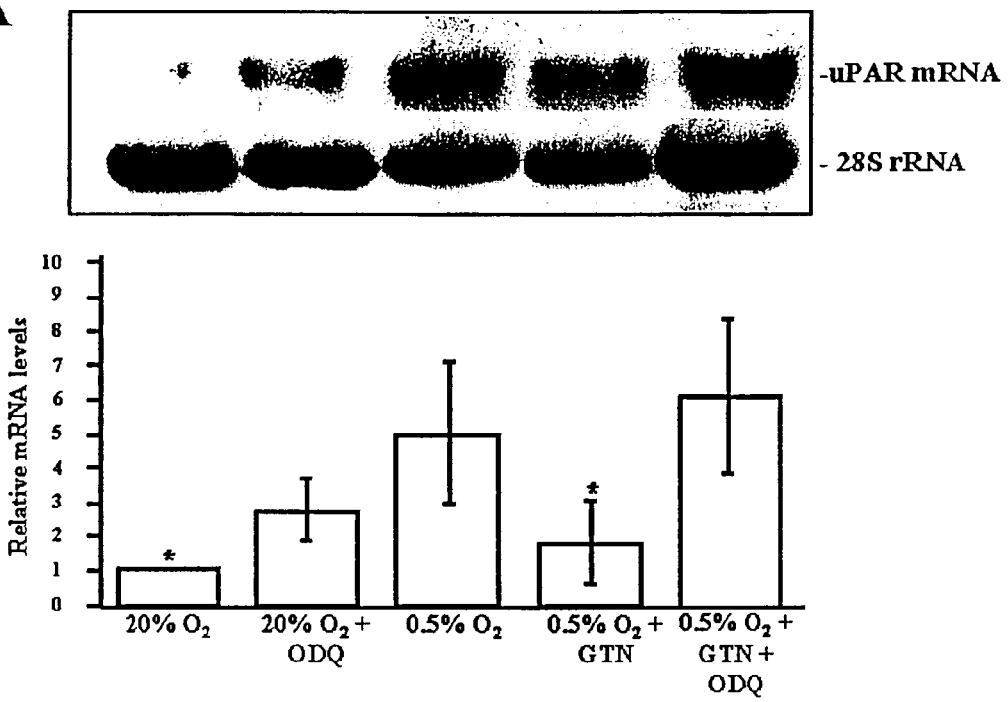
Figure 8:
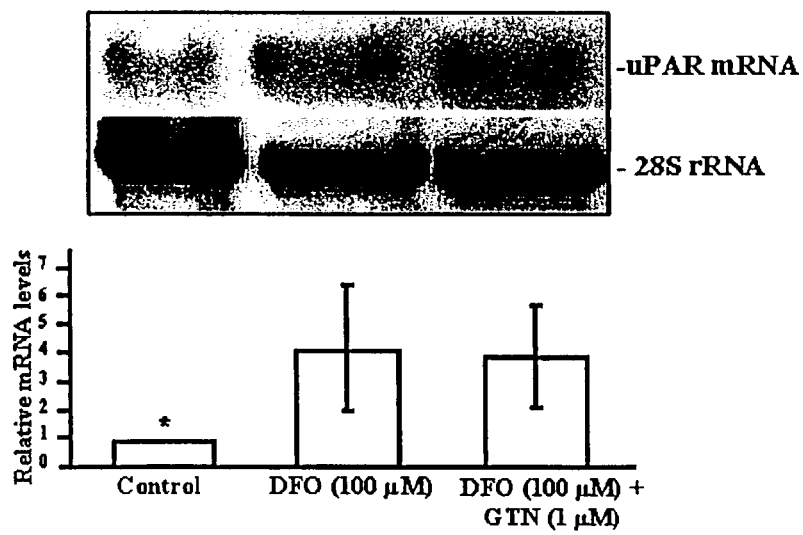

FIG. 8 illustrates the effect of sGC disruption on the NO-mediated inhibition of uPAR expression in MDA-MB-231 breast carcinoma cells. (A) Northern blot analysis of uPAR mRNA expression in cells cultured for 24 hours in 20% $O_2$ or 0.5% $O_2$, with or without GTN (1 µM) and the selective sGC inhibitor (ODG, 0.5 µM; N=5). (B) Northern blot analysis of uPAR expression in cells cultured for 24-h in the presence or absence of the heme disrupter DFO (100 mM), alone or in combination with GTN (1 µM) (N=5). Bars in both (A) and (B) represent mean relative densities±standard deviations. Values indicated by an asterisk (*) are significantly different. All P values are indicated in the Examples section below.

Figure 9:
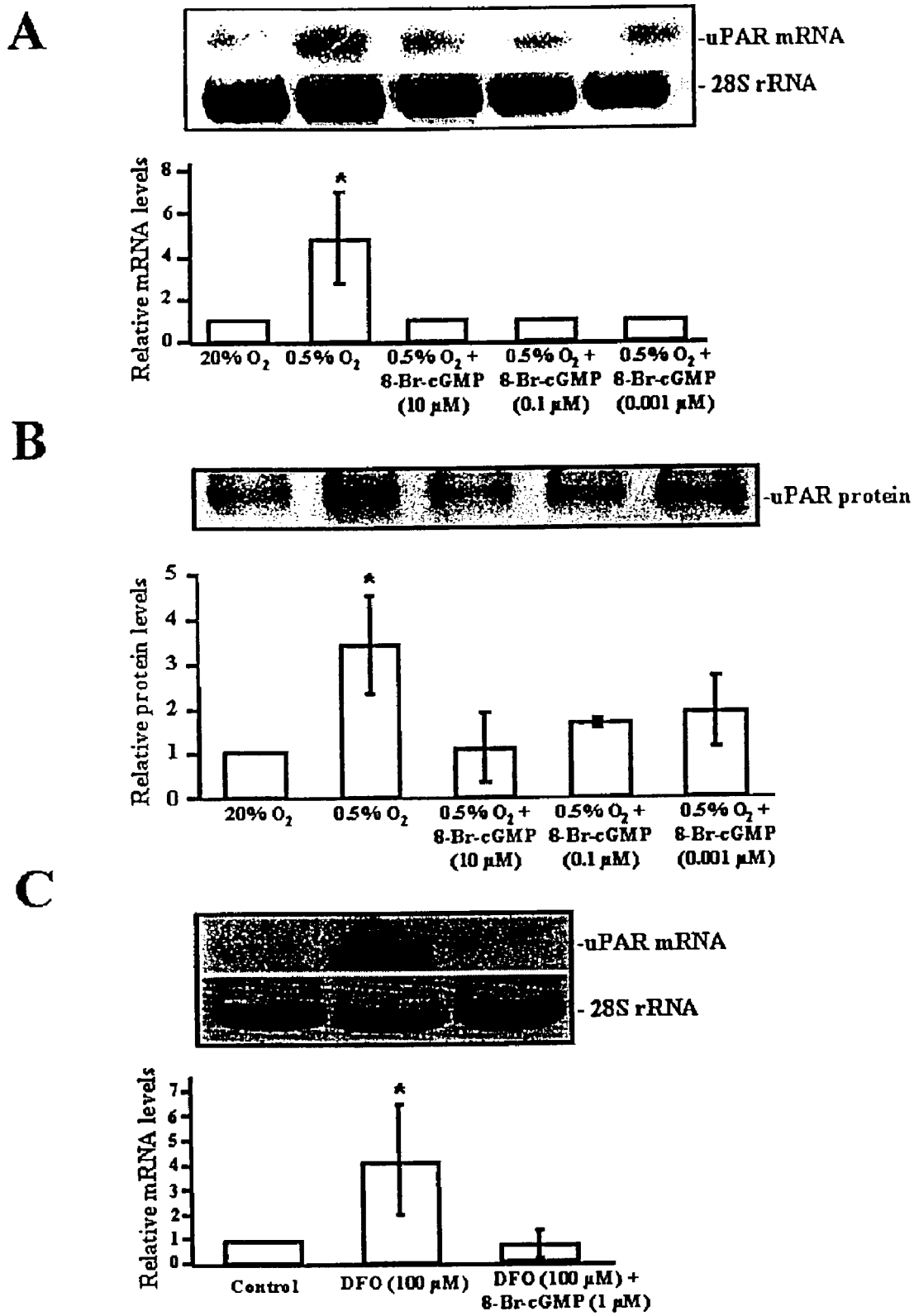

FIG. 9 illustrates the effect of 8-Br-cGMP on hypoxia- and DFO-induced uPAR expression in MDA-MB-231 breast carcinoma cells. (A) Northern blot analysis of uPAR expression in cells cultured for 24 hours in 20% $O_2$ or 0.5% $O_2$ in the absence or presence of various concentrations of 8-Br-cGMP (N=3). (B) Western blot analysis of uPAR protein in cells cultured for 24-h in 20% $O_2$ or 0.5% $O_2$ in the absence or presence of various concentrations of 8-Br-cGMP (N=9). (C) Northern blot analysis of uPAR transcript in cells cultured for 24-h in the absence or presence of DFO (100 µM) alone or with 8-Br-cGMP (1 µM) (N=6). Bars in (A), (B), and (C) represent mean relative densities±standard deviations. Values indicated by an asterisk (*) are significantly different from the control value (20% $O_2$). All P values are indicated in the Examples section below.

Figure 10:
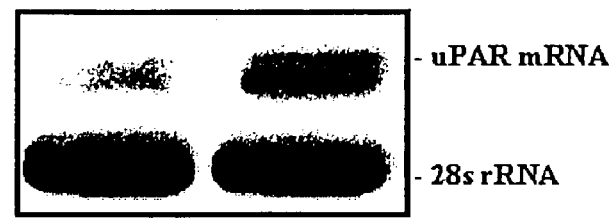
Figure 10:
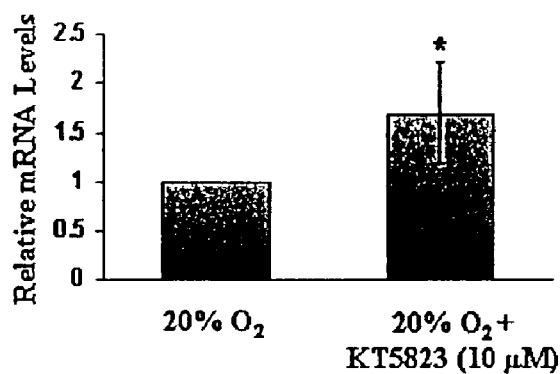
Figure 10:
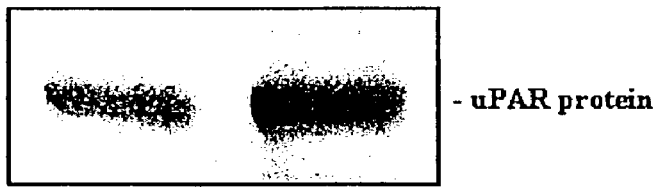
Figure 10:
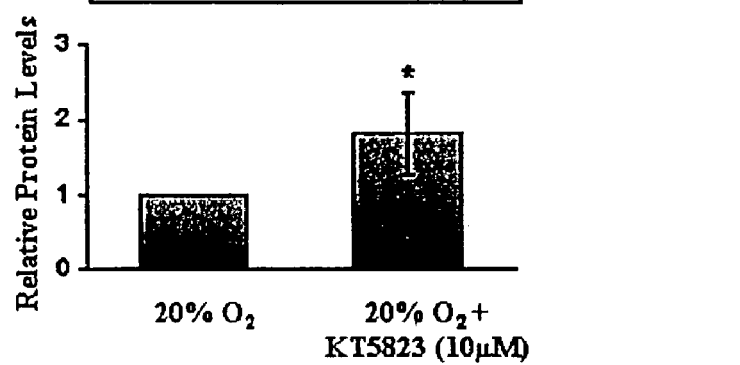

FIG. 10 illustrates the effect of PKG inhibition on uPAR expression in MDA-MB-231 breast carcinoma cells. (A) Northern blot analysis of uPAR expression in cells cultured for 6-h in the presence or absence of a PKG inhibitor (KT5823, 10 µM) (N=6). (B) Western blot analysis of uPAR protein levels in cells cultured for 6-h in the presence or absence of a PKG inhibitor (KT5823, 10 µM) (N=6). Bars represent mean relative density±standard deviation. Values indicated by an asterisk (*) are significantly different from the control value (20% $O_2$). All P values are indicated in the Examples section below.

Figure 11:
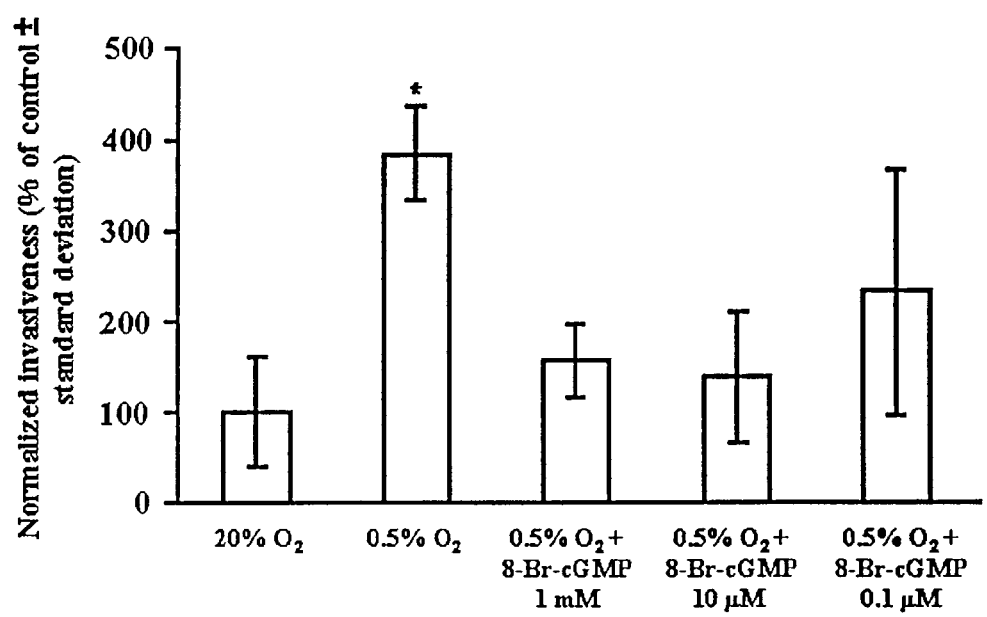

FIG. 11 illustrates the effect of 8-Br-cGMP on the hypoxic upregulation of the in vitro invasiveness of MDA-MB-231 breast carcinoma cells. Cells were allowed to invade through a reconstituted extracellular matrix for 24-h in 20% $O_2$ or 0.5% $O_2$ in the absence or presence of varying concentrations of 8-Br-cGMP. The invasion index for each treatment was calculated after counting the cells that penetrated through the membrane. Values are presented as the relative mean of the invasion indices±standard deviation. The value indicated by an asterisk (*) was significantly different from the invasion index of the control (20% $O_2$) cells (N=6). All P values are indicated in the Examples section below.

Figure 12:
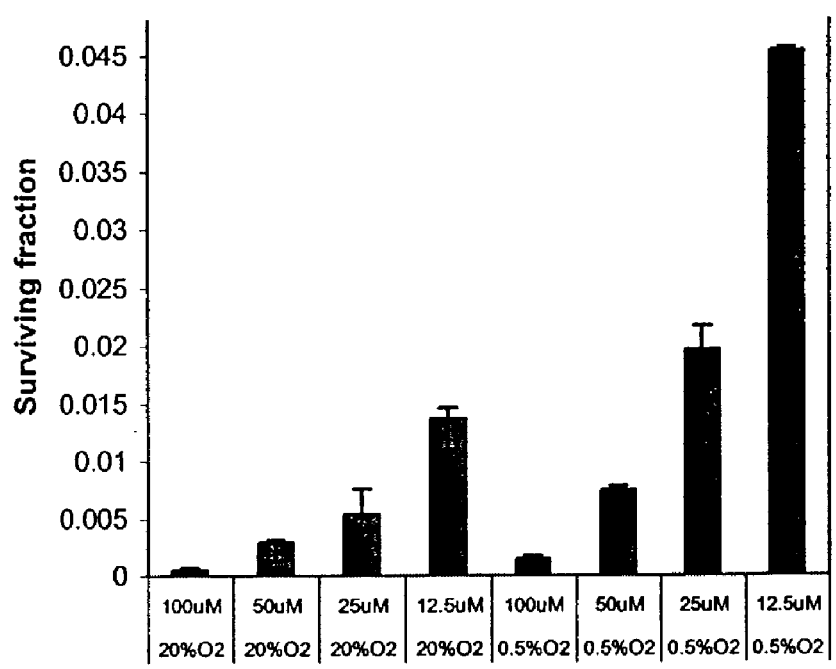

FIG. 12 illustrates the effect doxorubicin (12.5-100 µM) on survival of human PC-3 prostate cancer cells. Cells were pre-exposed to 20% or 0.5% $O_2$ for 24 h before a 1 hr treatment with doxorubicin. Survival was assessed by clonogenic ability.

Figure 13:
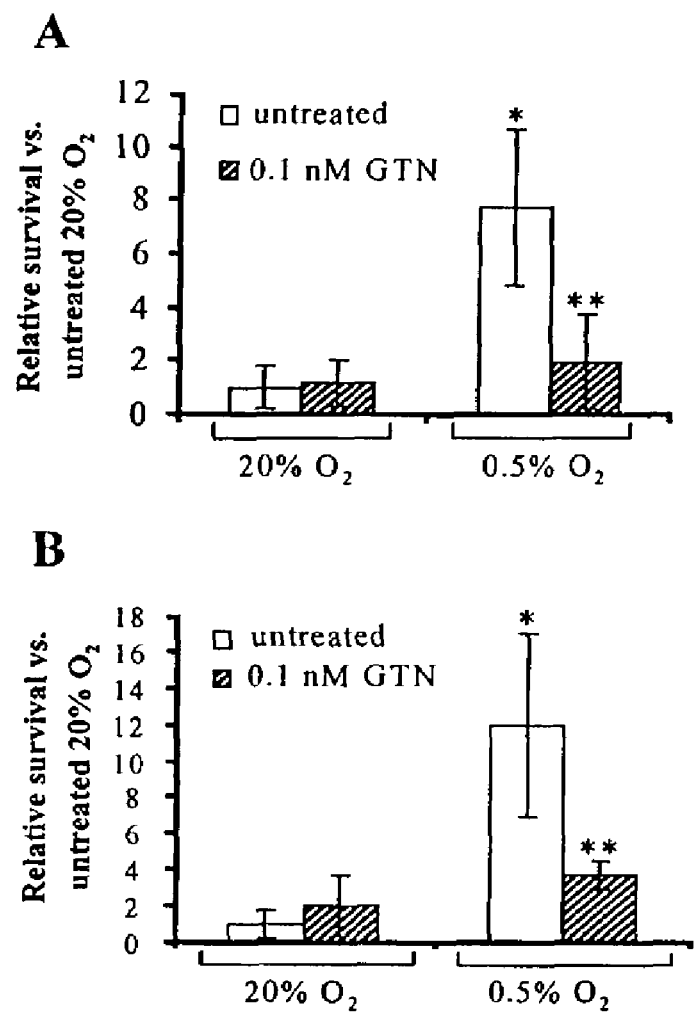

FIG. 13 illustrates the effect of a single dose of GTN on the hypoxia-induced resistance to doxorubicin. Treatment of (A) human PC-3 and (B) TRAMP-C2 cells with GTN (0.1 nM) prevented the acquisition of hypoxia-induced resistance to 12.5 µM doxorubicin over a 12 hour incubation in hypoxia. Results are presented as means±standard deviation (N=12). Single asterisk (*) indicates a statistically significant difference (P<0.0001) in survival compared with cells incubated in 20% $O_2$ at 12.5 µM doxorubicin. Double asterisk (**) indicates a statistically significant difference (P<0.0001) in survival compared with cells incubated in 0.5% $O_2$ alone.

Figure 14:
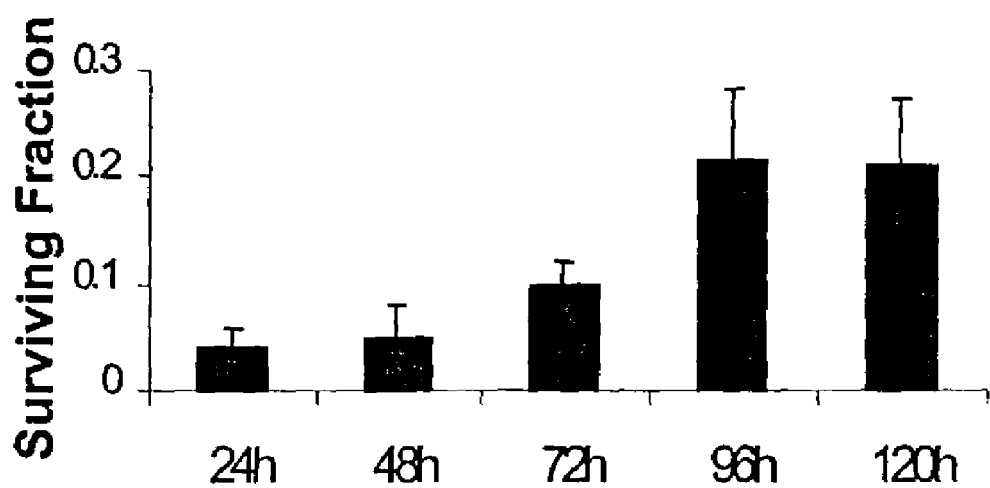

FIG. 14 illustrates the effect of MDA-MB-231 human breast carcinoma cell spheroid culture on resistance to doxorubicin over time. Following initial cell plating, spheroids formed for 24, 48, 72, 96 or 120 h. At each time point, spheroids were exposed to 200 µM of doxorubicin, then disaggregated and plated for assessment of colony formation (survival). At this concentration of doxorubicin, survival in monolayer culture was zero (not shown).

Figure 15:
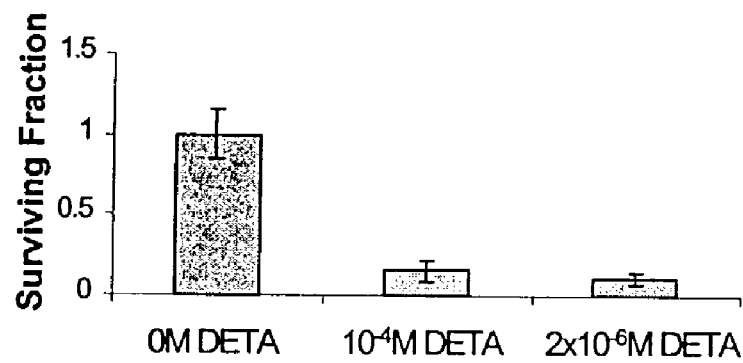

FIG. 15 illustrates the effect of 200 µM doxorubicin in combination with the NO donor drug DETA/NO on MDA-MB-231 breast carcinoma spheroid cell survival. Spheroids were allowed to form for 72 h. DETA/NO was applied for the final 24 h of spheroid formation. Spheroids were then exposed to doxorubicin for 1 h, prior to disaggregation and plating for assessment of survival by clonogenic assay.

Figure 16:
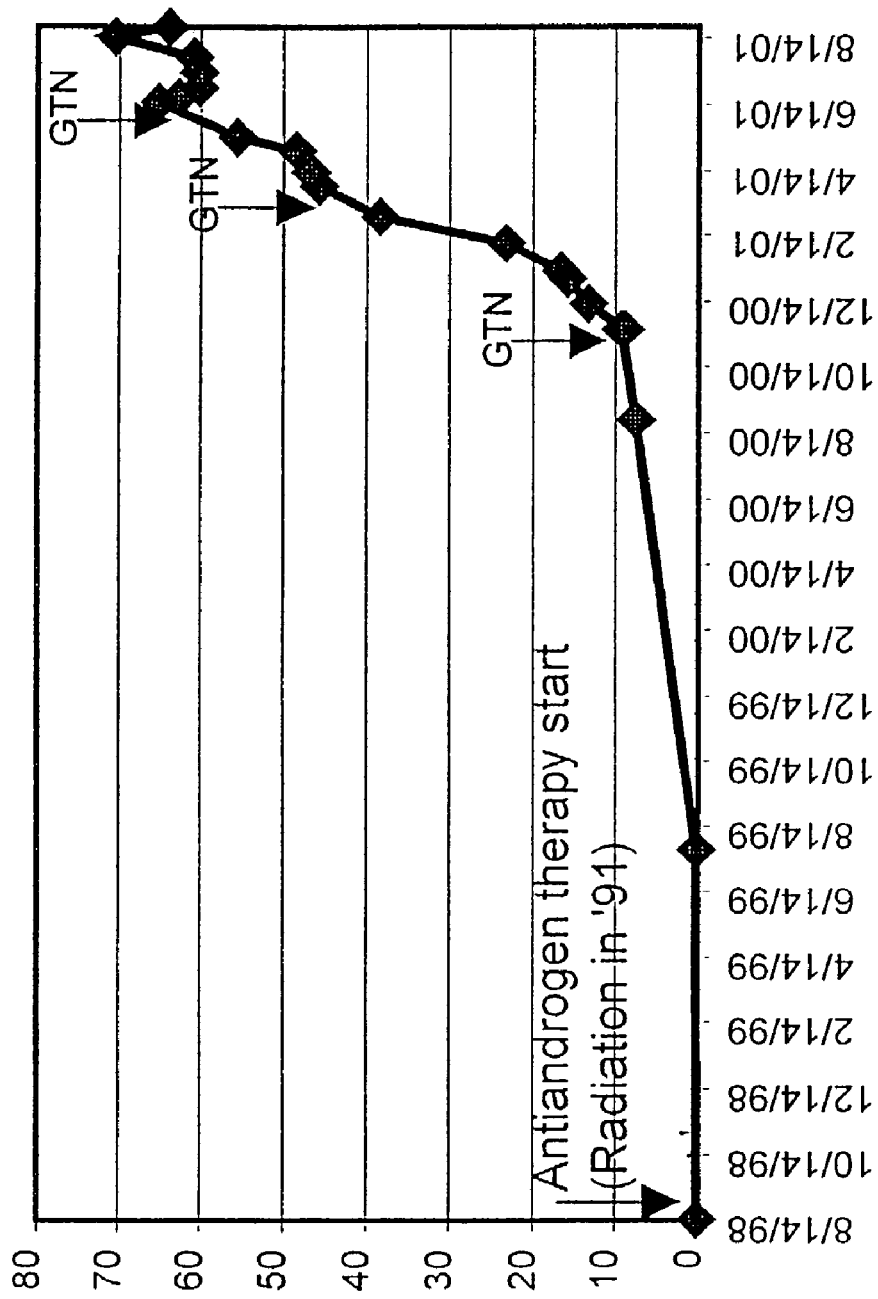

FIG. 16 illustrates the effect of GTN therapy on a patient with prostate cancer wherein the prostate is still intact. PSA levels in one patient with prostate cancer wherein the prostate is still intact are shown. This patient was administered three episodes of treatment, for approximately one month each, of GTN, 0.03 mg/hour, 24 hours a day. As shown, following commencement of the first two episodes, a decrease in the rate of increase in PSA levels was observed. Following commencement of the third episode, a decrease in PSA levels was observed.

Figure 17:
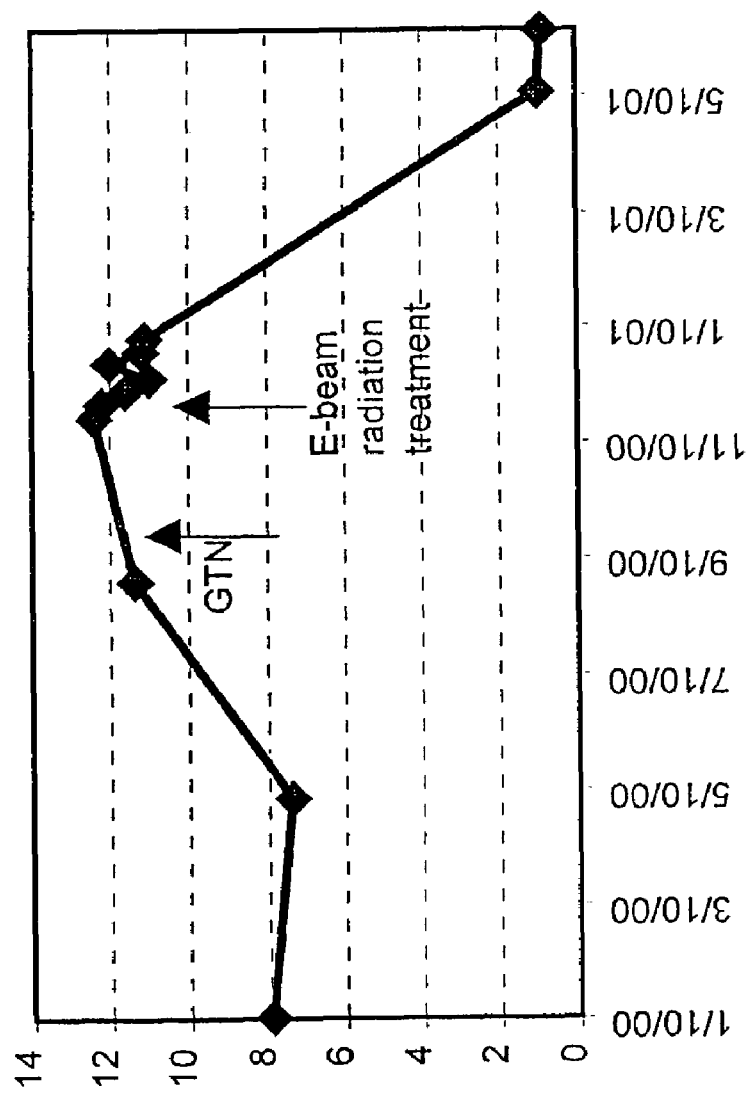

FIG. 17 illustrates the effect of GTN therapy in combination with radiation therapy. Circulating PSA levels in one patient with prostate cancer wherein the prostate is still intact are shown. This patient was administered GTN chronically, transdermally at a concentration of 0.03 mg/hour. Two months after chronic GTN therapy was begun, the patient was administered radiation therapy. As shown, this combination therapy accelerated the rate of PSA decrease to within three months. The expected average for a similar decrease in PSA levels following radiation therapy alone is twelve months.

DETAILED DESCRIPTION OF THE INVENTION

We have now demonstrated that the mechanism by which hypoxia and hyponitroxia have impact on cellular phenotypes is not mediated solely due to a lack of oxygen, but rather also from a deficiency in nitric oxide mimetic activity. Further, we have now demonstrated that administration of a low dose of a nitric oxide mimetic is sufficient to increase, restore or maintain levels of nitric oxide mimetic activity of cells so that a malignant cell phenotype is inhibited or prevented. This inhibition and prevention occurs even when the cells are in a hypoxic environment and/or when combined with inhibition of endogenous nitric oxide production. Nitric oxide mimetics are effective under normoxic conditions as well as hypoxic conditions. Administration of very low doses of nitric oxide mimetics, even under conditions of markedly reduced levels of oxygen (1% $O_2$), was able to prevent the generation of a malignant cell phenotype and inhibit a malignant cell phenotype of cells.

Accordingly, the present invention relates to the use of nitric oxide mimetic (e.g., low dose) therapy in inhibiting and preventing a malignant cell phenotype of cells. The methods and formulations of the present invention provide new therapeutic approaches for the treatment and prevention of cancer in animals. For purposes of the present invention, by "treatment" or "treating" it is meant to encompass all means for controlling cancer by reducing growth of cells exhibiting a malignant cell phenotype and improving response to antimalignant therapeutic modalities. Thus, by "treatment" or "treating" it is meant to inhibit the survival and/or growth of cells exhibiting a malignant cell phenotype, prevent the survival and/or growth of cells exhibiting a malignant cell phenotype, decrease the invasiveness of cells exhibiting a malignant cell phenotype, decrease the progression of cells exhibiting a malignant cell phenotype, decrease the metastases of cells exhibiting a malignant cell phenotype, increase the regression of cells exhibiting a malignant cell phenotype, and/or facilitate the killing of cells exhibiting a malignant cell phenotype. "Treatment" or "treating" is also meant to encompass maintenance of cells exhibiting a malignant cell phenotype in a dormant (or quiescent) state at their primary site as well as secondary sites. Further, by "treating or "treatment" it is meant to increase the efficacy as well as prevent or decrease resistance to antimalignant therapeutic modalities. By "antimalignant therapeutic modalities" it is meant to include, but is not limited to, radiation therapies, thermal therapies, immunotherapies, hormone therapies, single agent chemotherapies, combination chemotherapies, chemo-irradiation therapies, adjuvant therapies, neo-adjuvant therapies, palliative therapies, and other therapies used by those of skill in the art in the treatment of cancer and other malignancies. "Treating" or "treatment" is also meant to encompass prolonged cancer remission, prevention of recurrence, decrease of cancer markers, reduction in cancer volume, reduction of pain, discomfort, and disability (morbidity), increase in quality of life associated with antimalignant therapeutic modalities, a decrease in mucositis, and a reduction in the need for anti-emetic agents and narcotic pain killers. By "increasing the efficacy", it is meant to include an increase in potency and/or activity of the antimalignant therapeutic modality and/or a decrease in the development of resistance to the antimalignant therapeutic modality, and/or an increase in sensitivity of the malignant cells and/or tumor to the antimalignant therapeutic modality.

The present invention also relates to methods of monitoring and/or diagnosing malignant cell phenotypes in an animal via measurement of tumor selective markers in an animal in the presence of NO mimetic (e.g. low dose) therapy. Exemplary tumor markers useful in the monitoring and diagnosing of tumor progression and metastases include, but are not limited to, prostate specific antigen (PSA) for prostate cancer, carcinoembryonic antigen (CEA) and polypeptides such as gastrin and glucagon for gastrointestinal cancer, α-fetoprotein (AFP) and βhCG for testicular cancer, α-fetoprotein (AFP), human chorionic gonadotrophin (HCG) and lactate hydroginase (LDH) in germ cell cancers, HCG in choriocarcinoma, serum AFP in hepatocellular carcinoma, neuron-specific enolase (NSE) in small-cell lung cancer, paraprotein levels and B2-microglobulin which may be of prognostic value in myeloma, 5-hydroxyindole acetic acid (5HIAA) urine levels in carcinoid tumors, squamous cell carcinoma antigen (SCC) and cytokeratin fragments for squamous cell carcinoma, SCC and CA 125 for prognostic information in cervical carcinoma, CA19-9 and CA72-4 for gastric cancer, CD 24 for various cancers, including p-selectin ligand in non-small cell lung cancer, NFκB for prostate cancer prognosis, serum tumor marker CA125 for ovarian cancer, CDKN2A deletion as a diagnostic marker for malignant mesothelioma, dysadherin overexpression in pancreatic ductal adenocarcinoma, SMAD7 as a prognostic marker in patients with colorectal cancer, TGFβ1 as a potential prognostic marker for breast cancer patients with advanced disease, neuroendocrine and cytokeratin serum markers as prognostic determinants of small cell lung cancer, ErbB2 and bone sialoprotein as markers for metastatic osteosarcoma cells, cyclin E and CA15-3 for breast cancer and the cell surface receptors for estrogen and Her-2 for breast cancer. Additional markers which can be monitored for diagnostic purposes include, but are not limited to, calcitonin and calcitonin-related peptide for diagnosis and screening of medullary thyroid carcinoma, Protein Regulated by OXYgen-1 (PROXY-1), also known as NDRG-1, plasminogen activator inhibitor (PAI-1), urokinase-type plasminogen activator receptor (uPAR) and vascular endothelial growth factor (VEGF). Further, as will be understood by those of skill in the art upon reading this disclosure, additional tumor markers to those exemplified herein can also be monitored in the present invention. In a preferred embodiment, the tumor marker is detectable in a biological fluid such a serum, plasma or urine. No change, a decrease or deceleration in the increase of the level of one or more of these markers in an animal following administration of a low dose nitric oxide mimetic as compared to the level of the marker in the animal prior to administration of the low dose nitric oxide mimetic is indicative of a malignant cell phenotype in the animal.

For purposes of the present invention by the term "low dose" it is meant an amount of nitric oxide mimetic which is capable of increasing, restoring or maintaining a level of nitric oxide mimetic activity to cells, tumors and/or diseases which inhibits or prevents malignant cell phenotypes and/or which increases efficacy of an antimalignant therapeutic modality co-administered with the low dose NO mimetic. At this low dose, the known untoward effects of NO mimetics in animals without a malignant cell phenotype, cell, tumor and/or disease do not occur. As will be understood by those of skill in the art upon reading this disclosure, the nitric oxide mimetic increases, restores or maintains activity both in and around the cell (i.e. in the cellular microenvironment).

Methods for determining levels of nitric oxide of cells based upon nitrite, nitrate and S-nitrosothiol levels in cell culture, as well as plasma and serum, have been described. Serum or plasma nitrate levels in healthy normal volunteers have been reported to show a mean nitric oxide level of $33.4\pm8.9$ μM with a range of 14 to 60 μM (Marzinzig et al. Nitric Oxide: Biology and Chemistry 1987 1(2): 177-189). These levels, however, are based on NO synthase end products, which accumulate and thus are likely to represent an overestimate of normal physiologic nitric oxide levels. Reported measured levels also vary depending upon the method selected for measurement. Further, levels of nitrite and nitrate in the plasma or serum are not solely representative of a patient's NO production. Based upon our experiments, we believe that normal physiologic levels of nitric oxide mimetic activity of cells may be lower, for example at least 5-fold, and preferably 10- to 10,000-fold lower, than those reported in the art, depending upon the cell.

Short-term nitric oxide mimetic therapy is generally administered at levels which increase nitric oxide mimetic activity of cells above normal physiologic levels. For purposes of the present invention, however, wherein longer-term therapy is generally desired, induction of tolerance against the NO mimetic and side effects become concerns. Thus, in certain aspects, the amount of nitric oxide mimetic administered is preferably very low so as to delay and/or reduce development of tolerance to the administered NO mimetic and/or unwanted side effects. For example, it is known that administration of nitric oxide or compounds which deliver nitric oxide to human beings at doses conventionally employed to treat cardiovascular conditions (i.e. GTN at 0.2 mg/h or greater) by vasodilation can provoke powerful vasodilator responses as well as development of drug tolerance against GTN upon repeated administration. Such administration is often accompanied by a number of undesirable side effects including headache, flushing and hypotension. In contrast, preferred doses of nitric oxide mimetic administered in the present invention to inhibit and prevent a malignant cell phenotype, cell, tumor and/or disease are lower, preferably at least 3 to 10,000-fold lower, more preferably at least 100- to at least 10,000-fold lower than those typically used in other therapeutic applications such as vasodilation and thus do not induce tolerance to the NO mimetic as quickly nor undesirable side effects. For example, using the nitric oxide mimetics sodium nitroprusside (SNP) and glyceryl trinitrate (GTN), we have now demonstrated that amounts ranging between $10^{-12}$ and $10^{-10}$ M in the cellular environment can be used to prevent and inhibit a malignant cell phenotype, cell, tumor and/or disease. Further, based on results from these experiments, we believe that doses of SNP as low as $10^{-14}$ M would be effective in preventing and inhibiting a malignant cell phenotype, cell, tumor and/or disease in less hypoxic or hyponitroxic environments. Table 1 provides additional examples of various lower preferred doses for nitric oxide mimetics useful in the present invention as well as the comparative higher doses used in vasodilation therapy.

As will be understood by those of skill in the art upon reading this disclosure, lower or higher amounts of nitric oxide mimetics than those exemplified herein can also be administered based upon the efficacy of the nitric oxide mimetic in achieving the ultimate goal of increasing, restoring or maintaining nitric oxide mimetic activity of cells so that a malignant phenotype is prevented or inhibited without substantial drug tolerance to the NO mimetic developing and without unwanted side effects. Determining amounts of nitric oxide mimetic to be incorporated into the low dose formulations of the present invention can be performed routinely by those skilled in the art based upon the teachings provided herein.

By the phrase "inhibiting and preventing" as used herein, it is meant to reduce, reverse or alleviate, ameliorate, normalize, control or manage a biological condition. Thus, inhibiting and preventing a malignant cell phenotype in accordance with the present invention refers to preventing development, reversing or ameliorating development and/or normalizing, controlling or managing development of a malignant cell phenotype, cell, tumor and/or disease. Additionally inhibiting and preventing a malignant tumor in accordance with the present invention refers to preventing development, reversing or ameliorating development and/or normalizing, controlling or managing development of a malignant tumor. Similarly, inhibiting and preventing a malignant disease in accordance with the present invention refers to preventing development, reversing the ameliorating development and/or normalizing, controlling or managing development of a malignant disease. Accordingly, administration of a low dose of a nitric oxide mimetic can be used both (1) prophylactically to inhibit and prevent a malignant cell phenotype, cell, tumor and/or disease from developing in animals at high risk for developing cancer or exposed to a factor known to decrease nitric oxide mimetic activity of cells, and (2) to treat cancer in animals by inhibiting metastases and development of resistance to antimalignant therapeutic modalities and increasing the efficacy of antimalignant therapeutic modalities. According to Stedman's Medical Dictionary, malignant is defined as 1) Resistant to treatment; occurring in severe form, and frequently fatal; tending to become worse and lead to an ingravescent course; and 2) in reference to a neoplasm, having the property of locally invasive and destructive growth and metastasis. In accordance with this definition, for purposes of the present invention, by "malignant cell phenotype" it is meant to encompass increases in metastasis, resistance to antimalignant therapeutic modalities, and angiogenesis. By "malignant cell phenotype, cell, tumor and/or disease" for purposes of the present invention, it is also meant to be inclusive of conditions in the spectrum leading to malignant behavior and abnormal invasiveness such as hyperplasia, hypertrophy and dysplasia, as well as those cells and tissue that facilitate the malignant process. Examples of conditions in this spectrum include, but are not limited to, benign prostatic hyperplasia and molar pregnancy. As evidenced by data presented herein, inhibition and prevention of a malignant cell phenotype in cells, tumors and/or diseases can be routinely determined by examining expression of genes including, but not limited to, uPAR, PSA, PAI-1, PROXY-1 and VEGF, by examining cell invasiveness in in vitro or in vivo assays and/or by examining resistance of the cells to antimalignant therapeutic modalities. It is believed that elevated phosphodiesterase expression and/or activity may be observed in cells with a malignant cell phenotype. Methods for measuring expression of these genes have been described for example in WO 99/57306, which is herein incorporated by reference. As will be understood by those of skill in the art upon reading this disclosure, however, other methods for determining gene expression via measurement of expressed protein or proteolytic fragments thereof can also be used. For purposes of the present invention, by the term "nitric oxide mimetic" it is meant nitric oxide, or a functional equivalent thereof; any compound which mimics the effects of nitric oxide, generates or releases nitric oxide through biotransformation, generates nitric oxide spontaneously, or spontaneously releases nitric oxide; any compound which in any other manner generates nitric oxide or a nitric oxide-like moiety or activates other stages of the NO pathway; or any compound which enables or facilitates NO utilization by the cell, when administered to an animal. Such compounds can also be referred to as "NO donors", "NO prodrugs", "NO producing agents", NO delivering compounds", "NO generating agents", NO releasing agents, and "NO providers". Examples of such compounds include, but are not limited to: organonitrates such as nitroglycerin (GTN), isosorbide 5-mononitrate (ISMN), isosorbide dinitrate (ISDN), pentaerythritol tetranitrate (PETN), erythrityl tetranitrate (ETN); amino acid derivatives such as N-hydroxyl-L-arginine (NOHA), $N^6$-(1-iminoethyl)lysine (L-NIL), L-$N^5$-(1-iminoethyl)ornithine (LN-NIO), $N^\omega$-methyl-L-arginine (L-NMMA), and S-nitrosoglutathione (SNOG).

NO prednisone and other compounds which generate or release NO under physiologic conditions such as S,S-dinitrosodithiol (SSDD), [N-[2-(nitroxyethyl)]-3-pyridinecarboxamide (nicorandil), sodium nitroprusside (SNP), S-nitroso-N-acetylpenicilamine (SNAP), 3-morpholino-sydnonimine (SIN-1), molsidomine, DEA-NONOate(2-(N, N-diethylamino)-diazenolate-2-oxide), and spermine NONOate (N-[4-[1-(3-aminopropyl)-2-hydroxy-2-nitrosohydrazino]butyl-1,3-propanediamine). Organic nitrates GTN, ISMN, ISDN, ETN, and PETN, as well as nicorandil (commonly known as a potassium channel opener) are commercially available in pharmaceutical dosage forms. SIN-1, SNAP, S-thioglutathione, L-NMMA, L-NIL, L-NIO, spermine NONOate, and DEA-NONOate are commercially available from Biotium, Inc. Richmond, Calif. As used herein the term "nitric oxide mimetic" is also intended to mean any compound which acts as a nitric oxide pathway mimetic, that has nitric oxide-like activity, or that mimics the effect of nitric oxide. Such compounds may not necessarily release, generate or provide nitric oxide, but they have a similar effect to nitric oxide on a pathway that is affected by nitric oxide. For example, nitric oxide has both cyclic GMP-dependent and cyclic GMP-independent effects. Nitric oxide is known to activate the soluble form of guanylyl cyclase thereby increasing intracellular levels of the second messenger cyclic GMP and other interactions with other intracellular second messengers such as cyclic AMP. As such, compounds which directly activate either particulate or soluble guanylyl cyclase such as natriuretic peptides (ANP, BNP, and CNP), 3-(5'-hydroxym-

TABLE 1

Typical Vasodilatory and Low Doses of Organonitrate

| Compound | Commercial Product | Vasodilatory Dose | Preferred Dose According to the Present Invention |
|---|---|---|---|
| Nitroglycerin (sublingual tablets) | Nitrostat ® (Parke-Davis); 0.3 mg, 0.4 mg and 0.6 mg sublingual tablets | Dissolve one tablet (0.3-0.6 mg) sublingually or in the buccal pouch at the first sign of an acute anginal attack | Dissolve one tablet containing from about 0.02 µg to about 0.1 mg sublingually or in the buccal pouch |
| Nitroglycerin (lingual aerosol) | Nitrolingual ® Spray (Rhone-Poulenc Rorer); metered aerosol, 0.4 mg/metered dose | One or two metered doses (0.4-0.8 mg) sprayed onto or under the tongue at the onset of an anginal attack | About 0.02 µg to about 0.1 mg sprayed onto or under the tongue |
| Nitroglycerin (transdermal patch) | Minitran ® (3M Corporation); Transdermal patches having the following characteristics (size (cm²), delivery rate (mg/h)); (3.3, 0.1; 6.7, 0.2; 13.3, 0.4; and 20.0, 0.6) | Suggested dose is between 0.2-0.8 mg/h for 12-14 h daily with a minimum nitrate-free interval of 10-12 h | About 0.0125 µg/hr-0.1 mg/h |
| Nitroglycerin (ointment) | NITRO-BID ® Ointment (Hoechst Marion Roussel); lactose and 2% nitroglycerin in a base of lanolin and white petrolatum. Each inch (2.5 cm), as squeezed from the tube, contains approximately 15 mg of nitroglycerin | Doses used in clinical trials have ranged from ½ inch (1.3 cm; 7.5 mg), to 2 inches (5.1 cm; 30 mg), typically applied to 36 square inches (232 square cm) of skin on the arms or legs | Ointment containing about 0.375 µg to about 3.75 mg of nitroglycerin applied to the arms or legs over an area of about 36 square inches (232 cm²) |
| Isosorbide 5-mononitrate | IMSO ® (Wyeth-Ayerst) 20 mg tablets | 20 mg twice daily | About 1 µg to about 2.5 mg twice daily |
| Erythrityl tetranitrate | Cardilate ® (Burroughs-Wellcome); oral/sublingual tablets, 5 mg, 10 mg | Chronic (Adults): 10 mg orally 4 times daily, gradually increased to 20 mg, if necessary, not to exceed 100 mg/day. | Chronic (Adults): About 0.5 µg to about 1.25 mg orally 4 times daily, gradually increased to about 1 µg to about 2.5 mg/day, if necessary, not to exceed about 5 to about 12.5 mg/day |
| Sodium nitroprusside | Nipride ® (Roche); Nitropress ® (Abbott); intravenous solution | Slow infusion at a rate of 0.5 µg/kg/mn of a solution of 50 mg in 500-1000 mL of 5% dextrose up to a limit of 3.5 mg/kg in brief infusions | Slow infusion at a rate of from 0.025 ng/kg/min to about 0.063 µg/kg/min of a solution of 50 mg in 500-1000 mL of 5% dextrose up to a limit of about 0.18 mg/kg to about 0.44 mg/kg in brief infusions |
| Molsidomine | Corvaton ® (Hoechst Marion Roussel); 2 mg, 4 mg, and 6 mg tablets | 2 mg/day up to 36 mg/day given in separate doses either twice or three times daily | 0.1 µg/day up to 4.5 mg/day given in separate doses either twice or three times daily |
| Nicorandil | Nicorandil ® (Chugai Pharmaceuticals, Japan), Dancor ® (Merck) 10 mg, 20 mg tablets | For the treatment of angina 10-20 mg twice daily | About 0.5 µg to about 1 mg twice daily | ethyl-2'furyl)-1-benzyl indazole (YC-cGMP or YC-1) and 8-(4-chlorophenylthio) guanosine 3',5'-cyclic monophosphate (8-PCPT-cGMP), are also examples of NO-mimetics. In some embodiments of the present invention, however, it is preferred that the NO-mimetic not encompass a compound which directly activates either particulate or soluble guanylyl cyclase. Nitric oxide mimetic activity encompasses those signal transduction processes or pathways which comprise at least one NO mimetic-binding effector molecule, such as for example, guanylyl cyclase and other heme containing proteins. Examples of agents which function as NO mimetics by enabling or facilitating NO utilization by the cell are compounds which inhibit phosphodiesterase activity and/or expression, such as phosphodiesterase inhibitors.

In a preferred embodiment of the present invention, more than one NO mimetic is administered. In this embodiment, it is preferred that the NO mimetics target or act upon different parts of the NO pathway of the cell. For example, an NO donor can be co-administered with a compound that inhibits cyclic nucleotide (e.g. cAMP or cGMP) degradation such as a phosphodiesterase inhibitor. Preferred phosphodiesterase (PDE) inhibitors useful as NO mimetics are those inhibiting PDE-1 through PDE-11.

By the term "hyponitroxia" in the present invention, it is meant conditions where levels of nitric oxide mimetic activity are lower than normal physiologic levels for that cell type.

Certain compounds suitable for use in the present invention are well known in the art and are described, e.g., in Goodman and Gilman, *The Pharmacological Basis of Therapeutics* (9th Ed.), McGraw-Hill, Inc. (1996); *The Merck Index* (12th Ed.), Merck & Co., Inc. (1996); *The Physician's Desk Reference* (49th Ed.), Medical Economics (1995); and *Drug Facts and Comparisons*, Facts and Comparisons (1993).

NO Donors

In preferred embodiments, the compounds of the present invention are NO donors. The nitric oxide donor can be any of a variety of NO donors including, for example, organic NO donors, inorganic NO donors and prodrug forms of NO donors. Additional suitable NO donors include compounds that can be metabolized in vivo into a compound which delivers nitric oxide (e.g., a prodrug form of a NO donor; a NO-releasing drug such as a NO-releasing non-steroidal anti-inflammatory drug (NO-NSAIDs), examples of which include nitro-aspirin, NCX 4016, nitro-(flurbiprofen), HCT 1026, NCX 2216; or a binary NO generating system, such as acidified nitrates; or compounds that serve as physiological precursor of nitric oxide, such as L-arginine and salts of L-arginine. The NO donor may include at least one organic nitrate (including esters of nitric acid) and can be either a cyclic or acyclic compound. For example, suitable NO donors include nitroglycerin (NTG), isosorbide dinitrate (ISDN), isosorbide mononitrate (ISMN) which may include isosorbide-2-mononitrate (IS2N) and/or isosorbide-5-mononitrate (IS5N), erythrityl tetranitrate (ETN), pentaerythritol tetranitrate (PETN), ethylene glycol dinitrate, isopropyl nitrate, glyceryl-1-mononitrate; glyceryl-1,2-dinitrate, glyceryl-1,3-dinitrate, butane-1,2,4-triol trinitrate, and the like. Nitroglycerin and other organic nitrates including ISDN, ETN, and PETN, have been given regulatory approval for use in treatments in other fields of medicine on human subjects. Additional NO donors include sodium nitroprusside, N,O-di-acetyl-N-hydroxy-4-chlorobenzenesulfonamide, $N^G$-hydroxy-L-arginine (NOHA), hydroxyguanidine sulfate, molsidomine, 3-morpholinosydnonimine (SIN-1), (±)-S-nitroso-N-acetylpenicillamine (SNAP), S-nitrosoglutathione (GSNO), (±)-(E)-ethyl-2-[(E)-hydroxyimino]-5-nitro-3-hexeneamide (FK409), (±)-N-[(E)-4-ethyl-3-[(Z)-hydroxy-imino]-5-nitro-3-hexen-1-yl]-3-pyridinecarboxamide (FR144420), and 4-hydroxymethyl-3-furoxancarboxamide. In addition, compounds that interfere with the breakdown of NO in vivo may be administered.

Additional NO Mimetics

In certain embodiments, the compounds and methods of the present invention are not limited to the foregoing traditional nitric oxide mimetics. As explained in detail below, these nitric oxide mimetics compounds include, for example, calcium channel blockers, α-adrenergic receptor antagonists and β-adrenergic receptor agonists, phosphodiesterase inhibitors, cAMP-dependent protein kinase activators, superoxide scavengers, potassium channel activators, benzodiazepines, adrenergic nerve inhibitors, antidiarrheal agents, HMG-CoA reductase inhibitors, adenosine receptor modulators, adenylyl cyclase activators, endothelin receptor antagonists, bisphosphonates, cGMP-dependent protein kinase activators, guanylyl cylase activators and SOC inhibitors. In certain aspects, the compounds are not limited to a low dose. Although a low dose can of course be used, the dosing of these compounds is not so limited. The compounds set forth below (e.g., PDE inhibitors) can be used at various doses such as high and low doses.

Calcium Channel Blockers $Ca^{2+}$ channel blockers are compounds that inhibit the entry of $Ca^{2+}$ into the cell from the extracellular fluid. Suitable $Ca^{2+}$ channel blockers for use with the methods of the present invention include, but are not limited to, nifedipine, nimodipine, felopidine, nicardipine, isradipine, amlodipine, diltiazem, bepridil, verapamil etc. (see, e.g., WO 98/36733). L-type $Ca^{2+}$ channel blockers are also available.

α-Adrenergic Receptor Antagonists and β-Adrenergic Receptor Agonists

Additional preferred compounds for use in the context of the present invention include, e.g., α-adrenergic receptor antagonists and β-adrenergic receptor agonists. Suitable α-adrenergic receptor antagonists include, for example, $α_1$-adrenergic receptor antagonists, $α_2$-adrenergic receptor antagonists and other nonspecific α-adrenergic receptor antagonists. Preferred $α_1$-adrenergic receptor antagonists include, but are not limited to, prazosin, doxazosin, phenoxybenzamine, phentolamine, terazosin, tolazoline, etc., and are described in Goodman and Gilman, "*The Pharmaceutical Basis of Therapeutics,*" 9th Edition, Hardman, et al. (ed.), McGraw-Hill (1996). Suitable $α_2$-adrenergic receptor antagonists include, but are not limited to, yohimbine and are also described in Goodman and Gilman, "*The Pharmaceutical Basis of Therapeutics,*" 9th Edition, Hardman, et al. (ed.), McGraw-Hill (1996). Other suitable antagonists are $α_2$-adrenergic antagonists include, for example, post-synaptic $α_2$-adrenergic antagonists. These post-synaptic $α_2$-adrenergic antagonists include, but are not limited to, imiloxan, ARC 239 dihydrochloride and other pharmaceutically acceptable salts thereof. ARC 239 dihydrochloride is 2-[2-(4-(2-Methoxyphenyl)piperazin-1-yl)ethyl]-4,4-dimethyl-1,3-(2H,4H)-isoquinolindone dihydrochloride. Other suitable post-synaptic $α_2$-adrenergic antagonists include, but are not limited to, idazoxan, rauwolscine, efaroxan, mianserin, and mirtazapine. Of these, mianserin and mirtazapine are particularly preferred. Suitable β-adrenergic receptor agonists for use with the methods of the present invention include, but are not limited to, $β_1$-adrenergic receptor agonists, $β_2$-adrenergic receptor agonists, $β_3$-adrenergic receptor agonists and other nonspecific β-adrenergic receptor agonists. In a preferred embodiment, the β-adrenergic receptor agonist is a $β_2$-adrenergic receptor agonist or a $β_3$-adrenergic receptor agonists. Examples of β-adrenergic receptor agonists suitable for use with the methods of the present invention include, but are not limited to, albuterol, bitolterol, salbutamol, terbutaline, metaproterenol, procaterol, salmeterol, clenbuterol, isoproterenol, zinterol, BRL 37344, CL316243, CGP-12177A, GS 332, L-757793, L-760087, L-764646, and L-766892, etc. (see, e.g., Goodman and Gilman, supra).

Phosphodiesterase Inhibitors

In another preferred embodiment, the compound is a phosphodiesterase inhibitor. Cyclic nucleotide second messengers (cAMP and cGMP) play a central role in signal transductions and regulation of physiologic responses. Their intracellular levels are controlled by the complex superfamily of cyclic nucleotide phosphodiesterases (PDE) enzymes. Inhibitors of phosphodiesterases (PDE) are agents that can either activate or suppress PDEs via allosteric interaction with the enzymes or binding to the active site of the enzymes. The PDE family includes at least 19 different genes and at least 11 PDE isozyme families, with over 50 isozymes having been identified thus far. The PDEs are distinguished by (a) substrate specificity, i.e., cGMP-specific, cAMP-specific or nonspecific PDEs, (b) tissue, cellular or even sub-cellular distribution, and (c) regulation by distinct allosteric activators or inhibitors. PDE inhibitors include both nonspecific PDE inhibitors and specific PDE inhibitors (those that inhibit a single type of phosphodiesterase with little, if any, effect on any other type of phosphodiesterase). Still other useful PDE inhibitors are the dual selective PDE inhibitors (e.g., PDE III/IV inhibitors or PDE II/IV inhibitors). Below is a table setting forth various PDE inhibitors that are useful in the methods of the present invention.

| Isozyme Family | Regulatory Characteristics | Selective Inhibitors |
|---|---|---|
| I | $Ca^{2+}$, Calmodulin-regulated with different $K_m$ values for cG and cA hydrolysis | Vinpocetine |
| III | CG-inhibited cA hydrolysis; low $K_m$ for cA and cG | Milrinone, Amrinone, Pimobendan, Cilostamide, Enoximone, Peroximone, Vesarinone |
| IV | Low $K_m$ for cA hydrolysis | Rolipram; RO-20-1724 |
| V | High and low Km isoforms for cG specific hydrolysis | Zaprinast; Dipyridamole |

In one embodiment, the PDE inhibitor is a PDE V inhibitor. Useful phosphodiesterase type V inhibitors include, e.g., cialis, vardenafil, tanadafil, zaprinast, MBCQ, MY-5445, dipyridamole, furoyl and benzofuroyl pyrroloquinolones, 2-(2-Methylpyridin-4-yl)methyl-4-(3,4,5-trimethoxyphenyl)-8-(pyrimidin-2-yl)methoxy-1,2-dihydro-1-oxo-2,7-naphthyridine-3-carboxylic acid methyl ester hydrochloride (T-0156), T-1032 (methyl 2-(4-aminophenyl)-1,2-dihydro-1-oxo-7-(2-pyridylmethoxy)-4-(3,4,5-trimethoxy-phenyl)-3-isoquinoline carboxylate sulfate), and sildenafil. Cyclic GMP specific inhibitors include but not limited to A02131-1 [3-(5'-hydroxymethyl-2'-furyl)-1-benzyl thieno (3,2-c)pyrazole] for example. In another embodiment, the composition contains a phosphodiesterase type II (PDE II) inhibitor such as, e.g., EHNA. In yet another embodiment, the composition contains a phosphodiesterase type IV (PDE IV) inhibitor. Suitable phosphodiesterase type IV inhibitors include, but are not limited to, roflumilast, ariflo (SB207499), RP73401, CDP840, rolipram, mesopram, denbufylline, EMD 95832/3, cilomilast, RO-20-1724, and LAS31025. In still another embodiment, the phosphodiesterase inhibitor is a dual selective phosphodiesterase inhibitor such as, e.g., a PDE III/IV inhibitor (e.g., zardaverine) or phosphodiesterase inhibitors which can increase both cAMP and cGMP levels such as Satigrel (E5510, 4-cyano-5,5-bis(4-methoxyphenyl)-4-pentenoic acid).

In another embodiment, the PDE inhibitor is an inhibitor of the PDE III isozyme, for example, Olprinone.

In another embodiment, the PDE inhibitor is an inhibitor of the PDE IV isozyme family, or cAMP-specific and rolipram sensitive PDEs, which preferentially hydrolyze cAMP.

In yet another embodiment, the composition contains an agent that is a nonspecific phosphodiesterase inhibitor. Suitable nonspecific phosphodiesterase inhibitors include, but are not limited to, theobromine, dyphylline, IBMX, theophylline, aminophylline, pentoxifylline, papaverine, caffeine and other methylxanthine derivatives.

cAMP-Dependent Protein Kinase Activators

In other preferred embodiments, the compound used to treat the disorders described herein is a cAMP-dependent protein kinase activator. Examples of cAMP-dependent protein kinase activators include cAMP mimetics or dual cGMP/cAMP-dependent protein kinase activators. Suitable cAMP mimetics or analogs include those compounds that are structurally similar to cAMP and that have similar functions e.g., activities, as cAMP. Examples of suitable cAMP mimetics include, but are not limited to, 8-bromo-cAMP, dibutyryl-cAMP, Rp-cAMPS, and Sp-cAMPS, and useful dual activators include compounds such as, e.g., Sp-8-pCPT-cGMPS, Sp-8-bromo-cGMPS and 8-CPT-cAMP.

Superoxide Scavengers

In another embodiment, the compound used in the compositions and methods of the present invention is a superoxide anion ($O_2^-$) scavenger. Superoxide can react with NO and dramatically reduce its biological effects. Accordingly, agents that scavenge superoxide anions can enhance the effects of NO. Examples of superoxide scavengers include, but are not limited to, exogenous Mn or Cu/Zn superoxide dismutase (SOD) or small molecule SOD mimetics such as, e.g., Mn(III) tetra(4-benzoic acid) porphyrin chloride (MnT-BAP) and M40403 (see, e.g., Salvemini, et al., *Science,* 286 (5438):304-306 (1999)).

Potassium Channel Activators

In another aspect, the present invention provides pharmaceutical compositions comprising a potassium channel activator. In one embodiment, the potassium channel activator is an ATP-sensitive potassium channel activator. Synthetic compounds that activate ATP-sensitive K channels are smooth muscle relaxants. Such compounds include, but are not limited to, minoxidil, minoxidil sulfate, pinocidil, diazoxide, levcromokalim, cromokalim, etc. (see, e.g., White, et al, *Eur. J. Pharmacol.,* 357:41-51 (1998)). Additional suitable ATP-sensitive K channel activators can be found in, e.g., Bristol, et al., "*Annual Reports in Medicinal Chemistry,*" Vol. 29, Chap. 8, pp. 73-82, Academic Press (1991). In another embodiment, the potassium channel activator is a Maxi-K channel activator. Examples of activators of the Maxi-K channels include, but are not limited to, estrogen-like compounds, such as estradiol (see, Valverde, et al., *SCIENCE,* 285:1929-1931).

Benzodiazepines

In another aspect, the present invention provides pharmaceutical compositions comprising a benzodiazepine. Suitable benzodiazepines include, but are not limited to, alprazolam, brotizolam, chlordiazepoxide, clobazam, clonazepam, chlorazepate, demoxepam, diazepam, estazolam, flumazenil, flurazepam, halazepam, lorazepam, midazolam, nitrazepam, nordazepam, oxazepam, prazepam, quazepam, temazepam, and triazolam (see, e.g., Goodman and Gilman, supra).

Adrenergic Nerve Inhibitors

In another aspect, the compounds of the present invention are compounds that inhibit adrenergic nerves. Adrenergic nerve inhibitors include compounds that destroy sympathetic nerve terminals, such as 6-hydroxydopamine and its analogs (see, e.g., Goodman and Gilman, supra). Adrenergic nerve inhibitors also include compounds that deplete norepinephrine storage, either by inhibiting norepinephrine biosynthesis or be depleting stores, and compounds that inhibit norepinephrine release. Compounds that inhibit norepinephrine biosynthesis include, but are not limited to, α-methyltyrosine. Compounds that deplete norepinephrine stores include, but are not limited to, reserpine, guanethidine and bretylium. Compounds that inhibit norepinephrine release include, but are not limited to, clonidine and other ($\alpha_2$-adrenergic receptor antagonists. Examples of sympathetic nerve terminal destroyers include, but are not limited to, $\alpha_2$-adrenergic receptor antagonists.

Antidiarrheal Agents

In another aspect, the compounds of the present invention are antidiarrheal agents. Examples of suitable antidiarrheal agents include, but are not limited to, diphenoxylate, loperamide, bismuth subsalicylate, octreotide, etc. (see, e.g., Goodman and Gilman, supra).

HMG-CoA Reductase Inhibitors

In another aspect, the compounds of the present invention are HMG-CoA reductase inhibitors. Examples of HMG-CoA reductase inhibitors include, but are not limited to, mevastatin, lovastatin, simvastatin, pravastatin, cerivastatin, dalvastatin, atorvastatin, fluvastatin, etc. (see, e.g., Goodman and Gilman, supra).

Smooth Muscle Relaxants

In other embodiments, the compounds of the present invention are smooth muscle relaxants such as, e.g., hydralazine, papaverine, tiropramide, cyclandelate, isoxsuprine and nylidrin.

Adenosine Receptor Modulators

In another aspect, the present invention provides compositions for the treatment for a malignant cell phenotype comprising adenosine receptor modulators, either alone or in combination with another agent. Methods for the use of these compositions are also provided. In one group of embodiments, adenosine receptor modulators are used alone. In another group of embodiments, the adenosine receptor modulators are combined with at least one other muscle-relaxing agent. In other embodiments, the compounds of the present invention are adenosine receptor modulators such as methylxanthines. Examples of adenosine receptor modulators include theophylline and dyphylline. For other examples see, Goodman & Gilman, supra). Preferred agents are selected from those described with reference to the compositions of single agents or combinations above.

Theophylline, a plant-derived methylxanthine, has been used for the treatment of bronchial asthma for decades. Theophylline relaxes smooth muscle, notably bronchial muscle, that has been contracted experimentally with a spasmogen, or clinically in asthma. Proposed mechanisms of methylxanthine-induced physiologic and pharmacological effects include: 1) inhibition of phosphodiesterases, thereby increasing intracellular cyclic AMP, 2) direct effects on intracellular calcium concentration, 3) indirect effects on intracellular calcium concentrations via cell membrane hyperpolarization, 4) uncoupling of intracellular calcium increases with muscle contractile elements, and 5) antagonism of adenosine receptors.

A related compound, i.e., dyphylline, is a preferred adenosine receptor modulator. This compound is not metabolized by the liver and is excreted unchanged by the kidneys, therefore its pharmacokinetics and plasma levels are independent of factors that affect liver enzymes such as smoking, age, congestive heart failure, or the use of other drugs that affect liver function.

Adenylyl Cyclase Activators

In another aspect, the present invention provides compositions comprising adenylyl cyclase activators, either alone or in combination with other compounds or agents described herein. The adenylyl cyclase activator forskolin is preferred. Other examples of adenylyl cyclase activators, include, but are not limited to, N6, O2'-dibutyryl-cAMP, 8-chloro-cAMP, and Rp-diastereomers of adenosine 3',5'-cyclic monophosphorothioate, and related analogs, such as Rp-8-bromo-adenosine 3',5'-cyclic monophosphorothioate, and derivatives of forskolin, including colforsin daropate hydrochloride.

Endothelin Receptor Antagonists

In another aspect, the present invention provides compositions comprising endothelin receptor antagonist, either alone or in combination with other compounds disclosed herein. Examples of endothelin receptor antagonists include, but are not limited to, BE 1827B, JKC-301, JKC-302, BQ-610, W-7338A, IRL-1038, LRL-1620, bosetan, ABT 627, Ro 48-5695, Ro 61-1790, tesosentan (Ro 61-0612, ZD1611, BMS-187308, BMS-182874, BMS-193884, sitaxsentan (TBC 11251), TBC 2576, TBC 3214, TBC-10950, ABT-627, atrasentan, A-192621, A-308165, A-216546, CI-1020, EMD 122946, J-104132 (L753037), LU 127043, LU 135252, LU 302872, TAK-044 (69), SB 209670, SB 234551, SB 247083, ATZ1993, PABSA, L-749,329, RPR111723, RPR11801A, PD 164800, PD 180988 (CI1034), IRL 3630, IRL 2500, and their derivatives, etc. (see, Doherty, Annual Reports in Medicinal Chemistry, Volume 35, pp. 73-82, Academic Press, 2000). Other ethenesulfonamide derivatives, which are endothelin receptor antagonists and which are useful in the methods of the present invention, are disclosed by Harada, et al., *Chem. Pharm. Bull.*, 49(12):1593-1603 (2001).

Bisphosphonates

In another aspect, the present invention provides compositions comprising bisphosphonates, either alone or in combination with other agents. Suitable bisphosphonates suitable for use in the methods of the present invention include, but are not limited to, alendronate sodium (Fosamax), pamidronate disodium (Aredia), etidronate disodium Ididronel) and the like.

cGMP-Dependent Protein Kinase Activators

In another aspect, the present invention provides cGMP-dependent protein kinase activators, either alone or in combination with other agents disclosed herein. Suitable cGMP-dependent protein kinase activators include, but are not limited to, cGMP mimetics or dual cGMP/cAMP-dependent protein kinase activators. Suitable cGMP mimetics or analogs include those compounds that are structurally similar to cGMP and that have similar functions, e.g., activities, as cGMP. Examples of suitable cGMP mimetics include, but are not limited to, 8-bromo-cGMP, dibutyryl-cGMP, Rp-cG-MPS, and Sp-cGMPS, and useful dual activators include compounds such as, e.g., Sp-8-pCPT-cGMPS, Sp-8-bromo-cGMPS and 8-CPT-cAMP.

Guanylyl Cylase Activators

For example, BAY 41-2272 is a novel non-NO-based direct stimulator of soluble guanylyl cyclase that activates purified enzyme in a synergistic fashion with NO.

SOC Inhibitors

In another aspect, the present invention provides store-operated calcium influx (SOC) inhibitors, which inhibit calcium uptake into non-excitable cells in response to stimulus-mediated depletion of intracellular calcium storage pools. The SOC inhibitors preferably inhibit one or more of the following: calcium-dependent activation of nuclear factor of activated T cells (NFAT), nuclear factor kB (NF-kB), the stress kinase c-Jun N-terminal kinase (JNK) and exocytosis, resulting in the release or elaboration of inflammatory mediators. Examples of SOC inhibitors include for example statins in the δ-lactone form such as lovastatin, mevastatin, fluvastatin, pravastatin, dalvastatin, cerivastatin, atrovastatin and simvastatin.

Other treatment options include NO mimetics in combination with an antioxidant to further enhance efficacy. Such antioxidants include for example, lycopene, resveratrol, green tea polyphenolics (e.g. ECGC), brassinin (from cruciferous vegetables like Chinese cabbage), sulforaphane (from broccoli) and its analog sulforamate, withanolides (from tomatillos), and n-acetyl cysteine.

For purposes of the present invention by the term "animal" it is meant to include all mammals, and in particular humans. Preferably, NO mimetics are administered to an animal at risk for or suffering from a malignant cell phenotype. Such animals are also referred to herein as subjects or patients in need of treatment.

Low oxygen levels have been correlated with an increased level of cellular invasion and invasiveness. Hypoxic stress causes a variety of cellular adaptations, often manifesting in the up-regulation of certain genes.

For example, it has been shown that uPAR mRNA and cell surface uPAR protein levels increase under hypoxic conditions. uPAR is a high affinity cell surface receptor for pro-urokinase-type plasminogen activator (pro-uPA). Upon binding of pro-uPA to uPAR, the inactive single-chain pro-uPA is cleaved into its active, two-chain form. The activated enzyme, still attached to the receptor, then acts to convert plasminogen into plasmin, which ultimately degrades several components of the extracellular matrix (ECM). Active uPA also serves to activate both latent metalloproteinases and growth factors. uPAR also serves as a receptor for the ECM molecule vitronectin and can also modulate integrin function. In combination, these functions increase cellular invasion and potential for invasiveness. A positive correlation between hypoxia-induced uPAR up-regulation and carcinoma cell invasiveness has been suggested (Graham et al. Int. J. Cancer 1999 80:617-623). In addition, we have now shown hyponitroxia induced by administration of the nitric oxide synthase antagonist L-NMMA (0.5 mM) in hypoxic (1% $O_2$) and nonhypoxic (5% and 20% $O_2$) conditions to increase uPAR mRNA levels in human MDA-MD-231 cells incubated for 24 hours at 37° C.

Although the role of uPAR in invasion and tumor progression has been studied extensively, the regulatory mechanisms governing its expression are poorly understood. The invasive potential of a cell is highly dependent upon its ability to penetrate the extracellular matrix (ECM) and basement membranes that impede its movement. This process involves the participation of a number of proteolytic enzyme systems, of which the uPA system figures prominently. We postulate that the cGMP-dependent regulation of invasion and metastasis seen the current study was at least partially mediated through alterations in uPAR expression.

Figure 4:
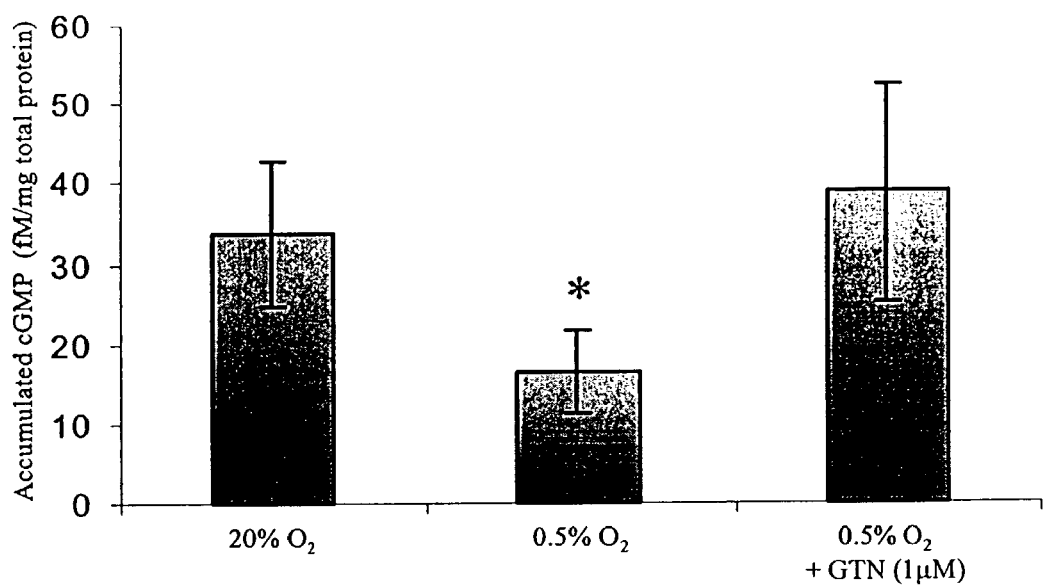
FIG. 4 illustrates the effect of hypoxia (0.5% $O_2$) on cellular cGMP Levels in MDA-MB-231 breast carcinoma cells.

We suggest a novel mechanism of oxygen sensing and uPAR regulation whereby phenotypes are modified in response to a decrease in cGMP-dependent signaling. This phenomenon is due to a reduction in endogenous NO synthesis. Molecular oxygen is obligatory for the conversion of L-arginine into NO and L-citrulline by the enzyme NO synthase (NOS). Indeed, exposure of cells to low levels of oxygen (1-3%) inhibits NO production by up to 90% and NOS inhibition has been shown to induce invasive phenotypes in a manner similar to hypoxia. Due to the reduced NO levels, there is a decrease in GC activity and a consequential reduction in cellular cGMP. Indeed, Taylor et al. (1998) showed that culturing intestinal epithelial cells in hypoxia (1% $O_2$; 24 Hrs) resulted in a significant decrease in basal and stimulated cGMP levels. Our studies have also suggested that a potential oxygen sensing mechanism of epithelial cells involves the participation of heme containing proteins such as GC. We have similarly shown that low oxygen levels decrease cGMP generation, and that they also result in phenotypic alterations. In both studies, these alterations were overcome by the addition of 8-Br-cGMP. We have further shown that inhibition of soluble guanylyl cyclase (sGC) with 1H-[1,2,4]Oxadiazole [4,3-a]quinoxalin-1-one (ODQ) can antagonize the ability of NO-mimetics to prevent the hypoxic up-regulation of uPAR. Given these findings we have derived a working model for the oxygen-mediated regulation of uPAR (FIG. 4). In this model, low oxygen levels result in decreased NO synthesis and a consequential decrease in sGC activation. As such, cellular cGMP levels are lowered, resulting in decreased PKG activity.

One possible mechanism involves a perturbation of the MAP kinase signaling pathway. This pathway is activated by hypoxia and studies have shown that NO can prevent the phosphorylation of ERK through a PKG-mediated interference of RAS/Raf. This concept has been strengthened by Yoshihide et al. (2000) who showed that NO donors and cGMP mimetics could reduce elastase levels by suppressing ERK phosphorylation. This led to a subsequent reduction in the activation and DNA binding capacity of AML1B (the transcription factor for elastase). It is possible that cGMP-dependent NO signaling similarly inhibits hypoxia-induced ERK phosphorylation, thereby decreasing the activation of the transcription factors responsible for the up-regulation of uPAR.

The promotor region of uPAR contains binding sites for transcription factors such as activator protein-1 (AP-1), Sp-1/3 and nuclear factor κB (NFκB). Hypoxia Inducible Factor 1 (HIF-1) levels may also contribute to the transcriptional activation of the uPAR gene, as previous examination of the sequence upstream of the uPAR initiation codon revealed the presence of at least 3 potential HIF-1-binding sites. It has also been shown that HIF-1 accumulation and transcriptional activity can be reduced by relatively high concentrations (2.5-500 μM) of NO mimetics such as SNP, S-nitroso-L-glutathione and 3-morpholinosydnonimine. Preliminary studies in our laboratory have confirmed that high concentrations (0.1-1 mM) of GTN and SNP inhibit HIF-1 accumulation and transactivating activity. However, concentrations of the NO mimetics that completely inhibited the hypoxic stimulation of metastasis, invasiveness and uPAR expression had no effect on HIF-1 accumulation or transactivating activity under hypoxia. Similarly, the administration of 8-Br-cGMP did not affect HIF-1 activity. Therefore it is unlikely that the cGMP-dependent regulation of invasive phenotypes is mediated via alterations in HIF-1.

Like uPAR, PAI-1 has also been shown to be stimulated under hypoxic conditions. See WO99/57306. Further, this stimulation was accompanied by a decrease in cellular adherence. PAI-1 is 52-kDa ECM glycoprotein which is produced by a variety of normal and malignant cells. This glycoprotein is a regulator of plasminogen activator activity. It functions to inhibit both free and bound uPA through the formation of irreversible covalent complexes. PAI-1 has also been shown to compete with the uPAR for binding to the same domain of vitronectin. As such, PAI-1 is capable of releasing cells bound to vitronectin-coated plates. Studies have shown that PAI-1 is required for the optimal in vitro invasiveness of lung carcinoma cells.

Hypoxia has also been shown to increase the resistance of cells to cytotoxic agents. The gene for PROXY-1 was identified using an RT-PCR based differential display following the culture of a variety of cell types under low levels of oxygen. See WO99/57306. It is believed that the 43-kDa PROXY-1 protein plays a role in protecting cells from insults including hypoxia, DNA damaging agents, cytotoxic agents and glucose deprivation, as enhanced PROXY-1 expression is observed in response to each of these harmful stimuli. Together with the fact that this gene is expressed by a variety of unrelated cell types, this type of gene expression is indicative of PROXY-1 being a universal 'switch' involved in the initial events that lead to cellular adaptations to hypoxia.

However, it is possible that the role of NO in tumor cell initiation promotion, progression, survival and apoptosis depends on the cell types, the concentrations of NO in the given cellular microenvironment, time of cellular exposure to NO, and possibly other factors. A similar paradigm has been drawn from the role of NO in acute and chronic inflammatory processes and in myocardial and neuro-protective preconditioning, for example. As a plieotropic transcriptional factor, NFκB (nuclear factor kappa B)-induced antiapoptotic signals have been suggested to be responsible for the development of chemoresistance in various forms of cancer, in tumor progression, and in the development of radiation resistance. NF-κB as a molecular target for developing anti-cancer therapy has been reviewed extensively by several investigators. Various known NFκB inhibitors such as NSAIDs, glucocorticoids, COX 2 inhibitors, and more recently proteasome inhibitors (blocks NF-κB activation), have been shown to be effective or potentially effective cancer treatment options. Known NFκB inducible genes that may be involved in tumor progression and chemoresistance include VEGF (vascular endothelium growth factor), EGFR (epidermal growth factor receptor), COX2 (cyclooxygenase type 2), MMPs (matrix metalloproteases 2 and 9 for example), uPAR (urokinase plasminogen activator receptor), etc. In a recent review article on inflammation and cancer, anti-inflammatory therapy is considered an efficacious approach towards early neoplastic progression and malignant conversion It is possible that NO may function as the feedback inhibitor of NFκB upregulation/activation. Alternatively, NO may affect p53 tumor suppressor gene expression, or BcL expression. It is also possible that NO may enhance chemosensitivity of tumor cells via a completely unknown mechanism. While the traditional approach to treat cancer with combination chemotherapeutic agents and/or radiation therapy is primarily based on the known mechanism of action, current approach focuses on the balancing the effectiveness of the treatment and toxicity profile of selected drugs. Since many of the NO mimetics are proven to be safe for both acute and chronic usage, it presents as a unique opportunity to minimize the safety risk when NO mimetics is added to the known standard of treatments of various forms of cancer.

In some forms of cancer, for example, prostate and breast cancers, hormonal therapy is typically used for early phase of the diseases. Hormonal therapy includes anti-androgens (e.g. flutamide) for prostate cancer and anti-estrogen (e.g. tamoxifen) for estrogen receptor positive or ER status unknown early stage breast cancers. In general, the tumor responded well to the hormonal therapy before a new phenotype is developed. The newly developed phenotypes are typically no longer responding to the original hormonal therapy; prognosis for patients at this stage of cancer, i.e. hormone refractory/insensitive phase is typically very poor. Even while using hormonal therapy during the hormone responding phase of cancers, patients suffer from hot flashes, loss of libido, sexual dysfunction, osteopenia, osteoporosis, poor self-esteem and quality of life. The mechanism leading to the loss of hormone response of these cancer phenotypes are largely unknown at this point. It could be related to androgen/estrogen receptor expression levels, cellular locations, functional activities of these steroid receptors. Alternatively, it could also due to the altered non-genomic actions of these steroid targets at various cellular compartments and sub-compartment, e.g. mitochondria.

Endogenous androgens including testosterone and 5-α-dihydrotestosterone (DHT; one of the two key metabolites of testosterone) are essential for the development and maintenance of reproductive tissues (e.g. testis, epididymis, seminal vesicles, penis, etc.) in male species. Exogenously administered androgens, e.g. testosterone undecanoate, testosterone propionate, etc. typically transformed to testosterone or DHT before exerting its biological activity. The majority of the biological activities of testosterone and DHT are elicited by the cytosolic androgen receptor (AR). The AR is a member of the steroid hormone-thyroid hormone-retinoic acid nuclear receptor super-family. Upon androgen binding, the AR undergoes conformational changes resulting in the release of inhibitory proteins and is subsequently hyper-phosphorylated, translated to the cell nucleus. Once in the nucleus, AR is dimerized and binds to hormone response elements in the regulatory regions of androgen target genes, and subsequent gene transcriptional events. DHT binds to AR with higher affinity and induces a higher level of androgen-regulated gene expression than testosterone. Since the second key metabolite is $E_2$, the biological activity of testosterone is also mediated at least in part, by the activation of estrogen receptor.

Evidence has been recently obtained for ligand-independent activation of AR transcriptional activity by peptide growth factors, such as IGF-I (insulin-like growth factor), and to a lesser extent, keratinocyte growth factor and epidermal growth factor. Like other steroid receptor ligands, testosterone can also elicit biological activities via non-genomic mechanisms that often involve ion fluxes in androgen-dependent cell types. Specifically, calcium fluxes following addition of picomolar concentrations of testosterone have been reported in rat heart myocytes, male rat osteoblasts, human prostate cancer cells, and Sertoli cells. Direct evidence from patch-clamp studies showed that testosterone can open $K^+$-channels in single coronary myocytes. Although testosterone mediated ion fluxes have been reported in various cell types, the biological consequences of these activities are still poorly defined.

While infrequent in early and localized prostate tumors, mutations of the AR have been identified in a number of advanced prostatic cancers. Substantial evidence suggests that AR activity is enhanced in advanced forms of prostate cancer, and in some cases, as a result of gene amplification events. Frequently, the AR also appears to have altered ligand specificity; for example, advanced prostate cancers often become androgen-independent, and no longer respond to androgen ablation therapy. The loss of androgen-sensitivity is considered an indicator of poor prognosis for advanced prostate cancers.

NO mimetics may be able to maintain the tumor cell under homeostatic stage, thus prevent the alteration of steroid receptor expressions, levels of expression, location, or alternatively, the ion-channels related to androgen and anti-androgen action etc. Thus, the administration of NO mimetics could keep patients under hormonal therapy for various forms of cancer under hormone responsive phase, preventing or delaying metastasis to secondary sites and transformation to more advanced, hormone-refractory/insensitive/insensitive cancers. NO mimetics can be administered in conjunction with hormonal therapy during the treatment phase and/or can be used in the remission phase.

In certain cases, NO mimetics can be used with chemo- and/or radio-therapeutic treatment to ensure eradication of cancers during the treatment phase, and can be used as stand-alone therapy during the remission. If low dose of chemotherapy is employed to prevent cancer recurrence, NO mimetics can be used with the low dose chemotherapy to prevent or prolong the time to cancer recurrence and eventually, prolong the survival time of cancer patients. The addition of NO mimetic therapy could also 1) reduce the dependence on narcotic pain relief agents and thus associated adverse events due to their use and yet enhance the effectiveness of these agents, 2) prevent progressive lost of bone mineral density and thus, the development of osteoporosis and the risk of bone fracture, and 3) improve overall quality of life of cancer suffers.

We have now found that nitric oxide is a primary mediator of cellular adaptive responses to changes in oxygen levels in and around the cell. Through administration of a low dose of a nitric oxide mimetic, we have shown that nitric oxide mimetic activity can be increased, restored or maintained at a level which inhibits or prevents a malignant cell phenotype. In contrast, the effect of maintaining low oxygen levels on cells was limited to inhibiting basal levels of endogenous nitric oxide production.

Under hypoxic conditions where the levels of oxygen are limiting, we have now demonstrated that cancer cell lines acquire one or more of the following malignant cell phenotypic properties: they increase their lung-colonization ability following i.v. inoculation into syngeneic mice (experimental metastasis); they increase their invasiveness through the extracellular matrix in vitro (also relevant to metastasis); and they become more resistant to the chemotherapeutic drug doxorubicin and 5-fluorouracil. In these experiments, cancer cells were exposed to 1% $O_2$ (10-15 mmHg $PO_2$) to induce hypoxia and compared with nonhypoxic cancer cells exposed to 5-20% $O_2$ (30-160 mmHg). By administering low doses of nitric oxide mimetics (during periods when oxygen levels are limiting and/or when endogenous nitric oxide production is inhibited) acquisition of these malignant phenotypic changes is prevented. This prevention occurs even when the cells are in an extremely hypoxic environment.

We have now demonstrated that low concentrations of nitric oxide mimetics SNP and/or glyceryl trinitrate (GTN) inhibit the hypoxic up-regulation of uPAR and PAI-1, as well as PROXY-1. Similar low dose nitric oxide mimetic therapy is expected to also be effective in inhibiting hyponitroxic upregulation of these genes such as that observed in cells treated with L-NMMA (0.5 mM), i.e. inhibiting and preventing a malignant cell phenotype.

Experiments performed in human breast cancer cells cultured in hypoxic conditions (1% $O_2$) showed that treatment of the hypoxic cells with $10^{-12}$ M SNP significantly reduced levels of uPAR mRNA as compared to untreated control hypoxic cells and hypoxic cells treated with $10^{-8}$ M SNP. Similarly, treatment of breast cancer cells cultured in hypoxic conditions with the nitric oxide mimetic GTN at low doses of $10^{-11}$ M and $10^{-10}$ M significantly reduced uPAR mRNA levels in the hypoxic cells as compared to untreated hypoxic cells and to hypoxic cells treated with GTN at $10^{-9}$ M, $10^{-8}$ M, $10^{-7}$ M, $10^{-6}$ M and $10^{-5}$ M. In fact, levels of uPAR mRNA in hypoxic breast cancer cells treated with $10^{-11}$ M GTN and $10^{-10}$ M GTN were similar to levels of uPAR mRNA measured in cells cultured under non-hypoxic conditions (20% $O_2$). Levels of uPAR mRNA in hypoxic cells treated with GTN at $10^{-6}$ M and $10^{-5}$ M were similar to levels of untreated hypoxic cells, suggesting tolerance to the NO mimetic. A reduction in uPAR protein levels was also observed in these cells 24 hours after incubation with these nitric oxide mimetics.

Further experiments with human invasive trophoblast cells (HTR-8/SVneo) confirmed the ability of low doses of these nitric oxide mimetics to decrease expression of uPAR in hypoxic cells.

The effects of treatment of HTR-8/SVneo invasive trophoblast cells with the nitric oxide mimetic GTN on PROXY-1 mRNA levels was also examined. PROXY-1 mRNA levels were very low in cells cultured in 20% $O_2$. However, levels of PROXY-1 mRNA were increased in cells cultured in 1% $O_2$ which were untreated or treated with $10^{-7}$ M GTN. In comparison, levels of PROXY-1 were much lower in hypoxic cells treated with a low dose, $10^{-11}$ M GTN.

In addition, the effects of the nitric oxide mimetics SNP and GTN on PAI-1 mRNA levels in breast cancer cells were examined. Again, treatment of hypoxic cells with low doses of the nitric oxide mimetics SNP ($10^{-12}$ M) and GTN ($10^{-11}$ M) significantly decreased levels of PAI-1 mRNA as compared to untreated hypoxic cells.

Experiments were also performed to ascertain the effects of low doses of nitric oxide mimetics on levels of metalloproteinase. Breast cancer cells were incubated in hypoxic or control conditions in the presence of varying concentrations of SNP or GTN. Treatment of hypoxic cells with low doses, $10^{-11}$ M GTN and $10^{-12}$ M SNP, of a nitric oxide mimetic resulted in a decrease in gelatinases secreted from the cells as compared to untreated hypoxic cells.

Figure 1:
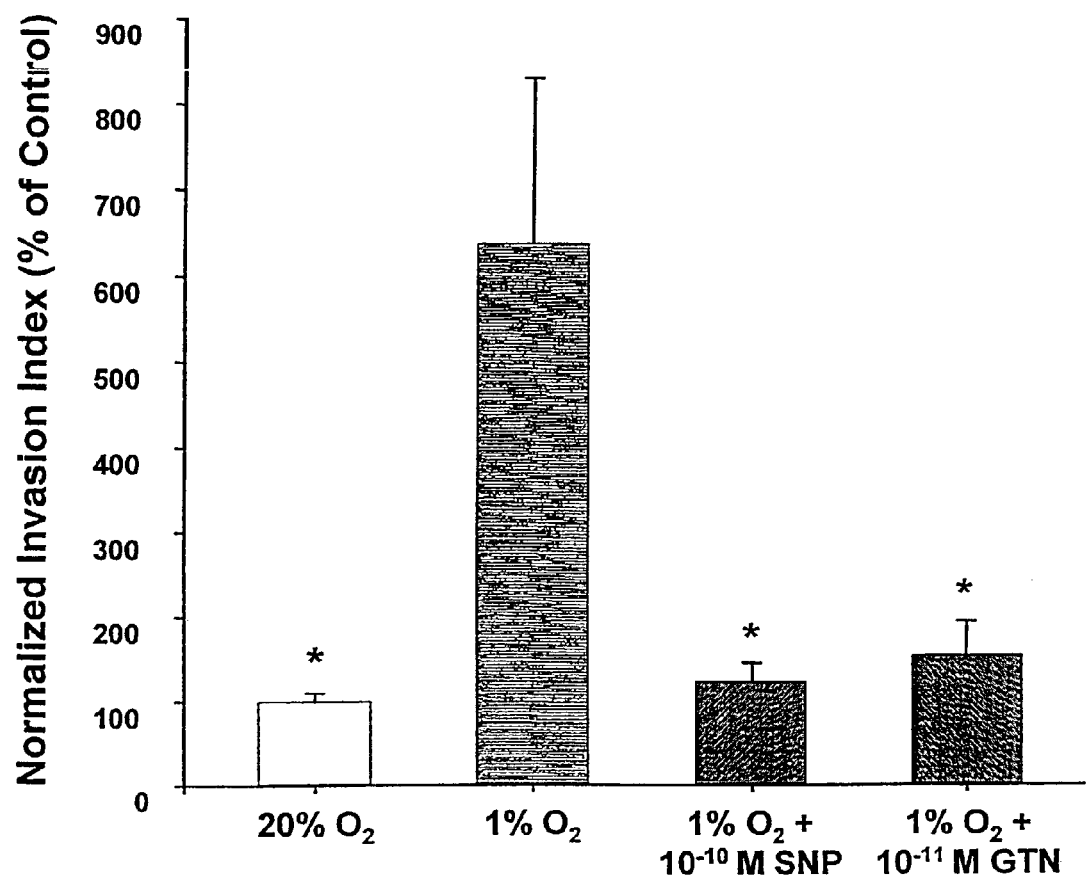
FIG. 1 is a histogram showing the effect of GTN and SNP on the in vitro invasion by MDA-MB-231 invasive breast cancer cells in hypoxic (1% $O_2$) conditions as compared to normal (20% $O_2$) conditions. Cells were coated onto Matrigel-coated membranes and incubated under hypoxic or normal conditions, alone or in the presence of nitric oxide mimetics. The invasion index (% of control), which is taken to be a measure of the invasive potential of the cells for each treatment, was determined by staining the cells that invaded through the membrane and counting them. The first bar depicts the invasion index of cells cultured under normal conditions (20% $O_2$). The second bar depicts the invasion index of cells cultured under hypoxic conditions (1% $O_2$). The third bar depicts the invasion index of cells cultured under hypoxic conditions (1% $O_2$) and administered $10^{-10}$ M SNP. The fourth bar depicts the invasion index of cells cultured under hypoxic conditions (1% $O_2$) and administered $10^{-11}$ M GTN. The values indicated by "*" were significantly different ($p<0.05$, $n=6$) using the Student-Newman-Keuls post-hoc test for pair-wise multiple comparison procedures.

Functionally, inhibition of the hypoxic up-regulation of these genes was then shown to result in a decrease in cellular invasiveness and drug resistance. The invasive ability of cells in hypoxic conditions in the presence or absence of nitric oxide mimetics was also assessed using Matrigel invasion chambers (modified Boyden chambers). In these in vitro invasion assays, either breast cancer cells (see FIG. 1) or HTR-8/SVneo invasive trophoblasts were plated on Matrigel-coated membranes. Cells were then incubated under hypoxic or normal conditions, alone or in the presence of nitric oxide mimetics. The invasion index for each treatment was determined by staining the cells which invaded through the membrane and counting them. In both cell lines, treatment with low doses of nitric oxide mimetics significantly reduced hypoxic cell invasiveness as compared to untreated hypoxic cells. The invasive indices of hypoxic breast cancer cells treated with $10^{-10}$ M SNP and $10^{-11}$ M GTN were similar to or even lower than cells cultured under non-hypoxic conditions. In HTR-8/SVneo trophoblast cells, $10^{-7}$ M GTN inhibited invasiveness of hypoxic cells by 56.2%, while $10^{-8}$ M SNP inhibited invasiveness by 63.4%.

The ability of low doses of nitric oxide mimetics to inhibit metastases of tumor cells in animals was then confirmed. In a first set of experiments, the ability of hypoxic conditions to increase number of metastases was demonstrated. In these experiments, mice were administered via tail vein injection a bolus of metastatic melanoma cells. Immediately after injection the mice were divided into two groups. The first group was placed in a chamber with a continuous flow of a gas mixture comprising 21% $O_2$ (room air). The second group was placed in a hypoxic environment with only 10% $O_2$. After 24 hours, both groups were removed and placed in regular cages kept at room air. After 14 days, the animals were sacrificed and metastatic nodules in the lungs of the animals were counted. Animals in the hypoxic environment had a 2-fold statistically higher number of lung nodules as compared to animals in the non-hypoxic environment.

Figure 2:
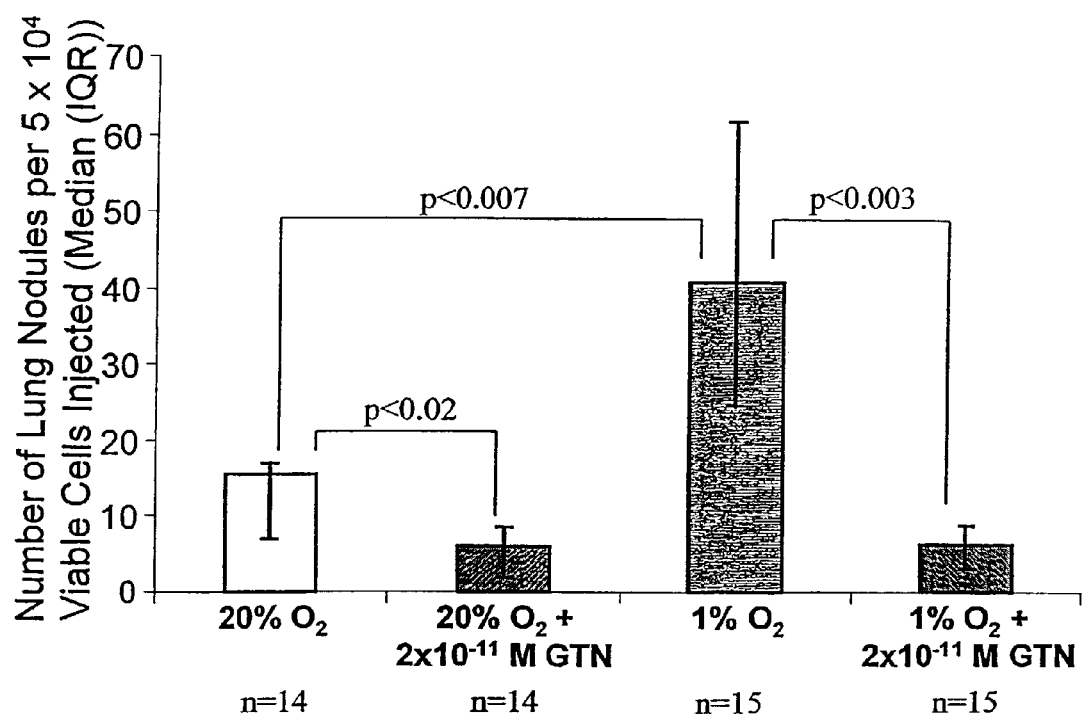
FIG. 2 is a histogram showing the lung colonization ability of B16F10 mouse melanoma cells incubated for 12 hours in 1% or 20% $O_2$ in the presence or absence of $2\times10^{31\ 11}$ M (20 pM) GTN and injected i.v. (tail vein) into C57B16 female mice. Fourteen days later, mice were sacrificed and lungs were removed and fixed in Bouin's fixative. Both melanotic and amelanotic metastatic colonies were counted under a dissecting microscope. The first bar depicts the number of nodules observed in lungs of mice injected with cells cultured in normal conditions (20% $O_2$). The second bar depicts the number of nodules observed in lungs of mice injected with cells cultured in normal conditions (20% $O_2$) and administered $2\times10^{31\ 11}$ M GTN. The third bar depicts the number of nodules observed in lungs of mice injected with cells cultured in hypoxic conditions (1% $O_2$). The fourth bar depicts the number of nodules observed in lungs of mice injected with cells cultured in hypoxic conditions (1% $O_2$) and administered $2\times10^{11}$ M GTN.

In a second set of experiments, mice were injected with mouse melanoma cells which were pre-incubated for 12 hours in 1% or 20% $O_2$ in the presence or absence of a low concentration of a nitric oxide mimetic (GTN; $2\times10^{-11}$ M). After fourteen days, the mice were sacrificed and the lungs were visually observed for metastatic nodules. In addition, the number of lung nodules in these mice was compared. Lungs of animals that had been administered hypoxic and non-hypoxic melanoma cells treated with the nitric oxide mimetic prior to injection exhibited statistically less metastatic nodules as compared to animals administered either untreated hypoxic and non-hypoxic melanoma cells (see FIG. 2). Specifically, the in vitro pre-treatment with $2\times10^{-11}$M GTN decreased the hypoxia-stimulated lung nodule formation by 85% and, even in 20% oxygen, the GTN pre-treatment reduced the extent of metastasis by more than 60%. In fact, the suppression of lung nodule formation by GTN pre-treatment was found to be equivalent regardless of the in vitro oxygenation levels. Further, treatment of the cells with L-NMMA prior to inoculation into mice resulted in a 63% overall increase in the number of lung nodules ($p<0.01$; post hoc Fisher's test). Concomitant treatment using GTN ($10^{-10}$M) and L-NMMA attenuated this metastatic response by 60% ($p<0.0005$). The frequency distribution of lung nodules across the three experimental groups ranged from 0 to 111. No lung nodules were found in two of the control mice and four of the GTN-treated mice. Characterization of the lung nodule frequency by tertile revealed a consistent pattern of suppression throughout the NO-mimetic treated group compared to the L-NMMA treated group. In addition, the metastasis in the GTN-treated group was significantly below even the control levels in the highest tertile. Taken together, these data indicate that the levels of NO, and not oxygen itself, determine the severity of the metastatic phenotype. Further, the effect of low-concentration GTN treatment on lung nodule formation was not due to a non-specific cytotoxic or growth inhibitory effect on the cells as they had similar in vitro colony-forming ability as untreated cells.

As will be understood by those skilled in the art upon reading this disclosure, results from the studies in this murine model can be used to predict drug disposition in other species including humans, to define pharmacokinetic equivalence in various species including humans and design dosing regimes for other experimental animal models and for human clinical studies. Such pharmacokinetic scaling is performed routinely based upon data such as provided herein as evidenced by references such as Mordenti, J. J. Pharm. Sci. 1986 75(11): 1028-1040.

Figure 3A:
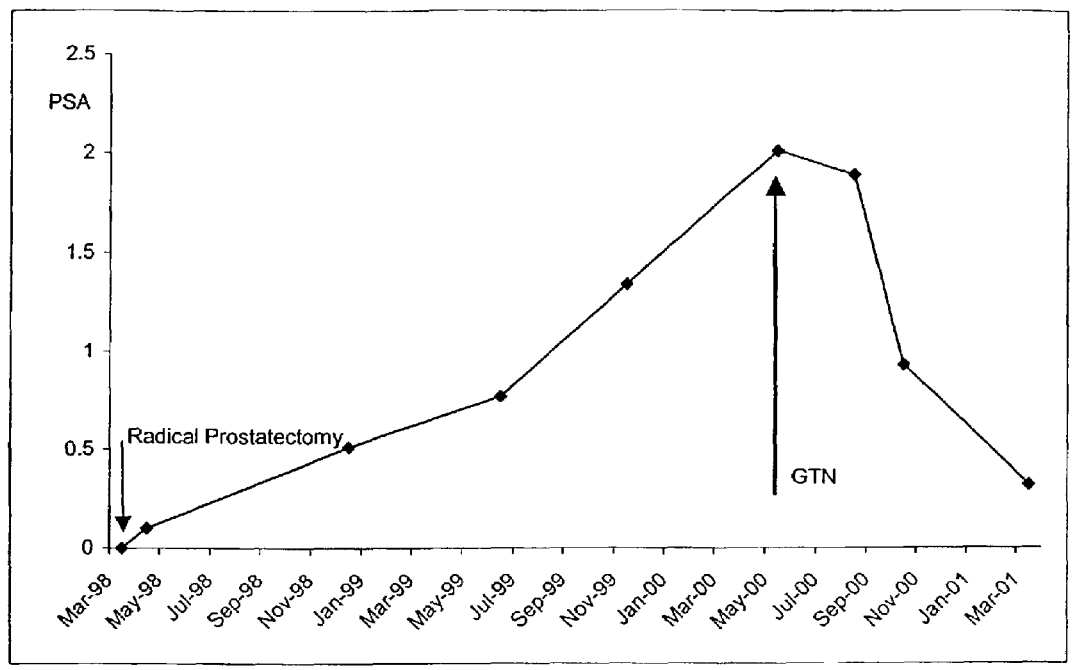
FIG. 3 shows circulating prostate specific antigen (PSA) levels in two patients, Patient A (FIG. 3A) and Patient B (FIG. 3B) who had undergone radical prostectomy. A sharp decline in plasma PSA levels was observed in both patients within two months of administration of low dose NO mimetic therapy. In Patient A, this decline continued throughout the course of the study. In Patient B, further increases in PSA levels were minimal. Plasma PSA levels were measured using a radioimmunoassay that has an accuracy of ±0.1 ng/ml.
Figure 3B:
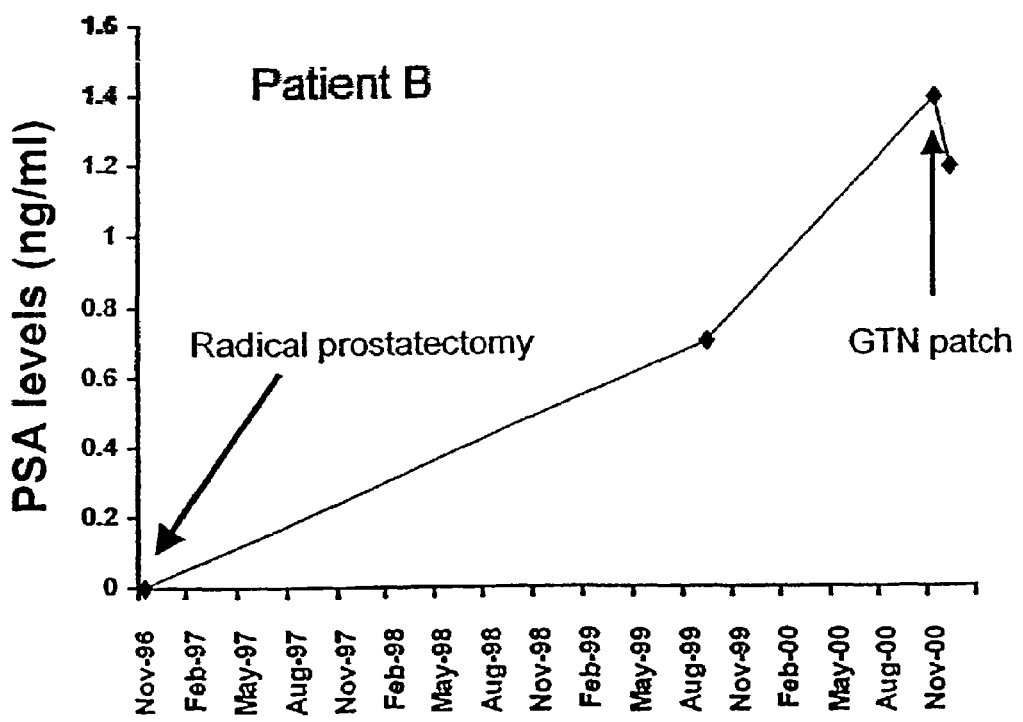

Further, the ability of an NO mimetic to reduce disease progression in humans was demonstrated. In this study, continuous transdermal patches were used to deliver very low doses of GTN (0.033 mg/hour) to patients with recurrent prostatic adenocarcinoma. Patients with prostatic adenocarcinoma were selected for this study because the progression of this type of cancer correlates well with the plasma levels of prostate-specific antigen (PSA). Thus, the outcome of low dose NO mimetic therapy can be easily assessed by measuring PSA levels. Analysis of data from two patients in this study revealed a sharp decline in plasma PSA levels within two months of GTN treatment, thus indicating low dose NO mimetic therapy to be an effective approach to the management of cancer, particularly prostate cancer, in humans (see FIGS. 3A and 3B). Plasma PSA levels were measured via a commercially available immunoassay kit such as Immuno 1 (Bayer Corporation).

The ability of low doses of nitric oxide mimetics to decrease resistance of breast cancer cells to doxorubicin was also examined. In these experiments, the ability of hypoxic conditions to increase resistance to doxorubicin was first confirmed. Cells exposed to 1% $O_2$ had higher survival rates at concentrations of 25 and 50 µM doxorubicin as compared to cells exposed to 20% $O_2$. The effect of low doses of the nitric oxide mimetic GTN on doxorubicin resistance of hypoxic and non-hypoxic cells was then examined. It was found that hypoxic cancer cells treated with $10^{-6}$ M and $10^{-10}$ M GTN had lower doxorubicin survival rates as compared to untreated hypoxic cells. The survival rates of the nitric oxide mimetic treated hypoxic cells were comparable to those observed in untreated non-hypoxic cells and non-hypoxic cells treated with the nitric oxide mimetic. These results have been confirmed in multiple human cancers as well as mouse cancers and with other antimalignant therapeutic modalities.

Thus, these studies demonstrate that a malignant cell phenotype such as that induced by hypoxia can be inhibited and prevented by increasing (restoring) the level of nitric oxide mimetic activity. Other factors known to lower cellular nitric oxide mimetic activity so as to induce a malignant cell phenotype include, but are not limited to, decreases in arginine levels, exposure to endogenous nitric oxide synthase antagonists such as L-NMMA and ADMA, exposure to endogenous nitric oxide scavengers such as superoxide, changes in nitric oxide synthase expression, changes in cofactors such as GSH and NADPH, glucose deprivation, surgical procedures, administration of anesthetic agents, administration of pharmacologic agents which alter circulation such as, but not limited to antihypertensive agents, and traumatic injuries including, but not limited to those associated with blood loss, decreased blood volume, and hemorrhage. The present invention relates to methods of inhibiting and preventing a malignant cell phenotype resulting from these and other factors by administering low doses of one or more nitric oxide mimetics.

The low dose nitric oxide mimetic therapy of the present invention will also prevent the malignant cell phenotype of vascular endothelial cells which ultimately results in recruitment of such cells by a tumor and development of a blood supply to the tumor, also known as angiogenesis. Attempts at cutting off tumor blood supply by blocking VEGF in vascular endothelial cells have been relatively unsuccessful as cancer treatments. The presence of VEGF in tumors has been shown to suppress tumor invasiveness. Thus, it is believed that agents which remove or block the actions of VEGF, such as anti-VEGF antibody, actually generate more aggressive cancer cell phenotypes. Using the present invention, however, generation of a more aggressive malignant cell phenotype can be prevented, thereby allowing use of anti-VEGF therapies to prevent angiogenesis without producing more aggressive cancer cells.

These studies also demonstrate the ability of low dose NO mimetic therapy to decrease levels of a tumor marker in a patient. Tumor marker levels are used routinely by those of skill in the art as indicators of the progression of a cancer. Accordingly, the ability of low dose NO mimetic therapy to decrease levels of these markers is indicative of its ability to treat cancers. Further, progression of a tumor can be diagnosed and/or monitored in a patient by measuring the levels of a tumor marker in the patient in the presence of a low dose of a nitric oxide mimetic.

Low dose formulations of nitric oxide mimetics which ultimately result in an increase, restoration or maintenance of nitric oxide mimetic activity of cells sufficient to prevent or inhibit a malignant cell phenotype can be produced in accordance with formulation methods known in the art. Formulations for the administration of nitric oxide mimetics in accordance with the method of the present invention can take the form of ointments, transdermal patches, transbuccal patches, injectables, nasal inhalant forms, spray forms for deep lung delivery through the mouth, orally administered ingestible tablets and capsules, and tablets or lozenges, or "lollipop" formulations for administration through the oral mucosal tissue. The latter formulations included tablets, lozenges and the like which are dissolved while being held on or under the tongue, or in the buccal pouch. It is preferred that the pharmaceutical preparations provide a low dose of the nitric oxide mimetic sufficient to increase, restore or maintain nitric oxide mimetic activity at a level which inhibits or prevents a malignant cell phenotype, also referred to herein as a therapeutically effective amount, during the period in which cellular nitric oxide mimetic activity of cells is lowered. Also preferred are formulations comprising more than one NO mimetic. In this embodiment, it is preferred that the NO mimetics target or act on different parts of the NO pathway. For example, an NO donor can be co-administered with a compound that inhibits cyclic nucleotide (e.g. cAMP or cGMP) degradation such as a phosphodiesterase inhibitor. Preferred phosphodiesterase (PDE) inhibitors useful as NO mimetics are those inhibiting PDE-1 through PDE-5.

While the methods of the present invention are useful for treating a broad range of diseases, they are particularly effective for lung cancer, including non-small cell lung cancer and small cell lung cancer; mesothelioma; thymic tumors; breast cancer, such as ductal carcinoma in situ, lobular carcinoma in situ, ductal carcinoma of special type, and invasive lobular carcinoma; colorectal cancer; anal cancer; esophageal cancer; gastric cancer; small intestine and carcinoid tumors; cancers of the liver such as primary liver cancer and hepatocellular carcinoma; cancer of the biliary tract, including cholangiocarcinomas; tumors of the gall bladder; pancreatic cancer; endocrine cancers such as thyroid cancer, adrenal cancer, and neuroblastoma; genitourinary cancers such as renal cancer, Wilms' tumor, cancer of the bladder and ureter, prostate cancer, and testicular cancer; gynecological cancers such as ovarian cancer, cancer of the uterine corpus, cancer of the cervix, vaginal and vulvar cancer, and trophoblastic tumors; head and neck cancer such as cancer of the larynx, cancer of the oral cavity, carcinoma of the nasopharynx, cancer of the nasal cavity and paranasal sinuses, cancer of the eye and orbit, and salivary gland tumors; tumors of the central nervous system such as primary brain tumors and brain metastatses; skin cancer, including primary cutaneous malignant melanoma and non-melanoma skin cancers; hematological malignancies including acute leukemia, chronic lymphoid leukemias, Hodgkin's disease, non-Hodgkin's lymphomas, and myeloma; bone and soft tissue malignancies such as osteosarcoma, Ewing's sarcoma, other primary bone tumors, and soft tissue sarcomas; cancer of unknown primary site; paraneoplastic syndromes, including endocrine paraneoplastic syndromes, neurological paraneoplastic syndromes, hematological paraneoplastic syndromes, and dermatological paraneoplastic syndromes; and AIDS-related malignancies, including Kaposi's sarcoma, non-Hodgkin's lymphoma, and primary central nervous system lymphoma. Table 2 provides an exemplary list of cancers which can be treated using the methods and formulations of the present invention, and the current standard of care used to treat these cancers as well as investigational treatments used to treat these cancers.

TABLE 2

| Type of Cancer | Description of the Cancer | Standard of Care and Investigational Treatments |
|---|---|---|
| Lung Cancer | Lung cancers are grouped as non-small cell (NSCLC) or small cell (SCLC), but within the former certain patterns of disease do relate to histological subtype. For example, squamous cancers typically arise in proximal segmental bronchi and grow slowly, disseminating relatively late in their course. Adenocarcinomas are often peripheral in origin and even small respectable lesions carry a risk of occult metastases. | Surgical removal of non-small cell bronchogenic carcinoma continues to offer best possibility of a cure. Radical radiotherapy is indicated for patients with who are unfit for surgery, or have good performance status and disease that can be encompassed in a radical volume. The standard international dose is 60 Gy in 30 fractions over 6 weeks. The standard treatment volume in most of the world is the primary tumor and hilar and mediastinal lymph nodes, with a 1-2 cm margin. Chemotherapy delivered synchronously with radiotherapy is being investigated. Cisplatin-based therapy significantly improves survival and quality of life. The most studied regimen is MIC (mitomycin C, isosfamide, and cisplatin).. Combination chemotherapy is now the standard treatment for limited and extensive SCLC. Patients with small cell lung cancer (SCLC) are usually treated by primary chemotherapy because of its chemo-responsiveness and frequent dissemination at time of diagnosis. SCLC is, however, also the most radio-responsive variety of bronchial carcinoma and radiotherapy has an important role in its management. In patients with a localized tumor, thoracic irradiation (TI) and |

TABLE 2-continued

| Type of Cancer | Description of the Cancer | Standard of Care and Investigational Treatments |
|---|---|---|
| | | prophylactic cranial irradiation (PCI) improve disease control at these sites and can lead to prolongation of survival.<br>The following courses of radiotherapy are commonly used: TI-50 Gy in 2Gy daily fractions or biological equivalents; PCI-24 Gy in 8 fractions, 30 Gy in 10 fractions, or 36 Gy in 18 fractions. It is common practice to irradiate the mediastinum even in the absence of lymphadenopathy because of frequency of occult nodal metastases.<br>A number of chemotherapeutic drugs have been found to have activity as single agents and a variety of combination regimens have been developed. CAV (cyclophosphamide, doxorubicin and vincristine) and EP (etoposide and cisplatin) have similar efficacy. |
| Malignant pleural mesothelioma (MPM) | Aggressive tumor arising from the serosal lining of the chest and abdomen with survival rates of less than one year reported following diagnosis. | Without treatment, the average patient with MPM survives less than one year from the time of diagnosis. As a result of this poor prognosis various therapeutic options have been explored, including radiotherapy, chemotherapy, immunotherapy and surgery. Current experience has shown multimodality therapy to offer improved survival in selected patient groups. |
| Thymic Tumors | Tumors derived from the thymus (thymomas) comprise approximately 20% of all mediastinal tumors and are the most common tumor in the anderior mediastinum. Thymomas occur at any age but are rare before the age of 20 and peak between 40-60 years.<br>Most thymomas are slow-growing 'low-grade' malignant tumors. It is believed that they derive from epithelial elements, but the tumors retain the capacity for production of T cells. | The contemporary standard of treatment for thymoma is radical surgery whenever possible. Total resection alone is adequate therapy for early stage thymoma. Adjuvant therapy should be used for local disease with demonstration or suspicion of invasion. In local disease with or without residual tumor, radiotherapy is recommended in doses of 50-60 Gy given in 20-30 fractions. Locally advanced, relapsing, or disseminated disease should be treated with combination chemotherapy including corticosteroids. Cisplatin-based regimens are recommended. |
| Breast Cancer | Breast cancer is the most common solid cancer occurring in women. It is estimated that 5-10% of female breast cancer is due to inheritance of a mutated copy of either BRCA1 or BRCA2. Other genes contribute less frequently to familial breast cancer. Male breast cancer is rare (0.7% of all male cancers) with a peak incidence 10 years later than women. It may occur in association with Klinefelter's syndrome.<br>Ductal carcinoma in situ (DCIS)<br>90% of breast carcinomas arise in the ducts of the breast, beginning as atypical proliferations of ductal epithelium that eventually fill and plug the ducts with neoplastic cells. As long as the tumor remains within the confines of the ductal basement membrane it is classified as DCIS. Not all DCIS will inevitably progress, but the probability of development of invasive cancer is estimated at 30-50%. | Early breast cancer is defined as disease that can be completely extirpated by surgery. The management of this disease comprises: treatment of the breast and axilla; pathological staging to direct adjuvant therapy; adjuvant therapy-endocrine, chemotherapy, radiotherapy; and follow-up.<br><br>All patients require removal of the primary tumor with either wide local excision or mastectomy. Breast irradiation has been shown to reduce the risk of local recurrence after breast-conserving surgery. Typically, the whole breast is treated with tangential fields to a dose of 50 Gy in 25 fractions (or an equivalent dose-fractionation regimen), with care taken to minimize the volume of lung and heart irradiated.<br>Primary chemotherapy or hormone therapy for operable breast cancer provides early systemic treatment and allows assessment of the response to treatment; by definition this is impossible with adjuvant therapy. Studies have compared pre- and post-operative chemotherapy (doxorubicin and cyclophosphamide). Pre-operative treatment does downstage the primary tumor and may facilitate breast-conserving surgery where mastectomy would otherwise be required.<br>Locally advanced disease is defined by the presence of infiltration of the skin or the chest wall or fixed auxillary nodes. The probability of metastatic disease is high. |

TABLE 2-continued

| Type of Cancer | Description of the Cancer | Standard of Care and Investigational Treatments |
|---|---|---|
| | Lobular carcinoma in situ These pre-invasive lesions carry a risk not only of ipsilateral invasive lobular carcinoma but also of contralateral breast cancer. Invasive ductal carcinoma This accounts for 75% of breast cancers. The malignant cells are associated with a fibrous stroma that can be dense (scirrhous carcinoma). The tumor invades through breast tissue into the lymphatics and vascular spaces, to gain access to the regional nodes (auxiliary and, less often, internal mammary) and the systemic circulation. Ductal carcinoma of special type A number of pathological variants are identified, namely medullary carcinoma, tubular carcinoma, and mucinous carcinoma. Invasive lobular carcinoma Lobular carcinomas account for 5-10% of breast cancers. | Local control of the tumor and the prevention of fungation are of major importance to the quality of life. A combination of primary systemic treatment and radiotherapy is commonly used. Many of these patients have indolent ER-positive disease that responds to endocrine therapy with tamoxifen, aromatase inhibitors, or progestins. In younger women with aggressive 'inflammatory' breast cancer, primary chemotherapy is preferred. In patients with a good response to systemic treatment surgery may be feasible. In management of metastatic breast cancer, treatment with tamoxifen, ovarian ablation, progestins, or aromatase inhibitors may provide an response in patients with advanced disease, and in 50-60% of those with ER-positive tumors. Disease that responds to endocrine therapy and then progresses has a 25% response rate with second-line treatment; the response to a third agent is 10-15%. Advanced breast cancer is moderately chemosensitive. Active agents include antracyclines, alkylating agents, and antimetabolites. Combinations such as FAC (5-fluorouracil, doxorubicin, cyclophosphamide) produce response rates of 40-60%, with a median time to progression of around 8 months. 20-50% of women respond to second-line chemotherapy with a taxane and studies are currently evaluating the promising combination of anthracycline plus taxane as first-line chemotherapy. Low-dose radiotherapy provides palliation in these patients. Bisphosphonates are used for treatment of malignant hypercalcemia and can produce healing of some osteolytic metastases. |
| Colorectal cancer | Colorectal cancer is the fourth commonest cancer worldwide. Around two-thirds of a million people will present with the disease each year. It affects men and women almost equally and tends to be more common in 'developed' countries and is particularly common in the US, Europe and Australia. Colorectal cancers area almost always andenocarcinomas. The tumor often starts as a polypoidal mass and then tends to infiltrate into and through the bowel wall. | Surgery is the mainstay of curative therapy for colorectal cancer. Curative resection requires the excision of the primary tumor and its lymphatic drainage with an enveloping margin of normal tissue. The aim of adjuvant chemotherapy is to eradicate micro-metastases and thereby prevent future relapse. Current available chemotherapy does not completely eradicate bulky, advanced metastatic bowel cancer. It does however eradicate mico-metastases in a proportion of patients. The current 'international standard' adjuvant chemotherapy regimen for colon carcinoma is 5-fluorouracil (5FU) given in combination with folinic acid, by bolus intravenous injection. A number of new oral preparations involving pro-drugs of 5FU and/or inhibitors of 5FU catabolism are being evaluated. Other research approaches involve regional delivery of 5FU to the tissues most at risk of containing micro-metastases, via the peritoneal cavity or the hepatic portal vein. New cytotoxic agents are continually under investigation, the most promising of which are Irinotecan (a drug which works by interfering with the nuclear enzyme topoisomerase-I), and Oxaliplatin (which forms covalently bonded adducts with DNA). Understanding the complex pathways by which 5FU acts has allowed the development of biochemical modulation techniques. Leurovorin enhances 5FU toxicity by stabilizing the interaction of thymidylate synthase and active 5FU metabolites. The optimum schedule of 5FU ± leucovorin administration has yet to be elucidated. Intravenous bolus 5FU, usually given with leucovorin, is currently most commonly used. Raltitrexed is a potent inhibitor of thymidylate synthase. It can be used as an alternative to 5FU-based regimes for first-line treatment. It does not |

TABLE 2-continued

| Type of Cancer | Description of the Cancer | Standard of Care and Investigational Treatments |
| --- | --- | --- |
| | | require coadministration of a biochemical modulator. Intra-hepatic 5FU, following surgical placement of a hepatic artery catheter, may be considered for patients with unresectable liver metastases.<br>There currently is no standard second-line chemotherapy treatment regime for patients previously treated with 5FU-based chemotherapy. Radiotherapy in colonic cancer is limited to the palliative situation in most circumstances. The rectum is a suitable target for radiotherapy. Radiotherapy has been used in both the pre-operative and post-operative settings in this disease. In the pre-operative situation there are a group of patients who present with large fixed or tethered tumors that are non-resectable. The conversion rate to respectability is 35-75%, with a dose of 50-60 Gy given over a five-week period. This group is also offered combined chemo-irradiation |
| Anal cancer | Most anal tumors arise from the epidermal elements of the anal canal lining (squamous cell- 85% of anal tumors), though some arise from the glandular mucosa of the uppermost part of the anal canal or from the anal ducts and glands (adenocarcinomas). Malignant melanoma of the anus is very rare. Traditionally, the anal region is divided into the anal canal and the anal margin or verge. | The standard treatment for anal canal tumors was abdominoperineal resection, while anal margin growths were viewed as equivalent to skin tumors elsewhere and treated by local excision. Over the past few years, radiotherapy and/or chemotherapy have become increasingly popular and in many cases the treatment of choice.<br>Non-surgical treatment (chemo-irradiation) for anal cancer has become increasingly popular. The drugs used are usually 5FU and mitomycin C. The radiotherapy consists of 30 Gy of external-beam irradiation over a period of three weeks. Althought Adenocarcinoma is radiosensitive, it is usually treated by radical surgery. |
| Esophageal cancer | Squamous cell carcinoma is the most common histological type, but adenocarcinoma is increasing in incidence.. | Surgical resection is the treatment of choice for early stage disease. Advanced disease is chemosensitive Post-resection irradiation improves the loco-regional control in patients with positive resection margins, but not if there is nodal involvement. The dose is limited to 50 Gy in 25 daily fractions in patients who have undergone a gastric pull-up or intestinal interposition procedure.<br>Pre-operative (neo-adjuvant) chemotherapy can downstage the primary tumor and treat micro-metastases before the post-operative, stimulatory surge of growth factors. Drugs effective in esophageal cancer include: 5FU, cisplatin, mitomycin, paclitaxel, and methotrexate. The most commonly used combination is continuous infusion of 5FU and cisplatin.<br>The majority of esophageal tumors are diagnosed at an advanced stage when resection is not possible. Combined chemo-irradiation therapy is more effective than radiotherapy alone in locally advanced esophageal cancer. |
| Gastric cancer | Globally, stomach cancer is the second commonest cancer.<br>90% of stomach tumors are adenocarcinomas, that are futher divided into 'intestinal' and 'diffuse' types. The remainder are mainly lymphomas and leiomyosarcomas. Intestinal type gastric cancers are ulcerative and occur more often in the distal stomach than diffuse types, including linitinis plastica, which occur throughout the stomach. | The type of surgical resection used in gastric cancer will depend on the site of the tumor; esophogastrectomy may be required for cancers of the esophagus/stomach/jejunum and proximal stomach; total gastrectomy for mid-stomach tumors, and partial gastrectomy may be adequate treatment for tumors in the distal stomach. A futher consideration is the extent of lymphandectomy undertaken.<br>Recent studies of post-operative adjuvant radiotherapy are encouraging. Encouraging results have also been seen with the use of mitomycin C, tegafur, as well as ECF (epirubicin, cisplatin, protracted venous infusion of 5FU) as post-operative adjuvant chemotherapy. |

TABLE 2-continued

| Type of Cancer | Description of the Cancer | Standard of Care and Investigational Treatments |
| --- | --- | --- |
| Small intestine and carcinoid tumors | More than 35 pathological variants of small bowel tumors have been described. Most common are adenocarcinomas that constitute 40% of all malignant small bowel tumors. Carcinoid tumors represent 30% of all small bowel malignancies. Other forms of tumors are lymphomas, sarcomas, as well as benign tumors such as leiomyomas, angiomas and lipomas. | Surgical resection is the most important therapy for all small bowel tumors. Chemotherapy for most malignant small bowel tumors is based around 5FU applied either alone or in combination with leucovorin and/or α-interferon. Sarcomas are treated, as at other sites, with doxorubicin-based regimens. Similarly, lymphomas are commonly treated with regimens such as CHOP (cyclophosphamide, doxorubicin, vincristine and prednisone). Most patients with low-grade carcinoid tumors can be treated with α-interferon alone or in combination with somatostatin analogs. Cytokine therapy (α-interferon) can be used both for adenocarcinomas and carcinoids of the small bowel, either alone or in combination with 5FU. Somatostatin analogs are useful for ameliorating clinical symptoms related to carcinoid tumors and also demonstrate some anti-tumor effect. |
| Cancer of the liver | Primary liver cancer or hepatocellular carcinoma (HCC) is prevalent in areas where hepatitis B is endemic. Hepatitis C infection is becoming an increasing cause. Tumors may also be found incidentally at the time of post-mortem examination in patients with cirrhosis. | Surgery offers the only hope of cure for HCC. However, resection is not possible in many patients. Liver transplantation is appropriate for some cirrhotic patients. For irresectionable tumors systemic chemotherapy has been used. A variety of cytotoxic drugs including doxorubicin, mitozantrone, methotrexate and cisplatinum have been used as single agents or in combination with 5FU. Surgical ligation of the hepatic artery and insertion of a hepatic artery catherter have been used to deprive the tumor of oxygenated blood and to provide a route for the direct administration of cytotoxic chemotherapy. Such techniques have been superceded by the use of chemo-embolization via radiologically placed catheters in the hepatic artery. This technique is less invasive and, using chemotherapy such as adriamycin combined with lipiodol uptake by the tumor, is demonstratable on CT scan. Repeat embolization is performed at 2-3 month intervals and tumor regression with associated regeneration of normal liver may render some tumors resectable. |
| Cancer of the biliary tract | Microscopically, tumors of the biliary tract are adenocarcinomas of the papillary, nodular, or sclerosing type. Papillary tumors develop more commonly in the gall bladder or in the distal bile duct sclerosing and nodular tumors, in the proximal bile duct. Adenocarcinomas without specific features are the most common. Tumors of the bile duct can develop within the bead of the pancreas, in the hepatoduodenal ligament, or at the level of the hepatic hilum,. Hilar cholangiocarcinomas (Klatskin's tumors) account for more than half in most series. Cholangiocarcinomas, especially of the sclerosing and nodular type, infiltrate along the walls of the ducts and the perineural tissue before obstructing the lumen. Metastases to the lymph nodes are seen in some patients undergoing surgery. Direct duodenal invasion and | Chonangiocarcinomas should be resected if there are no distant metastases and no irreparable involvement of the hepatic artery and portal vein. It is advisable to perform a full lymph-node dissection. Although cholangiocarcinomas are not generally considered chemosensitive or radiosensitive, responses to chemotherapy with cisplatin and 5FU and folinic acid have been observed. Newer agents such as gemcitabine and irinotecan are under investigation. For tumors of the gall bladder, incidental tumors diagnosed after a laparoscopic cholecystectomy need no further action unless the gall bladder was ruptured. Tumors of more advanced stages should be treated with radical surgery. Post-operative chemotherapy with cisplatin has yet to be proven to provide beneficial results. Radiotherapy is used in cases of incomplete resection. |

TABLE 2-continued

| Type of Cancer | Description of the Cancer | Standard of Care and Investigational Treatments |
|---|---|---|
| | peritoneal carcinomatisis occur late. Tumors of the gall bladder infiltrate the muscular wall of the gall bladder and the neighboring liver tissue, and spreads to the regional lymph nodes and to the liver. Distant metastases occur late. | |
| Pancreatic cancer | The majority of exocrine tumors are ductal adenocarcinomas and 1-2% are acinar; the remainder are of diverse histology. Genetic abnormalities found in pancreatic cancer include the K-ras oncogene (90-100%) and mutations in p53 (60%), p16 (80%), and SMAD4 (50%) tumor suppressor genes. Spread is mainly to retroperitoneal tissue, the liver, and the peritoneum, with distant metastases to the lung, liver, and the bone. | Resection is the only treatment that offers the possibility of a cure at this time. There is no standard chemotherapy for pancreatic cancer. The nucleoside analogue, gemcitabine, may improve survival compared to a simple 5FU regimen. Adjuvant therapy using 5FU, doxorubicin, and mitomycin C may also increase survival. Patients with good performance status and localized resectable tumor may be considered for radiotherapy, with or without chemotherapy. 5FU has been shown to increase median survival after radiotherapy (35-40 Gy). With 3D-CT planning of external-beam radiotherapy it is possible to deliver 50.4 Gy in 28 daily fractions to pancreatic tumors without exceeding tolerance for the adjacent stomach, bowel, or kidneys. Both eternal-beam radiotherapy (EBRT) and intra-operative radiotherapy (IORT) have been used in the adjuvant settings. |
| Thyroid cancers | Classification of thyroid cancers is made on a histological basis: differentiated (papillary or follicular), anaplastic, lymphoma, and medullary. Lymphomas are high grade immunoblastic non-Hodgkin's tumors. Medullary carcinoma of the thyroid arises from the parafollicular C cells (the cell of origin of calcitonin). For recurrent disease, serum calcitonin serves as a good marker, | Management of differentiated thyroid cancer begins with radical thyroidectomy. Radio iodine therapy (40-80 mCi = 1500-3000 MBq) to ablate the thyroid remnant follows the operation. External beam radiotherapy is delivered to the neck where the tumor was locally invasive at operation (giving a dose of 5000 Gy in 5 weeks). If the patient presents with metastatic disease, or at relapse after partial thyroidectomy, radical thyroidectomy and ablation is still required. Following radical thyroidectomy and radioiodine ablation of the stump, the patient has at least two whole body radioiodine whole body profile scans in the next 1½ years. The treatment of neck nodal disease is surgical resection followed by radioiodine therapy where appropriate. Metastatic disease further afield is treated by serial doses of radioiodine (150 mCi = 5500 MBq). Iodine therapy is continued at 4-6 monthly intervals until maximal remission. In patients who do not relapse, blood checks should be made to ensure thyroid stimulating hormone (TSH) suppression and minimal serum thyroglobulin readings (<2 μg/L). For Anaplastic carcinoma, radiotherapy to the neck is the standard, with palliative chemotherapy as a systemic alternative. These tumors are rarely a radical surgical proposition and do not take up iodine. Lymphomasare treated with a combination of combination chemotherapy and wide field radiotherapy to the neck. For medullary carcinoma, surgical clearance of apparently localized disease to the neck is the first therapeutic step. For recurrent disease,, occasional avidity of uptake to metaiodobenzylguanadine (MIBG) makes radioiodinated MIBG therapy a possibly useful therapeutic modality. |
| Adrenal cancer | The adrenal gland is composed of a cortex and a medulla and the tumors that arise in these two regions are aetiologically and functionally different, reflecting their cells of origin. Adrenocortical | The mainstay of treatment is surgical resection. For phaeochromocytomas with residual or unresectable disease, anti-hypertensive medication may be required to control the blood pressure. If the tumor takes up the radionuclide MIBG, a therapeutic dose of up to 10,000 MBq of $^{131}$I-MIBG may be administered. Although these tumors were traditionally considered to be chemo- |

TABLE 2-continued

| Type of Cancer | Description of the Cancer | Standard of Care and Investigational Treatments |
|---|---|---|
| | carcinomas are usually adenocarcinomas and malignancy is confirmed by the presence of metastatic spread. These tumors extend locally to nodes and the liver but have a high frequency of distant spread. Adrenomedullary tumors (phaeochromocytomas) are rare, and can be difficult to diagnose. | resistant, a combination of dicarbazine (DTIC), vincristine, and cyclophosphamide shows activity. Other regimens which include cisplatin and etoposide have shown promise. For unresectable or metastatic adrenocortical tumors, Mitotane (opDDD) is the first-line treatment. Metyrapone, antiglutethamide, and ketoconazole are second-line medical therapies. The most active chemotherapy drugs appear to be cisplatin and etoposide. The role of external radiotherapy is often for the treatment of symptomatic metastases, usually in bone. |
| Neuroblastoma | Neuroblastoma is the commonest extracranial solid tumor in childhood. Tumors arise in sympathetic nervous tissue. Morphology ranges from a very undifferentiated, small, round cell tumor that may be difficult to distinguish from rhabdomyosarcoma to a highly differentiated ganglioneuroblastoma. | Surguery is usual for tumors in the thorax. In the past, later stage tumors were treated with intensive chemotherapy. It is now recommended that, if possible, surgical clearance be attempted, but if this is not feasible then non-intensive chemotherapy, such as Vincristine, Cisplatin, Etoposide and Cyclophosphamide (OPEC) or Vincristine, Carboplatin, Etoposide and Cyclophosphamide (OJEC), followed by delayed surgery, be used. MIBG posivity, post-operatively, indicates likely residual primary tumor, and local radiotherapy is indicated. An alternative is the use of $I^{131}$ MIBG-targeted radiotherapy. High-dose melphalan with peripheral blood stem rescue is also used. Alternative high-dose intensity strategies, such as administering treatment every 10 days or escalating the dose of cyclophosphamide are also under investigation. For late stages of disease occurring in infants less than 1 year of age, intervention with chemotherapy or radiotherapy may be appropriate. Low-dose irradiation to the liver or low-dose chemotherapy using vincristine or combinations of cyclophosphamide, doxorubicin, or carboplantin/etoposide are indicated. |
| Renal cancer | Adenocarcinomas make up the vast majority of renal cancers. They were previously known as 'hypernephroma' or 'Grawitz tumors'. Transitional cell carcinomas can arise within the urothelium of the renal pelvis and represent the majority of the remaining tumors. Transitional cell carcinomas arise in the renal collecting system. Renal tumors may invade locally or may metastasize to the lungs, lymph nodes, bone and brain. | Renal transitional cell carcinomas are managed similarly to transition cell carcinomas of the bladder. Resection of the tumor is the standard. In patients with limited metastatic disease, nephrectomy may be indicated. Adjuvant therapies consisting of cytotoxic chemotherapies, endocrine therapy, radiotherapy, and interferon have been tested in this disease. Vinca alkaloids are the most commonly used chemotherapeutics. With respect to endocrine therapy, progestins are widely used, although progestagens can also be useful. Biological therapy has been extensively tested in renal cancer. Interleukin-2 (IL-2) is the most widely tested biological agent, alone or in combination with lymphokine-activated killer cells (LAK). Less toxic subcutaneous IL-2 regimens are also effective and can be combined with interferon-$\alpha$ (IFN) and/or cytotoxics. |
| Wilms' tumor | Wilms' tumor (WT) is an embryonal neoplasm arising in the kidneyClassical 'triphasic' WT has stromal, blastemal, and epithelial elements. The bone-metastasizing renal tumor (clear cell sarcoma) and malignant rhabdoid tumor are pathologically and genetically distinct entities. | Surgical extirpation is the fundamental treatment for Wilms' tumor. Pre-operative chemotherapy may be beneficial. The use of chemotherapy and radiotherapy as adjuvants to surgery is an essential part of WT treatment. Chemotherapeutic agents which have been employed include actinomycin D (AMD) plus vincristine (VCR), AMD plus VCR plus doxorubicin, and AMD plus VCR plus doxorubicin plus cyclophosphamide. |
| Cancer of the bladder and ureter | The majority of urothelial tumors are transitional cell carcinomas. Pure squamous carcinomas and adenocarcinomas represent about 5% of tumors, although metaplasia can occur in a primary | The usual surgical procedure is cystoprostatectomy in male patients or anterior bladder exenteration in female patients, with dissection of local lymph nodes. Radical radiotherapy based on CT scan has let to increasing precision and more accurate dosimetry. Usually the entire bladder is treated to encompass the risk of sublinical disease at other sites in the |

TABLE 2-continued

| Type of Cancer | Description of the Cancer | Standard of Care and Investigational Treatments |
|---|---|---|
| | transitional tumor. There is a link between andenocarcinoma of the bladder and presentation of the tumor in the bladder dome, often associated with persisting urachal remnant. Squamous cancers of the bladder are associated with chronic bladder infection by *Schistosoma haematobium*. | urothelium. The technique uses either three or four fields and the common fractionation regimens include treatment to a dose of 64 Gy in 32 fractions over 6½ weeks or 55 Gy in 20 fractions over 4 weeks.<br>Chemotherapy has been investigated as an adjuvant therapy in localized disease either prior to, or following, local treatment with surgery or radiotherapy. Combination chemotherapy has an established role in the palliation of patients with incurable bladder cancer. Typical combinations include M-VAC (methotrexate, vinblastine, adriamycin and cisplatin) and CMV (cisplatin, methotrexate and vinblastine). New drugs under investigation for the management of bladder cancer include taxanes, gemcitabine and ifosphamide. |
| Prostate cancer | Pathogenesis of cancer of the prostate gland is clearly androgen-dependent. Since the development of assays to measure prostate-specific antigen (PSA) to diagnose prostatic disease, the condition has been increasingly diagnosed at an earlier stage. More patients are presenting with early stage disease and suitable treatment strategies are required to cure those that can be cured and palliate optimally those that cannot. | Measurement of PSA should be done in all patients with outflow symptoms, and is routinely used as a screening tool in the US. PSA levels >4 mg/ml are considered to be suspicious; transrectal ultrasound and needle biopsy are called for in these patients. PSA levels >50 ng/ml may be indicative of distant metastases.<br>For treatment of disease confined to the prostate, radical local therapy (prostatectomy or radiotherapy) should be considered. Good results have been seen with neo-adjuvant anti-androgen therapy when followed by radiotherapy in locally extensive disease.<br>Once the tumor has spread beyond the local lymph nodes, useful palliation of the disease can be achieved by hormonal therapy. Treatments used to produce cessation of androgen-driven growth of the cancer include surgical castration, estrogens, steroidal anti-androgens such as cyproterone acetate, non-steroidal anti-androgens (flutamide, bicalutamide), and medical castration with LHRH agonists. The combination of medical castration and anti-androgen therapy has been used.<br>The chemotherapeutic anthracyclines and the related mitoxantrone have been reported to be useful. Radiation therapy offers useful palliation of advanced disease both in bone and soft tissue. In addition, radioactive strontium given by IV injection (150 MBq) has proved effective in relieving bone pain and delaying the progression of symptomatic bone disease. |
| Testicular cancer | Testicular cancer is the commonest cancer in young men. The majority of testicular cancers are germ cell tumors which arise in the germinal epithelium. Both seminomas and non-seminomatous germ cell tumors are thought to arise from pre-existing carcinomas in situ. Non-germ cell testicular tumors have been observed as well.. Non-seminomatous germ cell tumors produce markers in the form of the human chorioric gonadatrophin (HCG) and/or alpha feta protein (AFP) in a majority of cases. Seminomas have no reliable tumor marker with which to monitor disease, although HCG may be raised in about 25% of cases. The lactate dehydrogenase (LDH) may be raised in both tumors as well. | The management of seminoma and non-seminomatous germ cell tumors depends on the stage of the disease. Initial management of testicular germ cell tumors generally includes inguinal orchidectomy, although in cases with widespread metastases immediate chemotherapy may be appropriate. Carcinoma in situ will progress to invasive cancer, either seminoma or non-seminomatous germ cell tumors. Low-dose ratiotherapy to the testis (20 cGy in 10 fractions over 2 weeks) is useful in early stage patients. Standard doses of radiotherapy (30 Gy in 15 fractions over 3 weeks) and chemotherapy are appropriate for later stage patients. |

TABLE 2-continued

| Type of Cancer | Description of the Cancer | Standard of Care and Investigational Treatments |
|---|---|---|
| Ovarian cancer | Ovarian cancer is the fifth commonest cancer in women. Over 80% of ovarian malignancies are epithelial, the rest comprise germ cell and stromal tumors. Epithelial cancers are classified by their cell type (serous, mucinous, endometroid, Brenner, mixed) and by their grade. 80% of women with advanced ovarian cancer have elevated serum CA125 and this marker is valuable in monitoring response to therapy and for detection of early relapse. | Treatment consists of surgery, followed for most patients with platinum-based chemotherapy regimens. For patients who cannot be optimally debulked at initial laparotomy, interval debulking surgery after three cycles of chemotherapy confers a significant survival benefit. The standard chemotherapy regimen currently consists of cisplatin-paclitaxel, although carboplatin-paclitaxel has produced promising results. A number of new agents, including topotecan, liposomal doxorubicin, etoposide, gemcitabine, and altretamine also have shown response in this setting. A number of new approaches are also under consideration, including intra-peritoneal chemotherapy, high-dose systemic chemotherapy, biological response modifiers, metalloproteinase inhibitors, and anti-angiogenic agents. |
| Cancer of the uterine corpus | By far the commonest cancer of the uterine corpus is carcinoma of the endometrium; less common are the uterine sarcomas. Of the latter, some have a glandular element, the so-called Mixed Mesodermal Mullerian Tumors (MMMT) or carcinosarcomas, and some are fibrosarcomas. The epidemiology of uterine sarcomas is less well-defined than endometrial carcinoma, although cases of mixed Mullerian tumor have been reported following tamoxifen therapy. The mixed Mullerian tumors are divided into homologous and heterologous. Homologous MMTs are composed of tissues native to the uterus, whereas heterologous MMTs involve tissue from outside the uterus. Fibrosarcomas may arise de novo or rarely are found in a fibroid uterus. | The usual indication for radiotherapy in endometrial cancer is as adjuvant therapy following hysterectomy but less commonly it may be used as a primary treatment, as a follow-up treatment when residual tumor remains following surgery, for treatment of inoperable tumors, or for treatment in cases of recurrence. Adjuvant radiotherapy is generally delivered with external-beam irradiation of a planned volume (usually four fields) to around 50 Gy over four weeks. Chemotherapeutic combinations such as cisplatin and doxorubicin have been shown to have some activity in endometrial cancer. Progestagens have been widely used in the past but should not be used as long-term adjuvant therapy. Successful treatment of MMTs depends on surgery for localized disease. Residual disease or tumors with nodal or distant metastases are usually incurable. Hysterectomy and bilateral salpingo-oophorectomy should be performed, together with pelvic and para-aortic lymphandectomy. Residual disease can be treated with radiation. Adjuvant radiation may be of use. Chemotherapy (e.g. doxorubicin and ifosfamide) is often used in cases of metastatic disease. |
| Cancer of the cervix | In developing nations, cervical cancer is the most common female cancer. Histology can reveal a spectrum of changes in the epithelium of the cervix, including slight dysplastic changes in the cell architecture, viral cytoplasmic changes, intra-epithelial neoplasia, micro-invasive carcinoma, and frank invasive carcinoma. | When the disease is confined to the cervix, patient management depends on the cytology and/or histology specimens, The type of surgical treatment to be used will depend upon the stage of the disease. Radiotherapy is typically used; a standard therapy consists of external-beam irradiation (40-45 Gy to the pelvis for 4 weeks) followed by intra-cavity brachytherapy (ICT) in the uterus/upper vagina or to the central pelvic structures. Although chemotherapy does not have an established role in the treatment of cervical cancer at this time, patients with recurrent pelvic or systemic metastatic disease may benefit from it. The principal active agents are cisplatin, mitomycin C, ifosfamide, methotrexate, 5-fluorouracil, and bleomycin. Modern management of advanced disease regularly involves the use of concurrent or sequential chemotherapy and radiotherapy. |
| Vaginal and vulvar cancer | Most vaginal malignancies are metastatic, from primary sites in the cervix, vulva, endometrium, or trophoblast (choriocarcinoma). The most common histological types of primary cancer are squamous and adenocarcinoma. | Radical radiotherapy with a combination of pelvic external-beam and utero-vaginal intra-cavitary brachytherapy is the treatment of choice for vaginal cancer. Lower vaginal involvement should prompt consideration of either additional groin node dissection or irradiation. Primary treatment of invasive vulvar cancer consists of surgical excision with clear margins and removal of groin nodes. Chemo-irradiation |

TABLE 2-continued

| Type of Cancer | Description of the Cancer | Standard of Care and Investigational Treatments |
| --- | --- | --- |
| | In primary invasive vulvar cancer, the majority are squamous carcinoma; other types include basal carcinoma and malignant melanoma. | (typically 5FU and mitomycin C combined with radiotherapy) used in cases of advanced disease shows encouraging results. |
| Trophoblastic tumors | Gestational trophoblastic disease (GTD) includes a spectrum of disorders ranging from the pre-malignant complete hydatidiform mole (CHM) and partial hydatidiform mole (PHM), to the malignant invasive mole, gestational choriocarcinoma, and the highly malignant placental-site trophoblastic tumor (PSTT). Both CHM and PHM can develop into invasive moles. However, it is thought that only CHM may progress to the highly malignant choriocarcinoma and the rare PSTT. Choriocarcinoma is a highly malignant form that usually presents within one year of pregnancy. One third of patients present with metastases to the liver, brain or lung. PSTT can develop following a term delivery, non-molar abortion, or CHM. PSTTs are slow-growing malignant tumors composed mainly of cytotrophoblast with very little syncytiotrophoblast, so producing little HCG. However, they often stain strongly for human placental lactogen (HPL) which helps distinguish this tumor from carcinomas, sarcomas, exaggerated placental-site reaction, and placental nodule. In most cases spread occurs by local infiltration with distant metastases occurring late via the lymphatics and blood. | Treatment of hydatiform moles may include gentle suction curettage. Hysterectomy or cesarean section increases the risks of chemotherapy being required to eradicate persistent trophoblastic disease. The stage of the disease is used to determine what chemotherapy regimen is appropriate. Methotrexate is commonly used in later stage patients. Combination chemotherapy comprising etoposide, methotrexate, and actinomycin D (EMA) alternating weekly with cyclophosphamide and cincristine (CO) may be used in very late stage patients. Treatment with methotrexate or EMA/CO regimens continues until the HCG has been normal for six weeks. ChoriocarcinomaWbere it can be safely achieved, excision biopsy of a metastasis should be used to confirm the diagnosis. Patients are scored and treated the same as for molar disease. The behavior or PSTT is quite different from other forms of GTD and it is relatively chemoresistant. The best management is hysterectomy when the disease is localized to the uterus. When metastatic disease is present, patients can respond to multi-agent chemotherapy either alone or in combination with surgery. |
| Cancer of the larynx | Tumors arising from the mucosa of the larynx make up the majority of tumors in the larynx. | The main treatment modalities are radiotherapy and surgery. Induction chemotherapy may select patients with advanced carcinoma suitable for full-course radiotherapy to save the larynx. The voice may be better spared by radiotherapy than surgery. |
| Cancer of the oral cavity | Squamous cancers of the oral cavity are associated with heavy consumption of both tobacco and alcohol. The other less common malignancies of the oral cavity include salivary tumors (adenoid cystic, mucoepidermoid, and adenocarcinoma), melanomas, plasmacytomas, and sarcomas. | Surgery is the most common treatment for early tumors; primary radiotherapy and reserve surgery for later stage disease. Locally advanced disease is best treated by a combination of surgery and radiotherapy. Doses of 50-65 Gy are delivered to the tumor volume, depending .on the extend of the residual tumor. At least part of this dose can be delivered by interstitial therapy. As with head and neck squamous cancers at other sites, chemotherapy (cisplatin, 5FU, methotrexate, bleomycin) is active in advanced disease. |
| Carcinoma of the nasopharynx | NPC spreads into the parapharyngeal space laterally. Any of the cranial nerves can be involved in the tumor. Cervical lymph node spread is common. Distant | NPC is generally both radio- and chemosensitive. Radiotherapy is the mainstay of treatment. The role of surgery is restricted to staging and the elective dissection of neck nodes. Radiotherapy planning is complicated in this disease due to its location in the body. Brachytherapy may be used |

TABLE 2-continued

| Type of Cancer | Description of the Cancer | Standard of Care and Investigational Treatments |
| --- | --- | --- |
| | spread to bone, the liver and lung is common in advanced stage disease, | to increase the dose to the primary site. Local or regional recurrence can be treated by a second radical course of radiotherapy. There may be advantages to using chemotherapy prior to radiotherapy in this disease. Commonly used chemotherapy agents include 5FU, cisplatin and bleomycin. Combined radiation and chemotherapy regimes show promise. |
| Cancer of the nasal cavity and paranasal sinuses | The sinonasal region offers a great histological diversity of tumors, with squamous cell carcinoma the most common. Due to the intimate relationship between the nasal cavity and sinuses and the orbit and skull base, the tumors may spread early to these areas. Additionally, anterior spread into the soft tissues of the face, posterior involvement of the pterygoid region and nasopharynx, and inferior spread to the oral cavity are also commonly encountered. Distant lymphatic and hematogenous spread are rare in the early stages of disease. | Surgery alone or in combination with radiotherapy is required in the majority of cases. Radiotherapy may be given before or after surgery where appropriate. Megavoltage photons are optimally used, in a dose of 60-66 Gy in 30-33 fractions over 6-6.5 weeks. Concurrent chemo-irradiation therapy is under investigation. A number of chemotherapeutic agents (cisplatin, 5FU, methotrexate, bleomycin) have significant activity in recurrent or metastatic disease. |
| Basal cell carcinoma of the external eye-skin, lids, lacrimal glands | Basal cell carcinomas occur frequently on the face and particularly around the eye. They have a predilection for the lower lid margin and adjacent inner canthus. It is unusual for the upper eyelid to be involved. Surgical excision is often appropriate. In more extensive lesions or where surgery is contraindicated, radiotherapy can be given. | Radiotherapy can be used as primary treatment, following excision when the surgical margins are positive, or where a recurrence has occurred. Superficial X-rays (100-150 kV) are appropriate (e.g. 45 Gy in 10 daily fractions). |
| Non-Hodgkin's Lymphoma of the eye and orbit | Lymphoma may involve the upper and lower lids/conjunctiva, major lacrimal gland, or orbit. | Low-grade lymphoma is treated with local radiotherapy; high-grade lymphoma with localized disease is treated with chemotherapy followed by local radiotherapy. Other stages are treated with chemotherapy. |
| Squamous and adenocarcinoma of the eye and orbit | | Squamous carcinoma arising from the skin, lids, or very rarely the conjunctiva can be treated with radiotherapy. Sebaceous and lacrimal gland tumors should be treated primarily with surgery. |
| Melanoma of the intra-ocular region | Melanoma can affect the uveal tract; its most frequent location is the choroids. | Treatment may be observation, radioactive eye plaque (ruthenium or iodine), local resection, charged particles (proton beam), or enucleation. Local resection and proton-beam irradiation are used for larger tumors. |
| Retinoblastoma | This is a rare intra-ocular tumor arising in young children, usually in the first two years of life, | Photocoagulation can be used to treat small tumors not adjacent to the macula or optic disk. Small to moderate tumors can be treated with radioactive plaques. External radiotherapy is used to treat large or multiple tumors. It may be necessary to radiate the entire eye (40 Gy in 20 fractions over 4 weeks). These tumors are often chemosensitive, and chemotherapy can be particularly useful as a neo-adjuvant or when the tumor has a poor prognosis. Useful chemotherapeutic agents include platinum, etoposide, vincristine, doxorubicin and cyclophosphamide. |
| Optic nerve tumors | | Optic nerve tumors are rare and are usually treated by surgery. When excision is not possible, high-dose radiotherapy can be given, usually using paired wedge fields and giving doses on the order of 55 Gy conventionally fractionated. |
| Rhabdomysarcoma of the intra-ocular region | This rare tumor is most frequently located in the orbit. | |

TABLE 2-continued

| Type of Cancer | Description of the Cancer | Standard of Care and Investigational Treatments |
| --- | --- | --- |
| Metastatic disease of the intra-ocular region | Metastatic disease involving the eye is usually associated with choroidal metastases. The commonest tumors implicated are lung and breast. | Treatment with radiotherapy should usually be with a lateral field to the orbit giving 20 Gy in five fractions over a week. The field may be angled five degrees posteriorly to avoid the contralateral lens. Widespread bone metastases may affect the eye. Systemic treatment is often appropriate, although local radiotherapy may be helpful. |
| Salivary gland tumors | The most common tumor of the parotid gland is the pleomorphic adenomal, also known as the mixed parotid tumor. Ocasionally this benign tumor can undergo malignant transformation. Most acinic cell and mucoepidermoid tumors are low grade, although some may be high grade and more aggressive with local invasion and a tendency to metastasize to lymph nodes and through the bloodstream. Wide removal is recommended for pleomorphic adenomas and acinic cell and mucoepidermoid tumors, and will cure the majority of tumors. Carcinomas exhibit more aggressive behavior. | In treatment of malignant salivary gland tumors, adjuvant radiotherapy is most commonly delivered post-operatively, but also as a split-course, giving two-thirds of the treatment before and one-third of the treatment after the operation. Post-operative radiotherapy reduces the incidence of local recurrence. Orthodox radiotherapy techniques use 6-10 MV photons, often with a wedged pair of fields, to give a dose of 55-65 Gy over 6-7 weeks. More aggressive tumors including mucopidermoid, adenoid cystic, and undifferentiated carcinomas appear initially to respond well to chemotherapeutic agents. The most commonly used agents are cisplatin and 5FU. |
| Primary brain tumors | Primary brain tumor pathology is extremely varied reflecting diverse histogenesis. Gliomas are the most common tumors. Primary brain tumors rarely metastasize outside the CNS but are highly infiltrative, with a tendency to spread along white matter tracks to more distant regions of the brain. Spread through cerebrospinal fluid (CSF) to remote areas of the neuraxis is a feature of germ cell tumors, medulloblastoma, and other primitive neuroectodermal tumors. | Surgery and radiotherapy remain the mainstays of treatment for these tumors and most advances involve applying these modalities more effectively to more precisely delineated tumors. Post-operative radiotherapy is normally given. The area irradiated us usually limited to tumor-bearing brain and doses of 30-60 Gy are given over 2-6 weeks. Chemotherapy is usually reserved for relapse. The nitroureas including carmustine (BCNU) and lomustine (CCNU) are the most common agents used. Procarbazine and the platinum compounds and temozolomide may also have some value. Following surgical clearance the application into the resection cavity of sustained-release chemotherapy (BCNU-Gliadel) has shown some benefit. Third generation radiation sensitizers such as the hypoxic cell cytotoxin tirapazamine have shown promise. Angiogenesis inhibitors may be of use, and the drug thalidomide has shown some activity. Modificationof the local environment with O-6-alkylguanine DNA alkyltransferase inhibitors or blood-brain barrier modifiers may improve results with chemotherapeutic agents. |
| Brain metastases | Metastases to the brain from an extracranial primary site is common. | Initial management requires control of the presenting symptoms with medication. Dexamethasone is indicated in the majority of patients. A starting dose of 8-16 mg per daily is common and improvement can often be maintained with doses of 2-4 mg. For patients whose condition is improved following treatment with dexamethasone, radiotherapy can be offered. Typically, the whole brain is irradiated, with a dose of 20 Gy in five fractions being effective. When a solitary metastasis is present, tumor resection, if possible, is the treatment of choice. Post-operatively, whole-brain radiotherapy is given (20 Gy in 5 fractions or 30 Gy in 10 fractions) with or without a local boost. Chemotherapy can be useful in patients with brain metastases from chemo-sensitive primary tumors. It should be used as a first-line therapy (or following resection) in germ cell tumors or as an |

TABLE 2-continued

| Type of Cancer | Description of the Cancer | Standard of Care and Investigational Treatments |
| --- | --- | --- |
| | | alternative to radiotherapy in small cell lung cancer or lymphoma. It can also be used as second-line treatment in less chemo-sensitive tumors such as breast cancer. |
| Primary cutaneous malignant melanoma | Primary cutaneous malignant melanoma arises from melanocytes in the basal skin layer | Treatment is complete excision of the lesion. Late stage melanoma may require dissection of regional lymph nodes. Adjuvant alpha interferon may be of use. Chemotherapeutic regimens include DTIC and/or vindesine; the addition of tamoxifen may be of use. Interleukin 2 combined with with melanoma-directe vaccines are being investigated. Radiotherapy is generally reserved for palliation in metastasized cancer. |
| Non-melanoma skin cancers | Commonest cancer in Western populations. Basal cell carcinomas arise on sun-exposed areas. Variant lesions include nodular, ulcerative, pigmented, superficial, cystic, morphoeic, and multicentric. Squamous cell carcinoma also arises on sun-exposed sites but is faster growing. May metastasize to regional nodes Merkel cell carcinoma is a rare but highly malignant neuroendocrine tumor, commonly spreads to adjacent skin and regional nodes. Apocrine and eccrine gland cancers are rare and usually only locally invasive. Other uncommon skin malignancies include cutaneous angiosarcoma, Kaposi's sarcoma (HIV-associated or endemic), and other soft tissue malignancies. | Standard treatment of basal cell carcinomas is surgical excision. Metastases are rare and are usually curable by surgical excision or radiotherapy. Other treatment strategies include cryosurgery and topical 5FU. Treatment of squamous cell carcinoma is either surgery or radiotherapy. Chemotherapy has been used for disseminated disease (cisplatin, methotrexate, 5FU, bleomycin). Treatment of Merkel cell carcinoma is surgical. Palliative radiotherapy is useful in metastatic disease. |
| Acute lymphoblastic leukemia (ALL) | ALL is the commonest cancer in children. | Treatment of ALL includes: Chemotherapy: induction of remission is routinely achieved by combining vincristine, prednisolone, and 1-asparginase. Additionaly anthracycline is used in adults. Consolidation is a crucial phase following remission. Exposure to new drugs is a key strategy (cyclophosphamide, thioguanine, cytosine arabinoside). Clearance of the central nervous system (CNS) as a sanctuary site is also key. CNS irradiation or MTX intra-thecally or high-dose IV chemotherapy are used. Maintenance of patients in remission is achieved using a cyclic schedule of methotrexate, 6 thioguanine, vincristine and prednisolone. Treatment of high-risk disease involves intensification in consolidation with cyclophosphamide or methotrexate in higher doses along with stem cell transplantation in first remission. Treatment following long remission consists of further chemotherapy or stem cell transplant. |
| Acute mycloid leukemia (AML) | | Antracycline and cytosine arabinose given over 7-10 days is the backbone of treatment. Addition of a third drug (thioguanine or etoposide) is widely used. Giving higher ara-C doses in induction may be of benefit. Following induction, three or four further intensive courses incorporating other drugs (e.g. amasacrine, etoposide, idarubicin, mitoxantrone, and araC at higher doses) are usually given. Maintenance therapy no longer standard but may be useful, along with stem cell transplantation. |

TABLE 2-continued

| Type of Cancer | Description of the Cancer | Standard of Care and Investigational Treatments |
| --- | --- | --- |
| Acute promyelocytic leukemia | | All-transretinoic acid (ATRA) used alone can induce remission. Additional chemotherapy, given alone or subsequent to ATRA is essential. Autologous transplantation or allogenic BMT widely used to consolidate first remissions. Arsenic compounds may be of use, as may refined stem cell transplantation and immunologically based approaches. |
| Chronic lymphoid leukemias | Chronic lymphoid leukemias are a heterogenous group of conditions associated with accumulation of lymphoid cells in the peripheral blood that may infiltrate into the bone marrow. B-cell chronic lymphocytic leukemia is the common leukemia of late middle-age. | Treatment of B-cell chronic lymphocytic leukemia may not prolong survival of patients with lymphocytosis or uncomplicated lymphandenopathy. Systemic therapy is indicated for advanced disease or in cases with diffuse infiltration or low lymphocye doubling time. Chlorambucil is first-line therapy. Single-agent prednisolone (1 mg/kg/day) is useful in advanced disease. Combination chemotherapy using COP or CHOP has been evaluated.. Purines are considered the best second-line therapy. Single agent fludarabine standard. Chlorambucil also used at a dose of 25 mg/m$^2$ IV for 5 days on a 4-6 week cycle for up to 6 cycles. Radiotherapy is effective local treatment for lymph nodes. Splenectomy is effective for massive splenomegaly, anemia or thrombocytopenia and for conditions refactory to prednisolone and cytotoxic therapy. |
| Hodgkin's disease | | Standard therapy for early stage Hodgkin's disease comprises nodal irradiation. Chemotherapy combined with limited (involved field) radiotherapy has been investigated. Chemotherapy regimens include VBM (vinblastine, bleomycin, methotrexate) and ABVD (doxorubicin, bleomycin, vinblastine, dacarbazine). In cases with good prognosis involved field radiotherapy has been used alone successfully. For Advanced stage Hodgkin's disease, MOPP (mustine, vincristine, procarbazine, prednisolone) and its variants were standard until recently. Doxorubicin-based chemotherapy (particularly ABVD) is now considered standard. Newly introduced brief-duration regimens include: Stanford V (mustine, doxorubicin, vinbiastine, prednisolone, vincristine, bleomycin, etoposide); BEACOPP (bleomycin, etoposide, doxorubicin, cyclophosphamide, vincristine, procarbazine, prednisolone); and may be combined with limited field radiotherapy to sites of bulk disease. For salvage therapy in Hodgkin's disease, relapse after radiotherapy frequently responds to chemotherapy. Relapse after first line chemotherapy frequently responds to second line chemotherapy. High-dose chemotherapy and autologous stem cell transplantation becoming standard. Other promising therapies for Hodgkin's disease include high-dose chemotherapy and antibodies against CD30 antigen on R-S cell. |
| Non-Hodgkin's lymphomas(NHL) | Non-Hodgkin's lymphomas(NHL) are a group of malignant diseases arising from cells of the immune system. High grade NHL is considered to have a strong tendency to involve the CNS and is comprised of Burkitt's lymphoma, lymphoblastic lymphoma, and diffuse large B-cell NHL. Diffuse large B-cell NHL is the commonest high-grade NHL. | For low grade NHL, treatment is reserved until active symptoms present. Local radiotherapy is applied to bulky sites. Single-agent chemotherapy (chlorambucil), as well as combination therapy (CHOP) are standard. New treatments include purine analogs (fludarabine, 2-CDA), autologous tranplant, alpha interferon, palliation with anti-CD20 antibody (rituximab), antisense therapy to suppress Bcl-2 protein. Burkitt's lymphoma is treated with intensive chemotherapy with methotrexate, cyclophosphamide, ifosamide, and with intrathecal therapy. Lymphoblastic lymphoma treatment includes emergency management of mediastinal obstruction and prevention of tumor lysis syndrome. Intensive combination chemotherapy |

TABLE 2-continued

| Type of Cancer | Description of the Cancer | Standard of Care and Investigational Treatments |
|---|---|---|
| | | schedules similar to ALL including CNS-directed therapy have been used. Allogenic and autologous progenitor cell transplantation may improve survival. Radiotherapy can cure early stages of diffuse large B-cell NHL. CHOP chemotherapy with radiotherapy to bulk disease is standard. Relapsed patients may respond to salvage chemotherapy and may benefit from autologous progenitor cell transplantation. |
| Myeloma | Myeloma (multiple myeloma, myelomatosis) is due to unregulated proliferation of monoclonal plasma cells in bone marrow. | Chemotherapy (oral mephalan, 4-day pulses every 4 weeks for 3 months) is usually used for palliation. More intensive chemotherapy (VAD, vincristine and adriamycin by IV infusion an oral dexamethasone) may produce response. Combination chemotherapy (e.g. doxorubicin, BCNU, cyclophosamide, melphalan) may produce response as well. High-dose (marrow ablative) melphalan with autologous stem cell transpant can be considered in younger patients. Allogenic transplantation has been reported to improve survival. Oral clodronate may reduce the bone fracture rate when dosed continuously, as may pamidronate. Interferon-a may be used as maintenance therapy. l3rythropoietin may be used to reduce transfusion requirements |
| Osteosarcoma | Osteosarcoma is the commonest primary bone tumor | Surgical resection and use of chemotherapy in the adjuvant (post-operative) or neo-adjuvant (pre- and post-operative) setting has become standard. The most active chemotherapeutics include doxorubicin, cisplatin, ifosamide, and high-dose methotrexate. Osteosarcoma is relatively radio-resistant: radiotherapy rarely used as primary treatment, limited to palliative treatment or in metastases, when combined chemo-irradiation therapy is useful. |
| Ewing's sarcoma | | Chemotherapeutic agents with substantial activity in Ewing's sarcoma include vincristine, doxorubicin, actinomycin D, etoposide, cyclophosphamide, and ifosfamide. Surgery and/or radiotherapy are used to treat the primary tumor. Lung metastases should be treated with conventional chemotherapy with whole-lung irradiation to any residual disease. Bone metasases may benefit from megatherapy after conventional induction treatment-Melphalan, busulphan, TBI, or a combination may be-used as a conditioning regimen |
| Primary malignant spindle cell sarcoma of bone | Primary malignant spindle cell sarcoma of bone includes liposarcoma, angiosarcoma, leiomyosarcoma, and hemangiopericytoma. | Treatment is surgical removal. Chemotherapy is being explored and may be of benefit. |
| Osteoclastoma | Osteoclastoma is usually benign. | Treated by curettage and bone packing or bone resection and insertion of an endoprosthesis. Radiotherapy risks malignant transformation. Response to chemotherapy has been reported. |
| Chondrosarcoma | | For low grade chondrosarcoma tumors, treatment is surgical resection with radiotherapy. For high grade tumors treatment is combined surgery, chemotherapy and radiotherapy. |
| Chordoma | | Surgery is treatment of choice. Radiotherapy (55-60 Gy) used after incomplete resection or as palliation. Particle therapy with protons has shown promise. |
| Solitary plamacytoma | | Treatment is surgical resection or radiotherapy (45-50 Gy). |
| Primary bone lymphoma | | Localized high-grade treated with initial chemotherapy (CHOP) followed by either radiotherapy or surgical excision with endoprosthesis. Multifocal or low-grade disease treated with chlorambucil chemotherapy and radiotherapy. |

TABLE 2-continued

| Type of Cancer | Description of the Cancer | Standard of Care and Investigational Treatments |
| --- | --- | --- |
| Rhabdomyosarcoma (RMS) of the soft tissue | Rhabdomyosarcoma (RMS) of the soft tissue is composed of embryonal RMS and alveolar RMS. | Treatment usually begins with combination chemotherapy followed by local treatment (surgical resection with radiotherapy if excision is incomplete; radiotherapy alone if unresectable). Embryonal RMS may be treated with vincristine plus actinomycin D; may intensify treatment with ifosfamide, doxorubicin, other drugs. Additional drug such as etoposide and carboplatin and high-dose alkylating agent therapy may be of use. Highly sensitive to radiotherapy; common doses with chemotherapy are 40-50 Gy. |
| Soft tissue Ewing's sarcoma and primitive neuroectodermal tumor (PNET) | | Much of management of RMS applies to management of the Ewing's family of tumors. Pre- and post-operative combination chemotherapy is crucial (doxorubicin, actinomycin D, ifosfamide, vincristine). Surgery is the preferred local treatment but radiotherapy is required after incomplete resection or for unresectable tumors. |
| Adult soft tissue sarcomas | | Radical surgery is standard for the primary soft tissue sarcomas (STS). Radiotherapy may reduce local recurrence. Metastases may be surgically removed from the lungs. Chemotherapy for locally recurrent or metastatic disease is largely palliative. Ifosfamide and doxorubicin are the most active chemotherapeutic agents. Combination chemotherapy may be of use. Synovial sarcoma is chemosensitive. Adjuvant chemotherapy is not standard but may be useful. |
| Cancer of unknown primary site | Cancer of unknown primary site is categorized in four broad groups: adenocarcinoma, poorly differentiated carcinoma, undifferentiated malignancy, and squamous carcinoma. | Effective palliation with chemotherapy is indicated if the tumor is chemo-responsive. Combination chemotherapy has been investigated. Hormone therapy is valuable in breast, prostate, and endometrial cancer. Thyroidectomy and radioactive iodine should be used in thyroid cancer. Radiotherapy can be palliative in bone metastases, brain metastases and for lymph node masses. |
| Paraneoplastic syndromes | Paraneoplastic syndromes are pathological conditions caused by a cancer but not due to direct local infiltration or metastatic spread. Cancers commonly associated with paraneoplastic syndromes include: lung (SCLC and NSCLC), pancreatic, lymphoma (NHL and HD), breast, prostate, and ovary. | |
| Endocrine paraneoplastic syndrome | Endocrine paraneoplastic syndrome is a syndrome of inappropriate anti-diuretic hormone (arginine-vasopressin). Other related paraneoplastic syndromes include Cushing's syndrome, hypercalcemia, hypocalcemia, and hypoglycemia. Cushing's syndrome involves inappropriate overproduction of adenocorticotrophic hormone precursors. Hypercalcemia is due to tumor production of parathyroid hormone-related protein. Hypocalcemia is associated with bone tumors and calcitonin-secreting medullary carcinomas of the thyroid. In hypoglycemia, the most likely cause is tumor | Endocrine paraneoplastic syndrome is treated with fluid restriction and democycline (150-300 mg 8 hourly). Specific antibody treatments are used to treat Cushing's syndrome. Standard treatment is to decrease cortisol secretion surgically or medically (metyrapone, ocreotide, ketoconazole). Hypercalcemia is treated with saline hydration and IV pamidronate (60-120 mg). Hypocalcemia is treated with calcium infusions. Hypoglycemia is treated with glucose infusions and tumor debulking. |

TABLE 2-continued

| Type of Cancer | Description of the Cancer | Standard of Care and Investigational Treatments |
|---|---|---|
| | production of the precursor to insulin-like growth factor II. | |
| Neurological paraneoplastic syndrome | Neurological paraneoplastic syndromes include peripheral neuropathy, encephalomyelopathy, paraneoplastic cerebel lar degeneration, cancer-associated retinopathy, Lambert-Easton myasthenic syndrome, and dermatomyositis/ polymyositis. Peripheral neuropathy is caused by axonal degeneration or demyelination. | Peripheral neuropathy is treated with corticosteroids along with treatment for the underlying cancer. Encephalomyelopathy is treated with anti-tumor therapy. Paraneoplastic cerebellar degeneration is responsive to anti-tumor treatments, steroids, and plasmapherisis. Cancer-associated retinopathy is treated with corticosteroids. Lambert-Easton myasthenic syndrome is treated with standard cancer treatment, corticosteroids, and plasma exchange. Dermatomyositis/polymyositis is treated by searching for and treating the tumor along with corticosteroids, and/or azathioprine. |
| Hematological paraneoplastic syndromes | Hematological paraneoplastic syndromes include red cell disorders (erythrocytosis, hemolytic anemia, red cell aplasia) and white cell disorders (autoimmune neutropenia, platelet disorders, coagulopathy). Hemolytic anemia can be autoimmune or micro-angiopathic. | Erythrocytosis is treated with phlebotomy. Hemolytic anemia is treated by treating the tumor; replacing coagulation factors, and supplying IV heparin. |
| Dermatological paraneoplastic syndromes | Dermatological paraneoplastic syndromes include pruritic conditions; pigmentation conditions (Acanthosis nigricans, Vitiligo); erythematous conditions (necrolytic migratory erythema, exfoliative dermatitis-cutaneous); and bullous conditions (pemphigus, dermatitis herpetiformis). | |
| Other paraneoplastic syndromes | Other paraneoplastic syndromes include hypertrophic osteroarthropathy. | Treatment modalities for hypertrophic osteroarthropathy include anti-tumor therapy, non-steroidal antiinflammatories, corticosteroids, and radiation. |
| AIDS-related malignancies | AIDS-related malignancies include Karposi's sarcoma, non-Hodgkin's lymphoma, primary central nervous system (CNS) lymphoma, Hodgkin's disease, cervical cancer, and anal cancer. | The primary goal of treatment of Karposi's sarcoma is to prolong life. Localized treatments include cryotherapy and laser, intra-lesional chemotherapy with vinblastine or interferon, and radiotherapy. Systemic treatment is required if there is widespread cutaneous or visceral involvement. Immunotherapy with interferon is effective. Treatment with vincristine and bleomycin is also used; doxorubicin may be added. Liposomal chemotherapeutics look promising. Treatments such as taxol, beta HCG, trans-retinoic acid, and anti-angiogenic agents such as thalidomide are being tested. For treatment of non-Hodgkin's lymphoma, systemic treatment with chemotherapy is usually used. Radiotherapy may be useful in localized disease: Standard treatment for advanced disease is combination chemotherapy, typically CHOP. Comcomitant intrathecal chemotherapy with mexotrexate and cytarabine is also used. More aggressive chemotherapy regimens may be useful. For primary CNS lymphoma, treatment involves whole-brain radiotherapy in combination with steroids and perhaps intrathecal chemotherapy. Hodgkin's disease is treated by standard chemotherapy is with ABVD (adriamycin, bleomycin, vinbiastine, dacarbazine). |

The formulations of the present invention comprise a therapeutically effective amount of the nitric oxide mimetic formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the formulation according to the judgment of the formulator. The formulations of this invention can be administered to humans and other animals orally, rectally, parenterally, intracisternally, intravaginally, intraperitoneally, topically (as by powders, ointments, or drops), supralingually (on the tongue) sublingually (under the tongue), bucally (held in the buccal pouch), or as an oral or nasal spray. The oral spray may be in the form of a powder or mist which is delivered to the deep lungs by oral inhalation.

In yet other embodiments, the invention provides topical sustained and prolonged release pharmaceutical compositions comprising one or more pharmacological compounds described supra, and a pharmaceutically acceptable carrier, to treat a malignant cell phenotype disorders. One example of a topical formulation includes 75% (w/w) white petrolatum USP, 4% (w/w) paraffin wax USP/NF, lanolin 14% (w/w), 2% sorbitan sesquioleate NF, 4% propylene glycol USP, and 1% compound of the present invention. Such compositions are useful in the treatment of cancer and in controlling and reducing pain associated therewith. Such compositions may comprise a unit dosage of one or more particular active agent(s) (e.g., a NO donor, calcium channel blocker, cholinergic modulator, α-adrenergic receptor antagonist, β-adrenergic receptor agonist, phosphodiesterase inhibitor, cAMP-dependent protein kinase activator, superoxide scavenger, potassium channel activator, SOC inhibitors, benzodiazepine, adrenergic nerve inhibitor, antidiarrheal agent, HMG-CoA reductase inhibitor, smooth muscle relaxant, adenosine receptor modulator, adenylyl cyclase activator, cAMP mimetic, endothelin receptor antagonist, bisphosphonate, cGMP-dependent protein kinase activator, and cGMP mimetic. Preferably, the compositions are administered in unit dosage form to a subject in need of such treatment. Topical sustained and prolonged release compositions are typically variants which include 1) an absorbent in a hydrophilic base; 2) an absorbent in a hydrophobic base; and 3) coated beads containing an absorbent matrix dispersed in a suitable vehicle. Also provided are methods of treating cancer comprising topically administering an effective amount of such compositions (e.g., in unit dosage form) to the appropriate area of the subject in need of such treatment.

Such hydrophilic compositions and preparations of the invention comprise a compound of the invention and a polymer, such as cellulose (methyl cellulose, ethyl cellulose, hydroxy propyl cellulose, etc.), higher molecular weight polyethylene glycol, methacrylic-acrylic acid emulsion, hydrogel, carbopol, ethyl vinyl acetate copolymer, or polyester, etc., to bind the compound of interest to the polymer. The compound-polymer matrix is then dispersed in a hydrophilic vehicle to form a semi-solid. After administration of such hydrophilic composition into the appropriate area, the water in the semi-solid preparation is adsorbed and the polymer matrix with the active ingredient (i.e., the pharmaceutical compound) remains as a coating in the area to which it has been applied. The pharmaceutical compound is then slowly released from this coating.

Hydrophobic compositions and preparations of the invention employ similar polymers as used in the hydrophilic preparations, but the polymer/compound matrix is dispersed into a vehicle, such a plastibase, in the hydrophobic compositions and preparations. Plastibase is a mineral oil base that only partially dissolves the pharmaceutical compound. The semi-solid composition forms a thin coating to which the composition has been applied such as, e.g., the vagina or urethral tract) and slowly releases the active compound. The prolonged action is controlled principally by the solubility of the active ingredient in the vehicle.

The present invention also provides coated beads which are produced by first absorbing a compound of the present invention, or a combination of compounds, on a cellulosic material blended with polyethylene glycol, filler, binder and other excipients. The resulting matrix is then extruded and spheronized (e.g., the process of making into spheres) to create small beads. The beads are then coated to an appropriate thickness with one or more of a suitable material, such as a methacrylic-acrylic polymer, polyurethane, ethyl vinyl acetate copolymer, polyester, silastic, etc. The coating on the beads acts as a rate controlling membrane that regulates the release of the compound from the core beads.

In other embodiments, the invention provides pharmaceutical compositions suitable for oral administration which are provided in unit dosage form comprising per unit dosage a NO donor, calcium channel blocker, cholinergic modulator, α-adrenergic receptor antagonist, β-adrenergic receptor agonist, phosphodiesterase inhibitor, cAMP-dependent protein kinase activator, superoxide scavenger, potassium channel activator, SOC inhibitors, benzodiazepine, adrenergic nerve inhibitor, antidiarrheal agent, HMG-CoA reductase inhibitor, smooth muscle relaxant, adenosine receptor modulator, adenylyl cyclase activator, cAMP mimetic, endothelin receptor antagonist, bisphosphonate, cGMP-dependent protein kinase activator, cGMP mimetic, and a pharmaceutically acceptable carrier. Such compositions are useful for treating cancer, including those disorders and conditions described above.

For delivery to the buccal membranes, typically an oral formulation, such as a lozenge, tablet, or capsule is used. Methods of manufacture of these formulations are known in the art, including but not limited to, the addition of a pharmacological agent to a pre-manufactured tablet; cold compression of an inert filler, a binder, and either a pharmacological compound or a substance containing the compound (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa. The compounds of the present invention can be incorporated into these formulations as well.

For delivery to the nasal or bronchial membranes, typically an aerosol formulation is employed. The term "aerosol" includes any gas-borne suspended phase of the pharmacological agent that is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a pharmacological compound of interest suspended in air or other carrier gas, which may be delivered by insufflation from an inhaler device, for example. For solutions used in making aerosols, the preferred range of concentration of the pharmacological agent is 0.1-100 mg/ml, more preferably 0.1-30 mg/ml, and most preferably, 1-10 mg/ml. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington, *Pharmaceutical Sciences*, see also, Ganderton, et al., *Drug Delivery to the Respiratory Tract*, Ellis Horwood (1987); Gonda, *Critical Reviews in Therapeutic Drug Carrier Systems*, 6:273-313 (1990); and Raeburn, et al., *J. Pharmacol. Toxicol. Methods*, 27:143-159 (1992).

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral formulations can also include adjuvants such as wetting agents, emulsifying and suspending agents, sweetening, flavoring, and perfuming agents. Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In cases where it is desirable to prolong the effect of the nitric oxide mimetic, the absorption of the nitric oxide mimetic from subcutaneous or intramuscular injection can be slowed. This can be accomplished by the use of a liquid suspension of crystalline or amorphous material with poor water solubility. The rate of absorption of the nitric oxide mimetic then depends upon its rate of dissolution which, in turn, may depend upon crystal size and crystalline form. Alternatively, delayed absorption of a parenterally administered formulation is accomplished by dissolving or suspending the nitric oxide mimetic in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the nitric oxide mimetic in liposomes or microemulsions which are compatible with body tissues.

Formulations for rectal or vaginal administration are preferably suppositories, sponges or rings, which can be prepared by mixing the nitric oxide mimetics with suitable non-irritating excipients or carriers such as cocoa butter, polyethylene glycol or a suppository wax which are solid at ambient temperature but liquid at body temperature and therefore melt in the rectum or vaginal cavity thereby releasing the nitric oxide mimetic.

Solid dosage forms for oral administration include capsules, tablets, pills, powders, and granules. In such solid dosage forms, the nitric oxide mimetic is mixed with at least one inert, pharmaceutically acceptable excipient or carrier such as sodium citrate or dicalcium phosphate and/or: fillers or extenders such as starches, lactose, sucrose, glucose, mannitol, and silicic acid; binders such as carboxymethylcellulose, alginates, gelatin, polyvinylpyrrolidinone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as cetyl alcohol and glycerol monostearate; absorbents such as kaolin and bentonite clay; and lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type can also be employed as fillers in soft and hard-filled gelatin capsules using such excipients as lactose or milk sugar as well as high molecular weight polyethylene glycols and the like. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the nitric oxide mimetic only, or preferentially, in a certain part of the intestinal tract, optionally, in a delayed manner. Examples of embedding compositions which can be used include polymeric substances and waxes.

Powders and sprays can contain, in addition to the nitric oxide mimetic, excipients such as lactose, talc, silicic acid, aluminum hydroxide, calcium silicates and polyamide powder, or mixtures of these substances. Sprays can additionally contain customary propellants such as chlorofluorohydrocarbons or alternative non CFC propellants such as DIMEL, also referred to as 1,3,4-A.

Dosage forms for topical or transdermal administration of nitric oxide mimetics include ointments, pastes, creams, lotions, gels, powders, solutions, sprays, inhalants or patches. The nitric oxide mimetic is admixed under sterile conditions with a pharmaceutically acceptable carrier and any preservatives and/or buffers as may be required. Ophthalmic formulation, ear drops, eye ointments, powders and solutions are also contemplated as being within the scope of this invention. Transdermal patches have the added advantage of providing controlled delivery of the nitric oxide mimetic to the body. Such dosage forms can be made by dissolving or dispensing a nitric oxide mimetic in the proper medium. Absorption enhancers can also be used to increase the flux of the nitric oxide mimetic across the skin. The rate can be controlled by either providing a rate controlling membrane or by dispersing the nitric oxide mimetic in a polymer matrix or gel.

The ointments, pastes, creams and gels may contain, in addition to a nitric oxide mimetic, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

A preferred mode of delivery is one which provides a reasonably steady-state delivery of the nitric oxide mimetic, so as to maintain steady-state plasma concentrations. Such delivery avoids any substantial initial spike in plasma concentration of the agent, as it would be desirable to avoid plasma concentrations that produce negative side effects. Transdermal patches and pulsed delivery systems are preferred modes of delivery.

For those formulations containing a nitric oxide mimetic which is commercially available, the low dose formulations for use in the method of the present invention are preferably formulated according to the same methods as the commercially available higher dose formulations, but with lower amounts sufficient to increase, restore or maintain nitric oxide mimetic activity to cells at a level which inhibits or prevents malignant cell phenotypes and/or enhances the efficacy of an antimalignant therapeutic modality. Methods of formulation are within the skill of pharmaceutical formulation chemists and are fully described in such works as *Remington's Pharmaceutical Science*, 18$^{th}$ Edition, Alfonso R. Gennaro, Ed., Mack Publishing Co., Easton, Pa., USA, 1990.

The methods and formulations of the present invention are particularly useful in inhibiting metastases and development of resistance of tumor cells to antimalignant therapeutic modalities including, but not limited to chemotherapeutic agents, radiation therapy, immunotherapies, and thermal therapies. Examples of classes of chemotherapeutic agents useful in combination with low dose NO mimetics include, but are not limited to: anti-angiogenic agents including, but not limited to anti-VEGF agents, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, dauxorubicin, mitomycin, dactinomycin, and plicamycin; endothelin activating agents; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogen or antiestrogens, androgens or antiandrogens, progestins, and luteinizing hormone-releasing hormone antagonist; octreotide acetate; microtubule-disruptor agents, such as ecteinascidins and analogs and derivatives thereof; microtubule-stabilizing agents such as taxanes, for example, TAXOL (paclitaxel), TAXOTERE (docetaxel) and thereof analogs, and epothilones or analogs thereof; vinca alkaloids; epipodophyllotoxins; topoisomerase inhibitors; prenyl-protein transferase inhibitors; and other agents such as hydroxyurea, procarbazine, mitotane, hexamethylmelamine, platinum coordination complexes such as cisplatin and carboplatin, biological response modifiers, growth factors, and immune modulators or monoclonal antibodies. Representative examples of chemotherapeutic agents in these classes useful in the present invention include but are not limited to, actinomycin D, aflacon, bleomycin sulfate, buserelin, busulfan, carmustin, chlorambucil, cladribin, cyclophosphamide, cytarabine, dacarbazine, daunorubicin, discodermolides, doxorubicin hydrochloride, estramustine, estramustine phosphate sodium, etoposide, etoposide phosphate, fludarabine, fluorouracil, flutamide, idarubicin, ifosfamide, interferon, interleukins, leuprolide, levamisole, lomustine, mechlorethamine hydrochloride, melphalan, mercaptopurine, methotrexate, mitomycin C, paclitaxel, pentastatin, pteridine, quinocarcins, rituximab, safracins, saframycins, semustine, streptozocin, tamoxifen, teniposide, thioguanine, thiotepa, topotecan, vinblastine, vincristine, vinorelbine tartrate, aldesleukin (Interleukin-2; proleukin), alemtuzumab (Campath; monocloncal antibody against 21-28 kDa cell surface glycoprotein CD52), altretamine (Hexalen; hexamethylmelamine; HMM), amifostine (Ethyol; WR2721), aminoglutethimide (Cytadren; Epithen), amsacrine (m-AMSA;AMSA;Amsidyl), anastrozole (Arimidex), arsenic trioxide (Trisenox), asparaginase (Elspar; L-Asparagionase), *bacillus* calmette-guerin (BCG; TheraCyst; TICE), bexarotene (Targretin), bicalutamide (Casodex), capacitabine (Xeloda), carmustine (BCNU; Bischloronitrosourea), daunorubicin liposome (DaunoXome), denileukin diftitox (Ontak; $DAB_{389}IL$-2), dexrazoxane (Zinecard; ICRF-187), docetaxel (Taxotere), doxorubicin (Adria' DOX; Rubex; Adriamycin; hydroxydaunorubicin), doxorubicin liposome (Doxil), epirubicin (Ellence; EPI;), erythropoietin (Procrit; Epogen; EPO), exemestane (Aromastin), filgrastim (Neupogen; G-CSF [granulocyte colony stimulating factor]), floxuridine (FUDR; 5-fluoro-2-deoxyuridine), 5-fluorouracil (5-FU; Efudex), gemcitabine (Gemzar), gemtuzumab ozogamicin (CMA-676; Mylotarg), goserelin (Zoladex), imatinib (STI1570; gleevec; $CGP_{57148}B$), interferon alpha (Intron A; Roferon), irinotecan (CPT-11; Camptosar), isotretinoin (Accutane; 13-cis-retinoic acid), letrozole (Femara), mechlorethamine (Mustargen), megestrol acetate (Megace), mesna (Mesnex; 2-mercaptoethanesulfonic acid), mitomycin-C (Mutamycin), mitoxantrone (Novantrone; DHAD; DHAQ), nilutamide (Nilandron), oxaliplatin (Eloxatin; DACH-15 platinum), pemetrexed (Alimta; LY231514), pentostatin (dCF; Nipent; 2'-deoxycoformycin), procarbine (Matulane; Natulanar; N-Methylhydrazine), raltitrexed (Tomudex; ZD1694), sargramostim (Leukine; GM-CSF[granulocyte monocyte colony stimulating factor]), streptozocin (Zanosar; Streptozotocin), UFT (Uracil; Tegafur), temozolomide (Temodar), thalidomide (Thalomid), toremifene (Fareston), trastuzumab (Herceptin, Anti-HER-2 antibocy; rhuMAbHER2), tretinoin (Vesanoid; all-trans retinoic acid), trimetrexate (TMTX; Neutrexin; TMQ), vinorelbine (Navelbine), and any analogs or derivatives thereof.

Animals suffering from cancer can be administered a low dose of a nitric oxide mimetic to inhibit the metastatic potential of the tumor cells as well as to enhance the efficacy of a co-administered antimalignant therapeutic modality targeted at killing the cancer cells. In this embodiment, the nitric oxide mimetic can be administered to animals in combination with other antimalignant therapeutic modalities, following, prior to or during surgical removal or a tumor, and/or following, during, or prior to radiation or thermal therapy. It is believed that this therapy will also enhance the efficacy of anti-VEGF agents targeted at inhibiting angiogenesis of vascular endothelial cells to tumors. In this embodiment, low dose nitric oxide mimetic therapy can be administered to an animal prior to, with, or following administration of an anti-VEGF agent such as anti-VEGF antibody. In this embodiment, it is preferred that the nitric oxide therapy be maintained at least throughout the known active period of the anti-VEGF agent.

Low dose nitric oxide mimetic therapy can also be administered as prophylactic therapy to animals at high risk for developing cancer to prevent the development of cells with a malignant cell phenotype. In this embodiment, a low dose of the nitric oxide mimetic may be administered daily to the animal throughout its life. Accordingly, administration of long-term sustained release dosing formulations may be preferred in these animals. In addition, low dose nitric oxide therapy can be administered to animals suspected of, or known to be, exposed to a factor which lowers cellular nitric oxide mimetic activity so as to induce cells with a malignant cell phenotype. Administration of this low dose nitric oxide therapy is expected to inhibit development of a malignant cell phenotype in these animals. In this embodiment, it is preferred that the nitric oxide mimetic therapy be administered for at least as long as the animal is exposed to the factor. For example, both surgery and anesthesia are believed to be factors which lower cellular nitric oxide mimetic activity so as to induce a malignant cell phenotype. Accordingly, prior to or during a surgical procedure and/or administration of an anesthetic agent in an animal, the animal can also be administered a low dose of a nitric oxide mimetic to prevent and inhibit a malignant cell phenotype. In this embodiment, it is preferred that the nitric oxide mimetic be administered for at least the time in which the animal is undergoing the surgical procedure and/or is under the effects of anesthesia. Similarly, an animal subjected to physical trauma, especially a physical trauma associated with blood loss, a decrease in blood volume or hemorrhage can be administered a low dose of a nitric oxide mimetic to prevent and inhibit a malignant cell phenotype. It is believed that co-administration of a low dose of a nitric oxide mimetic can also be used to inhibit or prevent a malignant cell phenotype which may occur upon administration of pharmacological agents which alter the circulation, e.g. antihypertensives. In this embodiment, the nitric oxide mimetic is preferably administered on a daily basis with the other agents or in a long-term sustained release formulation which extends over the period in which the other agent is administered.

The following nonlimiting examples are provided to further illustrate the present invention.

EXAMPLES

I. Example 1

Materials and Methods

A. Materials

Tissue culture medium (RPMI 1640) and fetal bovine serum (FBS) were purchased from Gibco BRL (Grand Island, N.Y.). Hypoxic conditions were generated using airtight chambers from BellCo Biotechnology (Vineland, N.J.). GTN was obtained as a solution (TRIDIL, 5 mg ml$^{-1}$ or 2.22 M) in ethanol, propylene glycol and water (1:1:1.33) from DuPont Pharmaceuticals (Scarborough, ON). Sodium nitroprusside (SNP) was purchased from Sigma Chemical Co. (St. Louis, Mo). RNA extractions were conducted using a PURESCRIPT RNA isolation kit from Gentra Systems (Minneapolis, Minn.). For the Northern blot analyses, the nylon membranes used for the RNA transfers were purchased from Micron Separations, Inc. (Westboro, Mass.); the uPAR and PAI-1 cDNA probes were cloned in a Bluescript plasmid vector; the [$^{32}$P]-dCTP and the Reflection NEF film were purchased from Dupont/New England Nuclear (Mississauga, ON); and the oligolabelling kit was obtained from Pharmacia Biotech (Piscataway, N.J.). For the in vitro invasion assays, the serum-free EX-CELL 300 culture medium was purchased from JRH Biosciences (Lenexa, Kans.), the Costar TRANSWELL inserts (6.5 mm diameter polycarbonate, membrane, 8 µm pore) were purchased from Corning Costar (Cambridge, Mass.), and the reconstituted basement membrane (MATRIGEL) was bought from Collaborative Biomedical Products (Bedford, Mass.). The plasminogen activator inhibitor-1 (PAI-1) enzyme-linked immunosorbent assay (ELISA) kit was obtained from American Diagnostica (Greenwich, Conn.). For the Western blot analysis of uPAR, the resolved proteins were transferred to Immobilon-P membranes from Millipore (Bedford, Mass.), anti-uPAR antibody (monoclonal antibody [MoAb] 3937) was purchased from American Diagnostica (Greenwich, Conn.), the blotting grade affinity purified goat anti-mouse IgG (H+L) horseradish peroxidase conjugate was obtained from BIO-RAD (Hercules, Calif.), and the antigen was detected by enhanced chemiluminescence (ECL) using reagents from Amersham Canada (Mississauga ON). For the zymographic analyses, the gelatin was purchased from BDH (Toronto, ON), the casein was bought from Sigma Chemical Co. (St. Louis, Mo.) and the plasminogen was from American Diagnostica (Greenwich, Conn.).

B. Cells

The HTR-8/SVneo invasive trophoblast cell line and the MDA-MB-231 metastatic breast carcinoma cell line were used in these experiments. Both the HTR-8/SVneo and the MDA-MB-231 cells were cultured in RPMI-1640 medium supplemented with 5% FBS.

The HTR-8/SVneo cell line was obtained from explant cultures of human first trimester placenta and immortalized by transfection with a cDNA construct encoding the SVneo large T antigen. These cells have been previously characterized and have been maintained in culture for over 130 passages in RPMI 1640 medium supplemented with 5% FBS. They exhibit a high proliferation index and share various phenotypic similarities with the non-transfected parent HTR-8 cells such as in vitro invasive ability and lack of tumorigenicity in nude mice.

The MDA-MB-231 cell line was initially isolated in 1973 from the pleural effusion of a 51-year-old breast cancer patient (Callieau et al. J. Nat. Cancer Inst. 1974 53:661-674).

C. Hypoxic Cell Culture Conditions

Cells were placed in an airtight chamber and were flushed with a gas mixture containing 5% $CO_2$:95% $N_2$ until the oxygen concentration was 0%, as read by a Miniox 1 Oxygen Analyzer (Catalyst Research Corp., Owing Mills, Md.). The cells were then incubated at 37° C. Within the first 2 hours of incubation, the oxygen level in the chambers had equilibrated to approximately 1%, and remained at this level for the remainder of the incubation period.

Alternatively, cells were placed in a chamber in which atmospheric $O_2$ levels were maintained by a PRO-OX $O_2$ regulator (Biospherix, Redfield, N.Y.).

D. Treatment of Cells with Glyceryl Trinitrate (GTN) and Sodium Nitroprusside (SNP)

In these experiments, the cells were treated with varying concentrations of GTN and SNP. The stock solution of GTN was first diluted in phosphate-buffered saline (PBS) to a concentration of $10^{-4}$ M. Following filtration, the GTN solution was diluted in the culture medium to concentrations ranging from $10^{-4}$ M to $10^{-11}$ M. The SNP (originally in crystal form) was dissolved in distilled water and diluted to a concentration of $10^{-5}$ M. Following filtration, the SNP was diluted in the culture medium to concentrations ranging from $10^{-6}$ M, to $10^{-12}$ M.

E. Northern Blot Analyses

Cells were cultured with varying concentrations of GTN and SNP under hypoxic (1% $O_2$) or control (20% $O_2$) conditions at 37° C. In another set of experiments MDA-MB-231 cells were incubated in the presence or absence of LMMA (0.5 mM) for 24 hours under various levels of oxygen (1%, 5% or 20% $O_2$) at 37° C. Following incubation, the total cellular RNA from the cells was isolated using the Gentra PURESCRIPT RNA Isolation Kit. The isolated RNA was subsequently separated by electrophoresis, and transferred to charged nylon membranes. The membranes were prehybridized at 42° C. for approximately 2 hours in a solution containing 50% formamide, 5×Denhardt's solution, 0.5% sodium dodecyl sulfate (SDS), 6×SSC (1×SSC=0.15 M NaCl, 15 mM sodium citrate, pH 7.0) and 100 µg/mL denatured salmon sperm DNA. They were then hybridized with a [$^{32}$P]-dCTP-labeled cDNA probe (uPAR or PAI-1) for approximately 24 hours at 42° C. in a solution composed of 6×SSC, 0.5% SDS, 100 µg/mL denatured salmon sperm DNA and 50% formamide, and containing a cDNA probe (uPAR or PAI-1) which was labeled with [$^{32}$P]-dCTP using a Pharmacia Oligolabelling kit. Following serial washes, the membrane was used to expose Dupont Reflection NEF film. After 1-4 days, the film was developed and analyzed. To correct for differences in the amount of RNA loaded in each sample, 28S rRNA was used.

F. Western Blot Analysis of uPAR Protein Levels

To examine the level of uPAR protein, the cells were first cultured with 20% $O_2$ or 1% $O_2$ in the presence of varying concentrations of SNP or GTN. Following incubations, the cells were lysed using a buffer containing 40 mM HEPES pH 7.2, 100 mM NaCl, 20% glycerol, 0.1 mM EDTA pH 8.0, 0.2% Triton X-100, 1 mM DTT, and 2 mM PMSF. The lysates were then subjected to homogenization, DNA shearing (10 times with a 25⅝-gauge needle), boiling (5 minutes) and centrifugation (15 minutes, 14000 g). The supernatant was collected and stored at −80° C. until use. The samples were subjected to SDS-polyacrylamide gel electrophoresis (PAGE) and the resolved proteins were transferred to an Immobilon-P membrane using a wet transfer apparatus (Bio-Rad Laboratories, Mississauga, ON). The membranes were blocked overnight at 4° C. in a solution containing 1% PBS, and 0.01% Tween20 (PBS-T) as well as 5% casein. The blots were subsequently incubated for 1.5 hours with the monoclonal anti-uPAR antibody [MoAb 3937], followed by six 5 minute washes with PBS-T. The membranes were then incubated with a horseradish peroxidase labeled goat anti-mouse IgG secondary antibody for 1.5 hours. Following six additional 5 minute washes with PBS-T, the antigen was detected by enhanced chemiluminescence and the blots were exposed onto Dupont Reflection NEF film.

G. Measurement of Metalloproteinase and Plasminogen Activator Activity by Zymography To measure the levels of metalloproteinase and plasminogen activator activity, the cells were incubated under hypoxic or control conditions in the presence of varying concentrations of SNP or GTN. The cells were cultured using a serum-free medium (EX-CELL 300). Following incubation, the medium was extracted and centrifuged at 5,000 RPM for 5 minutes. The supernatant was subsequently collected and stored at −80° C. until further use. SDS-polyacrylamide gels were prepared in accordance with well-known procedures. For the analysis of metalloproteinase secretion, the gel contained 0.1% w/v gelatin, and for the analysis of plasminogen activator secretion, the gel was supplemented with 0.1% w/v casein as well as plasminogen (50 µg/mL). The serum-free conditioned medium was then combined with a nonreducing sample loading buffer (0.5 M Tris, 10% SDS, 1% Bromophenol Blue in 2 mL glycerol) in a ratio of 4:1 and was not boiled. Following electrophoresis the gels underwent two 15 minute washes with 2.5%. Triton X-100. This step removed the SDS. After the washes with $H_2O$, the gels were incubated overnight at 37° C. in a solution containing Tris-HCl (pH 7.0) and $CaCl_2$ (5 mM). The gels were stained with 0.4% Coomassie Brilliant Blue R-250 in 40% methanol/10% glacial acetic acid/50% distilled water for approximately 1 hour, and then destained for about 2 hours in 30% methanol/10% glacial acetic acid/60% distilled water. Molecular weight standards showed as dark bands against the lighter blue background and colorless zones appeared where lysis occurred. In the gelatin-containing gels, these areas corresponded to metalloproteinase (gelatinase) activity and in the casein gels, these bands corresponded to plasminogen activator activity. The gels were preserved using a preserving solution (10% glacial acetic acid/10% glycerol/80% distilled water) for 1 hour and were dried on cellophane for 1 hour at 60° C.

H. In Vitro Invasion Assays

Matrigel invasion chambers (modified Boyden chambers) were used to assess the invasive ability of the cells under hypoxic and standard conditions in the presence or absence of various concentrations of GTN or SNP. The chambers consist of cell culture inserts, 6.5 mm in diameter and with a 8 µm pore size membrane. Each membrane was coated with 100 µL of a 1 mg/mL solution of Matrigel diluted in cold serum-free culture medium (EX-CELL 300), and allowed to dry in a laminar flow cabinet for approximately 12 hours. The Matrigel was then rehydrated by incubating it with 100 µL of serum-free medium for approximately 1 hour. After rehydration, cell suspensions containing $5.0 \times 10^4$ or $1.0 \times 10^5$ cells in 100 µL of medium, containing both serum and the nitric oxide treatments, were added to each well. Culture medium containing serum and the respective nitric oxide treatment were then added to each insert. The cells were incubated for 24 hours under either hypoxic (1% $O_2$) or control (20% $O_2$) conditions. Following incubation, the non-invading cells were removed from the upper surface of the membrane by wiping with a cotton swab. The cells on the lower surface of the membrane were fixed for 10 minutes with Carnoy's fixative (25% acetic acid, 75% methanol), and then stained for approximately 3 hours with a 1% toluidine blue, 1% sodium borate solution. Following a rinse in phosphate-buffered saline (PBS), the membrane was removed from the insert housing with a small scalpel blade, mounted onto a microscope slide and coverslipped. Invading cells were then viewed under the microscope at 40× magnification and counted. The invasion index for each treatment was calculated by dividing the number of invading cells by the number of cells which invaded under standard conditions. This value was then multiplied by 100 to obtain a percentage. The standard was given a value of 100% and the treatment values were converted to a percentage of the standard. The results were tested for statistical significance using either the Tukey test for pair-wise multiple comparison procedures or the Student-Newman-Keuls method for pair-wise multiple comparison procedures. See FIG. 1.

I. In Vivo Metastasis Model

C57BL6 mice were injected i.v. (tail vein) with a bolus of $5 \times 10^4$-$10^5$ B16F10 metastatic melanoma cells. Immediately after the tail vein injection, mice were randomly divided into groups of 15 and mice in each group were placed in plexiglass chambers (approximately 3 L) which were continuously flushed with gas mixtures of 20% $O_2$:balance $N_2$ and 10% $O_2$:balance $N_2$, respectively. Gas flows were adjusted to a level which did not allow $CO_2$ build-up within the chambers.

After a 24 hour exposure to an atmosphere of either 20% $O_2$ or 10% $O_2$, mice were removed from the chambers and placed in regular cages kept at room air. Thirteen days later, mice were sacrificed by cervical dislocation, and lungs were removed and fixed in Bouin's fixative (Sigma). Metastatic nodules (many of which appeared black due to the presence of melanin) on the surface of the lungs were counted visually under a dissecting microscope. Data were expressed as the number of lung nodules per $10^4$ cells injected and were analyzed using statistical tests for non-parametric values.

In a second set of experiments, the same protocol was followed except that the B16F10 mouse melanoma cells were incubated for 12 hours in 1% or 20% oxygen in the presence or absence of $2\times10^{-11}$ M GTN. Cells were then removed from plates with trypsin and $5\times10^4$ cells were injected i.v. (tail vein) into C57BL6 female mice. See FIG. 2. Some of the cells treated in vitro were plated onto tissue culture dishes to determine colony-forming ability using the protocol described below in the Section I.J.

J. Colony Formation Assay for Doxorubicin Resistance

The resistance of MDA-MB-231 breast cancer cells to doxorubicin was determined following culture in 20% or 1% oxygen by counting the number of colonies formed. MDA-MB-231 cells were incubated in 1% $O_2$ or 20% $O_2$ for 24 hours. Following incubation, the cells were exposed to diluent (control), 25 µM doxorubicin, 25 µM doxorubicin plus $10^{-6}$ M GTN or 25 µM doxorubicin plus $10^{-10}$ M GTN for 1 hour. The cells were washed and then plated onto 35 mm plates at different dilutions. The cells were incubated for an additional 1-2 weeks in order to allow cell colonies to grow. At the end of the incubation period, the cells were fixed with Carnoy's fixative, stained with Crystal violet, rinsed and allowed to air dry. Colonies were counted visually. The surviving cells under each condition was determined by counting the number of colonies and was expressed as a fraction of the number of colonies that survived without doxorubicin exposure.

II. Example 2

The Activation of sGC and PKG is Linked to the Regulation of Invasive and Metastatic Phenotypes A. Materials Glyceryl Trinitrate (GTN) at a concentration of 2.22 M (Sabex, Boucherville, QC) and Diethylenetriamine/nitric oxide adduct (DETA-NONOate) (SIGMA Chemical Co., St. Louis, Mo.) were used as NO-mimetics. Desferoxamine mesylate (DFO) (SIGMA Chemical Co., St. Louis, Mo.) was used as an iron chelator. 1H-[1,2,4]Oxadiazolo-[4,3-a]Quinoxalin-1-One (ODQ) (SIGMA Chemical Co., St. Louis, Mo.), was used to selectively inhibit soluble guanylyl cyclase. Various concentrations 8-bromoguanosine 3':5'-cyclic monophosphate (8-Br-cGMP) (SIGMA Chemical Co., St. Louis, Mo.) were used to activate cGMP-dependent protein kinase (PKG), and KT5823 (Calbiochem, La Jolla, Calif.) was used to selectively inhibit PKG.

B. Cells

The HTR-8/SVneo line was established from explant cultures of human first trimester placenta and was immortalized by transfection with the large T antigen of simian virus 40. These cells exhibit similar in vitro invasive abilities to their parent HTR-8 cells, and are not tumourigenic in nude mice. They have been maintained in culture for over 130 passages, and require at least 5% serum in order to sustain growth in vitro (see, Graham, Hawley, et al. 1993 ID: 1080).

The MDA-MB-231 is a metastatic breast cancer cell line that was initially isolated in 1973 from a 51-year-old patient {Cailleau, Young, et al. 1974 ID: 982}.

A metastatic murine melanoma (B16F10) (a kind gift of Dr. Ann Chambers, London Regional Cancer Centre, London, ON) was utilized in the experimental metastasis experiments.

All of the cell cultures were maintained in monolayer culture in RPMI 1640 medium (Gibco BRL, Grand Island, N.Y.) supplemented with 5% fetal bovine serum (FBS; Gibco BRL) in a standard Sanyo $CO_2$ incubator (5% $CO_2$ in air, 37° C.; Esbe Scientific, Markham, ON).

C. Culture Conditions

In order to establish hypoxic culture conditions, cells were placed in airtight chambers (BellCo Biotechnology, Vineland, N.J.) which were flushed with a gas mixture of 5% $CO_2$/95% $N_2$ until the desired oxygen concentration was reached. Oxygen levels were maintained through the use of a Pro-Ox Model 110 oxygen regulator (Reming Biospherix, Redfield, N.Y.).

D. Northern Blot Analysis

Following incubation, the total cellular RNA was isolated using a GENTRA PURESCRIPT® RNA Isolation Kit (Gentra Systems, Minneapolis, Minn.). The isolated RNA was subsequently separated by electrophoresis, transferred to a charged nylon membrane (Micron Separations Inc., Westboro, Mass.) and fixed with ultraviolet radiation using a UV Crosslinker (NAME). The membranes were prehybridized at 68° C. for approximately 1 hour in a prewarmed ultrasensitive hybridization buffer, ULTRAhyb™ (Ambion, Austin, Tex.). They were then hybridized overnight at 68° C. with a DIG-labeled uPAR probe. In order to generate the probe, a uPAR cDNA cloned in a Bluescript plasmid vector was linearized. The linear cDNA subsequently underwent in vitro transcription with a DIG-labelled RNA labeling mix and T3 RNA polymerase (Roche Molecular Biochemicals, Indianapolis, Ind.). Following hybridization, the membranes were washed twice in 2×SSC, 0.1% SDS (5 minutes at 68° C.) and then twice in 0.1×SSC, 0.1% SDS (15 minutes at 68° C.). Bands were detected using a DIG luminescent detection kit (Roche Molecular Biochemicals, Indianapolis, Ind.) and the membrane was exposed to Dupont Reflection NEF film (Dupont/New England Nuclear, Mississauga, ON).

E. Western Blot Analysis

Following incubation, the cells were lysed using a buffer containing 40 mM HEPES pH 7.2, 100 mM NaCl, 20% glycerol, 0.1 mM EDTA pH 8.0, 0.2% Triton X-100, 1 mM dithiothreitol (DTT), and 2 mM phenylmethyl sulfonyl fluoride (PMSF). The lysates were then subjected to homogenization, DNA shearing (10 times with a 25⅝-gauge needle), boiling (5 minutes) and centrifugation (15 minutes at 14,000× g). The supernatant was collected and stored at −80° C. until use. The samples were subjected to SDS-polyacrylamide gel electrophoresis (PAGE) and the resolved proteins were transferred to an Immobilon-P membrane (Millipore Corp., Bedford, Mass.) using a wet transfer apparatus (BioRad Laboratories, Mississauga, ON). The membranes were blocked overnight at 4° C. in a solution containing 1% PBS, and 0.01% Tween 20 (PBS-T) as well as 5% dry milk powder. The blots were subsequently incubated for 1.5 hours with the monoclonal anti-uPAR (MoAb 3937; American Diagnostica Inc., Greenwich, Conn.), or a polyclonal soluble guanylate cyclase (sGC) antiserum (Cayman Chemical, Ann Arbor, Mich.) followed by six 5-minute washes with PBS-T. Subsequently, the uPAR membranes were incubated for 1 hour with a horseradish peroxidase labelled goat anti-mouse IgG secondary antibody (Bio-Rad, Hercules, Calif.) and the sGC membranes were incubated for 1 hour with a goat anti-rabbit IgG horseradish peroxidase conjugate (VECTOR Laboratories Inc., Burlingame, Calif.). Following six additional 5-minute washes with PBS-T, the antigen was detected by enhanced chemiluminescence (Amersham Canada Inc., Mississauga, ON) and the blots were exposed onto Dupont Reflection NEF film.

F. In Vitro Invasion Assays

Matrigel invasion assays were used to assess the effect of 8-Br-cGMP on the ability of cells to penetrate through an extracellular matrix. The chambers consisted of 6.5-mm inserts with 8-μm pore membranes (Corning Costar Corp., Cambridge, Mass.). Each membrane was coated with 100 μL of a 2.6 mg/mL solution of Matrigel (Collaborative Biochemical Products, Bedford, Mass.) diluted in cold serum-free medium (EX-CELL 300; JRH Biosciences, Lenexa, Kans.), and allowed to dry in a laminar flow cabinet for approximately 12 hours. The Matrigel was then rehydrated with 100 μL of serum-free medium for approximately 1 hour. After rehydration, cell suspensions containing $5.0 \times 10^4$ cells in 100 μL of RPMI, as well as serum (5% FBS) and 8-Br-cGMP, were added to each well. The cells were incubated for 24 hours in either 1% or 20% oxygen. Following incubation, the non-invading cells were removed from the upper surface of the membrane by wiping with cotton tipped swabs. The cells on the lower surface of the membrane were fixed for 2 minutes with ice-cold methanol, and stained overnight with a 1% toluidine blue, 1% sodium borate solution. Following a rinse in phosphate-buffered saline (PBS), the membrane was removed from the insert with a small scalpel blade, mounted on a microscope slide and cover-slipped. Invading cells were then viewed under the microscope at 40× magnification and counted. The invasion index for each treatment was calculated by dividing the number of invading cells by the number of cells that invaded under standard (20% oxygen) conditions. Invasion indices were expressed as percentages of control (20% oxygen) values. The results were tested for statistical significance using analysis of variance followed by either the Tukey or the Student-Newman-Keels tests for pair wise multiple comparisons.

G. In Vivo Metastasis Experiment

A murine metastasis model was used to assess the effect of 8-Br-cGMP on the metastatic potential of B16-F10 melanoma cells. The cells were incubated for 12 hrs in 1% or 20% oxygen and in the presence or absence of 8-Br-cGMP (1 μM). Following harvesting from culture plates, $5 \times 10^4$ cells were injected intravenously (tail vein injections) into 5-7 week old C57B1/6 female mice. Cells were also plated in tissue culture plates to determine the effect of culture conditions on in vitro colony forming ability. Fourteen days after intravenous inoculation, mice were sacrificed and their lungs were removed and fixed in Bouin's fixative. Both melanotic and amelanotic metastatic colonies were counted under a dissecting microscope. Data were expressed as the number of lung nodules per $5 \times 10^4$ viable cells injected (as determined by in vitro colony-forming ability) and were analyzed using statistical tests for non-parametric values.

H. Measurement of Guanylate Cyclase Levels and Activity

The effects of hypoxia and NO-mimetic treatment on sGC levels were determined using Western Blot analysis. To determine sGC activity, cGMP levels were measured. Briefly, cells were extracted over ice in 1 mL of 6% trichloroacetic acid (BDH Laboratory Supplies, Poole, England). The homogenate was then centrifuged at 13,000 g for 10 min. The supernatant fraction was removed and extracted five times with 2 mL of water-saturated diethyl ether (BDH). The cGMP contained in this fraction was subsequently acetylated and quantitated using an enzyme-linked immuno-sorbent assay (ELISA) kit (STI—Signal Transduction Products, San Clemente, Calif).

Results

I. The Role of Soluble Guanylate Cyclase in the NO Mimetic Prevention of Hypoxia Induced uPAR Upregulation To determine whether a heme protein, such as sGC played a role in the ability of NO mimetics to inhibit the hypoxic upregulation of uPAR, the iron chelator Desferroxamine (DFO) (100 μM) was used. It was found that the upregulation of uPAR that occurred in response to heme disruption with DFO could not be inhibited by GTN ($10^{-10}$ M, $10^{-6}$ M). These results suggest that the NO-mimetic effect is mediated via a heme moiety.

Western blot analysis was used to determine the effects of various oxygen concentrations as well as NOS blockade on sGC protein levels. It was found that the total sGC levels remained unchanged, regardless of the treatment employed. Conversely, using an ELISA for cGMP it was found that sGC activity is decreased after only 2 hours of hypoxia (0.5% $O_2$). Further, this reduction was significantly prevented by the addition of GTN ($10^{-10}$ M, $10^{-6}$ M).

The selective sGC inhibitor ODQ (0.5 μM) was used to determine the role of sGC in the NO mimetic prevention of uPAR upregulation. It was found that the ability of GTN ($10^{-6}$ M) to abrogate the hypoxic induction of uPAR was substantially prevented by ODQ at both the protein and mRNA levels.

J. The Role of PKG in the NO Mimetic Prevention of Hypoxia Induced uPAR Upregulation To determine the role of PKG in the in the oxygen mediated control of uPAR, the PKG activator 8-Br-cGMP ($10^{-3}$-$10^{-7}$ M) was added to cells cultured in 20 and 0.5% $O_2$ or in the presence of DFO (100 μM). In accordance to previous studies, uPAR expression was markedly increased under hypoxic conditions and in the presence of DFO at both the protein and mRNA levels. Interestingly, this induction was significantly abrogated by the addition of 8-Br-cGMP. To assure that the 8-Br-cGMP was activating PKG, a PKG inhibitor (KT5823, 10 μM) was added to the medium. It was found that KT5823 could induce the expression of uPAR, even in the presence of oxygen and that it significantly blunted the effects of 8-Br-cGMP.

K. The Effects of 8-Br-cGMP on Hypoxia-Induced Invasion and Metastasis

As a functional correlate of uPAR expression, an in vitro invasion assay was conducted. It was found that 8-Br-cGMP could significantly inhibit hypoxia-associated invasion.

To extend these findings, an in vivo metastasis assay was conducted. In accordance to previous studies, culture of the B16F10 cells in hypoxic conditions (1% $O_2$) resulted in a marked increase in metastatic lung nodules. This induction was completely abrogated by the addition of 8-Br-cGMP (1 μM). Using a colony formation assay it was found that the 8-Br-cGMP treatment did not affect the viability of the cells.

L. The Effects of NO Mimetics on the Hypoxic Upregulation of In Vitro Invasion and Expression of uPAR To determine the effect of NO mimetics on hypoxia during in vitro invasiveness, an in vitro invasion assay was conducted. While hypoxia increased the in vitro invasiveness of MDA-MB-231 breast carcinoma cells by more than 5-fold (FIG. 5), it was found that low concentrations of two different NO-mimetic drugs, glyceryl trinitrate (GTN; 1 pM and 0.1 μM; P<0.002 and P<0.001 respectively; one-way ANOVA followed by Fisher's test) and sodium nitroprusside (SNP; 10 pM; P<0.001), administered at the beginning of the 24-hour invasion assay.

MDA-MB-231 cells were cultured in 0.5% oxygen for 24 hours to determine the effect on uPAR protein levels. It was found that exposure to 0.5% oxygen resulted in up to 3.5-fold increases (P<0.0001) in uPAR protein levels (FIGS. 6A and 9B) and up to 5-fold increases (P<0.0002) in uPAR mRNA levels (FIGS. 6C, 8A, and 9A). Administration of single doses of GTN (1 pM, 1 nM, and 0.1 µM) to cells incubated for 24 hours in 0.5% oxygen was sufficient to prevent the upregulation of uPAR protein expression (FIG. 6A; P<0.004, <0.005 and <0.001 for each concentration of GTN, respectively). Similarly, the hypoxia-mediated increase in uPAR mRNA levels was also inhibited when a low concentration of GTN (a pM) was used (FIG. 6C; P<0.001).

M. The Effects of NO Synthase Inhibition on uPAR Protein and mRNA Levels

To assess whether endogenous NO inhibits uPAR expression, NO synthesis in MDA-MB-231 cells was blocked by incubation with the NOS inhibitor N-monomethyl-L-arginine (L-NMMA, 0.5 mM). In a manner characteristic of cells exposed to hypoxia, a 24-h incubation with a single dose of L-NMMA resulted in an overall 50% increase in the levels of uPAR protein (FIG. 6B; P<0.004) and a 2.8-fold increase in uPAR mRNA levels in MDA-MB-231 cells even when cultured in 20% $O_2$ (FIG. 6D; P<0.04). In contrast, compared with uPAR expression in cells incubated in 20% $O_2$ alone, no significant increase in uPAR protein (P=0.89) or transcript (P=0.35) levels was observed in cells incubated with a combination of L-NMMA (0.5 mM) and GTN (0.1 nM) in 20% $O_2$ (FIGS. 6B and 6D).

N. The Effects of Hypoxia on sGC Signaling

To determine the effect of hypoxia on cGMP levels, MDA-MB-231 breast carcinoma cells were incubated in 0.5% $O_2$ for 6 hours in the presence of IBMX (500 µM). The results from an ELISA for cGMP revealed that, compared with cells incubated in 20% $O_2$, the MDA-MB-231 cells incubated in 0.5% $O_2$ exhibited a 50% reduction in accumulated cGMP levels (P<0.002; FIG. 7A). This effect of hypoxia on cGMP levels was prevented by co-incubation with the NO mimetic GTN (1 µM).

Western Blot analysis was conducted to determine the effects of hypoxia on sGC protein levels. Soluble GC is a heterodimeric protein consisting of an α1 and a β1 subunit. Culture in hypoxia for 24 hours resulted in a 44% decrease in the levels of the β1 subunit (P<0.0001). In contrast, culture in hypoxia resulted in a 2.3-fold increase (P<0.02) in the levels of the α1 subunit (FIG. 7B). Although the ratio of the α1 and the β1 subunits was altered during hypoxia, the total amount of sGC was not significantly changed.

O. The Role of sGC in the NO-Mediated Inhibition of uPAR Expression

To determine the effect of sGC blocker on the levels of uPAR mRNA, MDA-MB-231 cells were incubated for 24 hours with the selective sGC blocker (ODQ, 0.5 µM). Compared with incubation of cells under control conditions (20% $O_2$ alone), the treatment described above resulted in a 2.7-fold increase (p<0.05) in the levels of uPAR mRNA (FIG. 8A). While the presence of GTN (1 µM) prevented the hypoxic upregulation of uPAR mRNA expression, GTN was unable to block the effect of hypoxia when ODQ was also present in the medium (FIG. 8A).

Soluble GC is a heme-containing enzyme that requires ferrous iron for its biosynthesis and activity. Therefore, to further assess the participation of this enzyme in the regulation of uPAR expression by the NO signaling pathway, MDA-MB-231 cells were cultured in the presence of DFO, which resulted in a 4-fold increase (P<0.007) in the levels of uPAR mRNA (FIG. 8C). In contrast to hypoxia, the effect of DFO on uPAR mRNA expression was not prevented by 1 µM of GTN.

Furthermore, the upregulation of uPAR mRNA and protein expression by hypoxia was significantly reduced (P<0.0001) in a dose-dependent manner (up to 100%) by the presence of 8-Br-cGMP (0.1 µM-10 µM; 24 hours), a non-hydrolysable analogue of cGMP (FIGS. 9A and 9B). Interestingly, the presence of 8-Br-cGMP (1 mM) also resulted in the complete inhibition (P<0.01) of the DFO-induced upregulation of uPAR mRNA expression (FIG. 9C). These results indicate that a major component of the hypoxia- and DFO-mediated stimulation of uPAR expression is the inhibition of sGC.

P. Role of PKG in the NO Mediated Inhibition of uPAR Expression

To further elucidate the role of NO signaling in the regulation of uPAR expression, MDA-MB-231 cells were incubated for 6 hours with the PKG inhibitor KT5823 (10 µM) Northern and Western blot analyses revealed that selective inhibition of PKG, even in 20% $O_2$, resulted in a 1.8-fold (P<0.05) increase in uPAR protein and mRNA expression (FIGS. 10A and 10B). These results demonstrate that PKG activation by cGMP is necessary for the inhibition of uPAR expression by NO.

Q. Effect of 8-Br-cGMP on Hypoxia-Induced Invasion

To determine the effect of 8-Br-cGMP on hypoxia-induced invasion, an in vitro invasion assay was conducted. Results from the in vitro invasion assay using matrigel as a substrate for invasion revealed that, compared to the invasiveness of cells incubated in 20% $O_2$, hypoxia stimulated the invasiveness of MDA-MB-213 cells by 3.9 fold (P<0.0001; FIG. 11). This effect of hypoxia on invasiveness was completely inhibited by the presence of various concentrations of 9-Br-cGMP (0.1 µM-1 mM; FIG. 11).

III. Example 3

The Role of Nitric Oxide in Hypoxia-Induced Chemoresistance in Prostate Cancer Cells Low tumor oxygenation (hypoxia) correlates with increased metastasis and resistance to radiotherapy and chemotherapy. Hypoxia has been shown to be associated with human prostate cancer, and prostate cancers are often highly resistant to chemotherapy. To test whether hypoxia is a major contributor to reduced chemosensitivity in prostate cancer cells and that hypoxia-induced chemoresistance in prostate cancer cells can be inhibited by low concentrations of nitric oxide (NO) mimetic agents, human PC-3 and mouse TRAMP-C2 prostatic adenocarcinoma cells were incubated in 20% $O_2$ or 0.5% $O_2$ for 12 hours in the presence or absence of glyceryl trinitrate (GTN, 0.1 nM). This was followed by a one-hour incubation with doxorubicin and survival was assessed by colony formation assays. Western blot analysis was used to measure NO synthase (NOS) protein levels in cells cultured in 20% and 0.5% $O_2$. Pre-incubation of the two cell lines under hypoxia resulted in increased survival (up to 8-fold for the PC-3 cells and up to 12-fold for the TRAMP-C2 cells; P<0.0001) following exposure to doxorubicin. Co-incubation of the PC-3 and TRAMP-C2 cells with 1 nM of GTN resulted in complete inhibition of the hypoxia-induced resistance to doxorubicin (P<0.0001). Both cell lines expressed all three NOS isoforms (NOS I, NOS II and NOS III), but only the expression of NOS III was significantly increased (P<0.05) in PC-3 cells incubated in 0.5% versus 20% $O_2$. These findings indicate that NO plays an important role in the regulation of chemosensitivity in prostate cancer cells. Furthermore, the results indicate that administration of GTN provides a means of chemosensitizing prostatic carcinomas (FIGS. 12 and 13).

IV. Example 4

Multicellular Resistance to Doxorubicin is Attenuated by Nitric Oxide Mimetics

Previous studies revealed that hypoxia-induced drug resistance in tumor cells cultured in monolayer results from impaired nitric oxide (NO) production. It is also well established that, compared with culture in monolayer, tumor cells cultured as multicellular aggregates (spheroids) exhibit significantly higher levels of resistance to chemotherapeutic agents. The present study demonstrated that chemoresistance associated with spheroid culture is due to decreased NO signalling. Using human MDA-MB-231 breast carcinoma cells in clonogenic assays, survival was determined following doxorubicin exposure and NO mimetic administration to both monolayer and spheroid cultures. Compared with incubation in 20% $O_2$, monolayer cells incubated in 1% $O_2$ exhibited a three-fold increase in resistance to doxorubicin. Administration of glyceryl trinitrate (GTN), at 1 µM, resulted in a 50% attenuation of resistance. Incubation with 200 µM doxorubicin resulted in a 90% decrease in survival of tumor cells cultured as spheroids. Diethylenetriamine/nitric oxide adduct (DETA) at 0.1 mM and 2 µM, and GTN at 0.1 µnM and 1 µM, did not affect the survival of control (doxorubicin-untreated) cells. However, these NO mimetics effectively attenuated the resistance to 200 µM doxorubicin associated with 3D culture by 90% and 30% respectively. These results demonstrate that treatment with NO mimetics can be used as a novel approach to increase the chemosensitivity of solid tumors (FIGS. 14 and 15).

V. Example 5

The Role of cAMP Signaling in the Regulation of Breast Carcinoma Invasiveness

This example demonstrates that the hypoxia-induced increases in uPAR expression and invasion are mediated via a reduction in cGMP-dependent signaling. The cGMP and cAMP systems are intimately connected and cGMP levels have been shown to modulate cAMP levels. Given the importance of cGMP signaling in the regulation of invasiveness and its ability to modulate cAMP signaling, this study demonstrates the role of cAMP and its effector, cAMP-dependent protein kinase (PKA), in the regulation of carcinoma cell invasiveness.

Human breast carcinoma (MDA-MB-231) cells were cultured for 24 hours in 20% or 0.5% $O_2$ in the presence or absence of the adenylyl cyclase activator forskolin (10 µM) and/or the PKA inhibitor H-89 (1 µM). Northern and Western blot analyses showed that forskolin inhibited uPAR mRNA and protein expression at both 20% and 0.5% $O_2$. This effect of forskolin on uPAR expression was prevented by H-89, demonstrating that the effects of forskolin are mediated by the cAMP-dependent activation of PKA. Inhibition of PKA with H-89 also resulted in an up-regulation of uPAR expression that was independent of oxygenation. Using an in vitro invasion assay through reconstituted extracellular matrix (Matrigel®), forskolin inhibited cellular invasion at both 20% and 0.5% $O_2$. Inhibition of PKA activity with H-89 prevented this effect of forskolin and independently enhanced invasiveness.

These findings demonstrate that cAMP-dependent signaling plays an important role in the regulation of carcinoma cell invasiveness, independently of oxygenation status. Furthermore, the cAMP pathway provides a novel pharmacological target for the inhibition of tumor cell invasion and metastasis.

VI. Example 6

Low Dose Nitroglycerin Treatment Decreases PSA Velocity

Methods: Patients with a previous history of prostatectomy that have experienced biochemical failure as per the ASTRO criteria (three successive rises in PSA), PSA<10 (units), stable with sub-clinical disease were included in the study after signing an informed consent. All patients were placed on treatment with continuous low dose transdermal nitroglycerin (~0.03 mg/hr, 24 hours a day). Subjects returned to the study centre for monthly PSA measurements. Subjects were withdrawn from the study if there was evidence of disease progression or other intervening medical events.

Results: In general patients having 5 or more months of therapy have decreased mean PSA velocity from 14%/month to 5.4%/month, 4 of 9 subjects have completed 6 months of therapy. 1 subject (with negative margins) has experienced a decrease in PSA, the remaining 3 subjects (with positive margins) have experienced a decrease in PSA velocity, 3 subjects were withdrawn due to: initiation of cardiac medication, renal failure and MRI positive for spinal canal metastasis identified just after enrollment. No patients experienced drug related adverse events.

Conclusions: The current ongoing pilot open-label study indicates that the use of low dose nitric oxide donor treatment is safe and well tolerated in subjects that have experienced biochemical failure after radial prostatectomy. A benign treatment that provides a decrease in PSA velocity during the early phase of biochemical failure can provide a valuable adjunctive clinical tool in the management of prostate cancer. Based on the current data, the concept of low dose nitric oxide treatment of rising PSA associated with biochemical failure should be assessed in a randomized, placebo controlled clinical study.

VII. Example 7

Preventing the Progression of Cervical Intralesional Neoplasia (CIN) to Cervical Cancer Cervical cancer is most common in developing countries. The cervix is the lower third of the uterus. Cancer of the cervix may originate on the vaginal surface or in the canal. Each year, an estimated 500,000 new cases are diagnosed worldwide with some 250,000 of those women destined to die of their disease. Ample evidence exists to show that both incidence and mortality can be reduced by the use of cervical screening program (Cain J M, et al, Science, 288:1753-1754, 2000). Currently, human papillomavirus (HPV), especially HPVs 16 & 18, has been implicated as the major causal agent in this disease. Symptoms of cervical cancer include vaginal bleeding, post-coital spotting, vaginal discharge, and in advanced cases, pelvic or low back pain with sciatic nerve toot type of pain radiating down to the lower back of the lower extremities.

Women typically receive annual gynecological examination that includes PAP smears which analyses the cytological abnormalities of the cervical epithelial cells. In 1988, a National Institute of Health consensus panel was formed and had a uniformed terminology for reporting cervical cytology. Low grade squamous intraepithelial lesions (LSIL) encompassing HPV changes are considered Grade I CIN. High-grade lesions encompassing Grade II & III CIN present high risk to progress cervical cancer. If the PAP smear results are positive, the next step could be colposcopy and directed biopsy. In patients with gross evidence of tumour, diagnosis is usually confirmed by a directed cervical punch biopsy (Benedet J L et al, International Journal of Gynecology & Obstetrics, 70 (2000), 209-262).

Women diagnosed with CIN of various Grades can be treated with low-dose nitrolycerin, either topically, vaginally, or parenterally, alone or in combination with the standard therapies as recommended by the FIGO Committee on Gynecologic Oncology. Regressing on the Grades of CIN will considered as treatment success. Furthermore, if patients had a Grade II or III CIN, and fail to progress to a confirmed diagnosis of cervical cancer with nitrolycerin treatment, one can conclude that the nitroglycerin treatment has successfully prevent the progression to malignant phenotype. Patients that are in the high risk group, e.g. multiple partners with high existence or potential for HPV infection can stay on the low-dose nitroglycerin treatment to prevent recurrence.

VIII. Example 8

Prolong the Effective Treatment Period and Enhance the Overall Effectiveness of Treating Hormone Refractory/Insensitive Breast Cancer Using Fourth-Line Treatment Option by Oral PDE V Inhibitor Breast cancer is the most common cancer and the second leading cancer death in women. In the United States, there are approximately 100,000 women alive with metastatic breast cancer. Once metastases have developed, breast cancer is rarely, if ever, a "curable" condition. When managing metastatic disease, the treatment objectives are to optimize treatment response, improve survival, and balance these goals with maintaining highest possible quality of life. Some treatments are palliative in nature. With the exception of Herceptin (specific for the HER2 oncoprotein), cytotoxic chemotherapeutic agents remains the standard for advanced hormone insensitive breast cancer.

Advanced breast cancer patients where cancer had progressed on anthracycline, taxane and capecitabine treatment can be considered for the following treatment in order to improve the therapeutic index (relief of cancer symptoms vs. the likelihood of treatment-related toxicities) and overall quality of life. While being treated with one of the fourth-line treatments (e.g., Doxil, navelbine, gemcitabine), the breast cancer patients could also take oral PDE V inhibitor, Viagra 25 mg once daily or other longer lasting PDE V inhibitor such as vanadafil. Overall increase in survival rate and or survival time of these women in comparison with the historical database of a given fourth-line treatment will be considered a treatment success of the PDEV inhibitor, Viagra. Enhancing the quality of life, reduction of pain and discomfort during the survival period is also considered as support of Viagra effectiveness in treating breast cancer patients using fourth-line treatment approach. Viagra could also be used with glucocorticoids such as prednisone to provide additional palliative relief of cancer symptoms.

IX. Example 9

Preventing the Progression of Prostate Cancer

Prostate cancer is an important public health concern, representing the most common visceral cancer and the second leading cause of cancer deaths of North American males. In 1999, the American Cancer Society estimated that approximately 179,300 new cases of prostate cancer will be diagnosed in the United States and about 37,000 men could die of the disease (Landis et al. CA Cancer J Clin 1999 49:8-31). Despite this enormous prevalence, optimal management of both localized and metastatic disease remains elusive. Although screening efforts attempt to detect cancer at early stages, it has been estimated that 25% of men diagnosed with prostate cancer will eventually succumb to metastatic disease (Landis et al CA Cancer J Clin 1999 49:8-31).

Radical prostatectomy is considered a gold therapy treatment of localized prostate cancer and removal of all prostatic tissue should result in undetectable serum PSA within a month if all disease has been eradicated (Landis et al. CA Cancer J Clin 1999 49:8-31); therefore, longitudinal measurement of PSA is currently the most sensitive method for detecting cancer persistence, relapse and progression following radical prostatectomy (Landis et al. CA Cancer J Clin 1999 49:8-31). Except for a few anecdotal reports of prostate cancer relapse in the absence of a PSA rise, clinical evidence of local or distant cancer failure is preceded by months to years with biochemical evidence (that is, a detectable PSA; Landis et al. CA Cancer J Clin 1999 49:8-31). The ten-year actuarial incidence of biochemical failure after radical prostatectomy for clinically localized prostate cancer ranges anywhere from 27% to 57% (Zeitman et al. Urology 1994 43:828-833). A ten-year clinical local recurrence rate of 8%, clinical distant recurrence rate of 9% and any evidence of failure (biochemical or clinical) of 32% have been reported. The median time to PSA evidence of treatment failure ranges from 19 to 24 months and the median interval from biochemical recurrence to clinical evidence of disease is an additional 19 months (range: 7 to 71 months).

Men diagnosed with prostate cancer can be treated with a low-dose NO mimetic such as nitroglycerin or isosorbide dinitrate, preferably orally, sublingually, topically, or parenterally, alone or in combination with the standard therapies (e.g., anti-androgen therapy, radical prostatectomy). Exemplary low-dose NO mimetic therapies are set forth herein in Table 1. Regression or stabilization of serial PSA values is considered a treatment success. Furthermore, if subjects have prostate cancer and fail to progress to a later stage of prostate cancer with low-dose NO mimetic such as nitroglycerin or isosorbide dinitrate treatment, one can conclude that the NO mimetic treatment has successfully prevented the progression of prostate cancer. Subjects in the high-risk group, e.g., with short PSA doubling times or family history can stay on a low-dose NO mimetic (e.g., nitroglycerin or isosorbide dinitrate) treatment indefinitely to prevent development, progression or recurrence of the disease.

X. Example 10

Preventing the Progression of Breast Cancer

There is evidence that the local tumor microenvironment plays an important role in determining the behavior of the tumor cells. Hypoxia (pO2 values of less than 10 mmHg) within the solid tumor mass is an independent marker of a poor clinical outcome for patients with a variety of cancers, and in particular breast cancer. The risk of mortality is significantly increased if a primary tumor undergoes metastasis to a distant site within the body.

Females diagnosed with breast cancer can be treated with a low-dose NO mimetic such as nitroglycerin or isosorbide dinitrate, preferably orally, sublingually, topically, or parenterally, alone or in combination with the standard chemotherapies (e.g. taxol). Exemplary low-dose NO mimetic therapies are set forth herein in Table 1. Regression or stabilization of a primary tumor is considered a treatment success. Subjects in the high-risk group (e.g. family history) can stay on a low-dose NO mimetic (e.g. nitroglycerin or isosorbide dinitrate) treatment indefinitely to prevent development, progression or recurrence of the disease.

XI. Example 11

Effect of GTN Therapy on PSA Levels

PSA levels, a biochemical marker of prostate cancer recurrence, were determined following GTN administration in patients with prostate cancer wherein the prostate is still intact.

In this prostate cancer patient, he received radiation therapy in 1991 as the treatment choice. Subsequently, he was place on anti-androgen therapy as the next line of treatment. One year later, there was an increase of serum PSA level as an indicator of cancer relapse. As shown in FIG. 16, the rate of increase in circulating PSA levels decreased in this patient following commencement of two separate episodes of administration of GTN at 0.03 mg/hour, 24 hours a day, for approximately one month each. In both periods, a reduction of PSA velocity was observed with GTN treatment. Following the commencement of a third episode of administration of GTN at 0.03 mg/hour, 24 hours a day, for approximately one month, a decrease in PSA levels was again observed. This result suggest that NO mimetics such as GTN could improve the effectiveness of anti-androgen therapy treatment alone in 1) time to biochemical failure indicated by continuous increase in PSA velocity and 2) in prolonging the time to full relapse of prostate cancer in men.

Further, as shown in FIG. 17, chronic administration of GTN, transdermally, at a concentration of 0.03 mg/hour dramatically improved the efficacy, as determined by circulating PSA levels, of radiation therapy. Two months after chronic GTN therapy was begun, this patient was administered radiation therapy. As shown in FIG. 17, this combination therapy accelerated the rate of PSA decrease to within three months. The expected average for a similar decrease in PSA levels following radiation therapy alone is twelve months. This result support the use of NO mimetics in enhancing the effectiveness of radiation therapy in treating prostate cancer patients by 1) decrease the serum marker of prostate cancer, i.e. PSA level, 2) potential lead to remission of prostate cancer and 3) maintaining prostate cancer at dormant stage indefinitely.

XII. Example 12

Prostate cancer is now the most commonly diagnosed cancer and the second most common cause of cancer death in men. Prostate cancer is mostly adenocarcinoma that arise from high-grade prostate intraepithelial neoplasia (PIN) which is present in 4-16.5% of needle biopsies and is strongly predictive of co-existing carcinoma, thus warranting a repeat biopsy. Early prostate cancer patients can be effectively treated with available androgen suppression therapy.

The treatment of hormone refractory advanced prostate cancer remains a clinical challenge. In hormone-refractory/insensitive prostate cancer (HRPC) patients who failed one non-estramustine, taxane-containing regimen and entering an estramustine treatment regimen (e.g. 14 mg/kg/day PO in 3-4 individual doses) will be provided with topical nitroglycerin ointment. The nitroglycerin ointment will be applied 4-5 times daily to provide sustained plasma level of nitric oxide. While under the nitroglycerin and estramustine treatment, the PSA levels will be measured monthly. The effect of nitroglycerin treatment will be measured against historical database of estramustine users. A statistic of $\geq 40\%$ patients with $\geq 50\%$ decrease in PSA levels or velocity will be considered a nitroglycerin treatment success. The overall increase in the expected median survival time of 5 months of estramustine mono-therapy, the reduction of pain score and the use of pain medication, or improvement in patients' ability to maintain cognitive function and to copy with the advanced disease will also considered as clinically meaningful to add nitroglycerin treatment to the standard of care of these patients.

Example 13

Preventing the Recurrence of Malignant Breast Cancer Following Lumpectomy Procedure Patients with localized early stage non-metastatic breast cancer may elected to undergo a lumpectomy procedure to remove the malignant tissue. Prior to the surgery, patients may start with first line anti-malignant therapy to reduce the tumor volume. To improve the effectiveness of this treatment, patients could start taking nitric oxide mimetics such as Viagra (25 mg or 50 mg) daily continuously during the first line therapy, right after the surgery and chronically post-surgical procedure to prevent relapse of the breast cancer or other form of cancer. Prolong remission period against the history database and/or better quality of life will be considered a treatment success.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for controlling, treating and/or decreasing progression of cancer, malignancies, and/or tumor angiogenesis in a human subject, said method comprising:

administering a low dose of a nitric oxide mimetic to said human subject, to control, treat and/or decrease progression of said cancer, malignancies, and/or tumor angiogenesis;

wherein said nitric oxide mimetic is an organic nitrate;

wherein said low dose is 3 to 10,000 fold lower than a dose of said nitric oxide mimetic that produces vasodilation in said human subject, and wherein said low dose of said nitric oxide mimetic does not induce substantial tolerance in said human subject wherein said low dose of a nitric oxide mimetic enhances the efficacy of, and/or decreases the resistance to an antimalignant therapeutic modality; and wherein said antimalignant therapeutic modality includes radiation therapy, thermal therapy, immunotherapy, or chemotherapy, or a combination thereof.

2. The method according to claim 1, wherein said nitric oxide mimetic is administered at a level which delays and/or reduces development of tolerance to the nitric oxide mimetic and/or unwanted side effects.

3. The method according to claim 1, wherein said nitric oxide mimetic is administered alone.

4. The method according to claim 1, wherein said nitric oxide mimetic:
  (1) inhibits the metastatic potential of a tumor or malignant cell phenotype by decreasing the invasiveness, progression, growth and/or metastases of cells exhibiting a malignant phenotype; inhibiting the survival and/or growth of cells exhibiting a malignant phenotype; decreasing the progression and/or metastases of cells exhibiting a malignant phenotype; increasing the regression of cells exhibiting a malignant phenotype; and/or facilitating the killing of cells exhibiting a malignant phenotype;
  (2) maintains a malignant tumor in a dormant or quiescent state at its primary and/or secondary site; or
  (3) inhibits or decreases progression of tumor angiogenesis in a subject at high risk of developing cancer and/or exposed to factors known to decrease nitric oxide activity in a human subject, optionally wherein said factors include decreased arginine levels, exposure to nitric oxide synthase antagonists, exposure to nitric oxide scavengers, changes in nitric oxide synthase expression, change in cofactors, glucose deprivation, surgical procedures, administration of anaesthetic agents, administration of pharmacologic agents which alter circulation, traumatic injuries, physical trauma, blood loss, decreased blood volume, or hemorrhage, or combinations thereof.

5. The method according to claim 1, wherein the cells exhibiting the malignancies are selected from malignant cells, invasive cells, cells and tissue(s) that facilitate the malignant process, and combinations thereof; optionally wherein the malignant cell phenotype is controlled or treated, or its progression is decreased by improving response to an antimalignant therapeutic modality.

6. The method according to claim 1, wherein cancer is diagnosed or monitored by measuring a tumor selective marker present in said human subject.

7. The method according to claim 6, wherein said nitric oxide mimetic decreases or decelerates increases of the level of said tumor marker.

8. The method according to claim 1, wherein said cancer comprises gastric cancer, gastrointestinal cancer, testicular cancer, prostate cancer, prostatic adenocareinoma, breast cancer, metastatic melanoma, colorectal cancer, or lung cancer, or combinations thereof; optionally wherein the cancer or other malignancies, and/or tumor angiogenesis in the human subject comprises benign prostatic hyperplasia or molar pregnancy.

9. The method according to claim 1, wherein the antimalignant therapeutic modality comprises radiation therapy and said nitric oxide mimetic is administered during the radiation therapy.

10. The method according to claim 1, wherein said chemotherapy comprises administration of a chemotherapeutic agent that is an anti-angiogenic agent, an antimetabolite, an antibiotic, an endothelin activating agent, an enzyme inhibitor, a hormonal agent, ocreotide acetate, a microtubule-disruptor agent, a microtubule-stabilizing agent, a vinca alkaloid, a epipodophyllotoxin, a topoisomerase inhibitor; a prenyl-protein transferase inhibitor, hydroxyurea, procarbazine, mitotane, hexamethylmelamine, a platinum coordination complex, a biological response modifier, a growth factor, an immune modulator, or a monoclonal antibody, or a combination thereof.

11. The method according to claim 1, wherein said nitric oxide mimetic is a known vasodilatory compound and said mimetic is administered at a dose of at least 3 to 10,000-fold lower than the dose of nitric oxide mimetic known to produce vasodilation in said human subject.

12. The method according to claim 2, wherein said unwanted side effects are selected from vasodilation, headache, flushing, syncope, dizziness and hypotension.

13. The method according to claim 1, wherein said nitric oxide mimetic is administered in combination with an antimalignant therapeutic agent.

14. The method according to claim 1, wherein the dose of nitric oxide mimetic is 100 to 10,000-fold lower than a dose of nitric oxide mimetic that produces vasodilation in said human subject.

15. The method according to claim 1, wherein said nitric oxide mimetic is a known vasodilatory compound and is administered at a dose 100 to 10,000-fold lower than the dose known to produce vasodilation in said human subject.

16. The method according to claim 6, wherein the tumor selective marker is prostate specific antigen (PSA).

17. The method of claim 1, wherein the cancer is prostate cancer.

18. The method of claim 1, wherein the nitric oxide mimetic is nitroglycerin (GTN).

19. The method of claim 1, wherein the nitric oxide mimetic is isosorbide 5-mononitrate (ISMN).

20. The method of claim 1, wherein the nitric oxide mimetic is isosorbide dinitrate (ISDN).

21. The method of claim 1, wherein the nitric oxide mimetic is pentaerythritol tetranitrate (PETN).

22. The method of claim 1, wherein the nitric oxide mimetic is erythrityl tetranitrate (ETN).

23. The method of claim 1, wherein the cancer is lung cancer.

24. The method of claim 1, wherein the cancer is colorectal cancer.

* * * * *